(12) United States Patent
Shturman

(10) Patent No.: US 8,109,954 B2
(45) Date of Patent: Feb. 7, 2012

(54) ROTATIONAL ATHERECTOMY DEVICE WITH DISTAL PROTECTION CAPABILITY AND METHOD OF USE

(75) Inventor: Leonid Shturman, Nyon (CH); Lela Nadirashvili, legal representative, Nyon (CH)

(73) Assignee: Lela Nadirashvili, Nyon (CH)

(*) Notice: Subject to any disclaimer, the term of this patent is extended or adjusted under 35 U.S.C. 154(b) by 315 days.

(21) Appl. No.: 11/920,463

(22) PCT Filed: May 25, 2006

(86) PCT No.: PCT/IB2006/001368
§ 371 (c)(1),
(2), (4) Date: Nov. 15, 2007

(87) PCT Pub. No.: WO2006/126076
PCT Pub. Date: Nov. 30, 2006

(65) Prior Publication Data
US 2009/0069829 A1 Mar. 12, 2009

(30) Foreign Application Priority Data
May 26, 2005 (GB) .................................. 0510802.5

(51) Int. Cl.
*A61B 17/22* (2006.01)
(52) U.S. Cl. ....................................................... 606/159
(58) Field of Classification Search .................. 606/108, 606/159, 170, 194, 200, 180; 604/19, 22
See application file for complete search history.

(56) References Cited

U.S. PATENT DOCUMENTS

| | | | |
|---|---|---|---|
| 1,431,416 A * | 10/1922 | Parsons et al. | 74/597 |
| 1,916,085 A | 6/1933 | Summers et al. | |
| 4,931,635 A * | 6/1990 | Toyama | 250/225 |
| 4,990,134 A | 2/1991 | Auth et al. | |
| 5,250,060 A * | 10/1993 | Carbo et al. | 606/159 |
| 5,314,438 A | 5/1994 | Shturman | |
| 5,342,292 A | 8/1994 | Nita et al. | |
| 5,361,285 A | 11/1994 | Formanek et al. | |
| 5,584,843 A | 12/1996 | Wulfman et al. | |
| 5,681,336 A * | 10/1997 | Clement et al. | 606/159 |
| 5,868,708 A * | 2/1999 | Hart et al. | 604/104 |
| 6,010,533 A | 1/2000 | Pope et al. | |

(Continued)

OTHER PUBLICATIONS

Excerpt from Deposition of Dmitri Prudnikov, Mar. 5, 2008, 7 pages.
Exhibits Nos. 14, 31 & 32, from Deposition of Dmitri Prudnikov, Mar. 5, 2008, 3 pages.

(Continued)

*Primary Examiner* — S. Thomas Hughes
*Assistant Examiner* — Ashley Cronin
(74) *Attorney, Agent, or Firm* — Fish & Richardson P.C.

(57) ABSTRACT

A rotational device for removing a stenotic lesion from within a vessel of a patient is disclosed. The device comprises a flexible hollow drive shaft having a distal end insertable into the vessel and an abrasive element located on the drive shaft proximal to the distal end of the drive shaft to abrade a stenotic lesion when the drive shaft rotates. The hollow drive shaft defines a lumen for fluid supplied into the drive shaft to flow in an antegrade direction along the lumen and into the vessel from the drive shaft distal to the abrasive element so that the fluid entering the vessel flows in a retrograde direction over the abrasive element and die drive shaft to entrain debris abraded by the abrasive element for removal of said debris from the patient.

11 Claims, 63 Drawing Sheets

U.S. PATENT DOCUMENTS

| | | | |
|---|---|---|---|
| 6,132,444 | A | 10/2000 | Shturman et al. |
| 6,146,395 | A | 11/2000 | Kanz et al. |
| 6,241,706 | B1 * | 6/2001 | Leschinsky et al. ....... 604/99.01 |
| 6,485,500 | B1 * | 11/2002 | Kokish et al. ................. 606/194 |
| 6,685,718 | B1 * | 2/2004 | Wyzgala et al. .............. 606/170 |
| 2002/0099367 | A1 * | 7/2002 | Guo et al. ....................... 606/43 |
| 2002/0138088 | A1 * | 9/2002 | Nash et al. .................... 606/159 |
| 2004/0158270 | A1 | 8/2004 | Wyzgala et al. |

OTHER PUBLICATIONS

Declaration of Dmitri Prudnikov, Apr. 23, 2007, 1 page.
Excerpt from Deposition of Dmitri Prudnikov, Mar. 6, 2008, 54 pages.
Exhibits Nos. 33-39 from Deposition of Dmitri Prudnikov, Mar. 6, 2008, 47 pages.
Declaration of Aleksey Filippov, Apr. 23, 2007, 1 page.

* cited by examiner

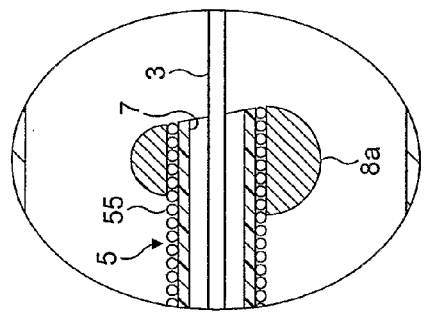
FIG. 2³
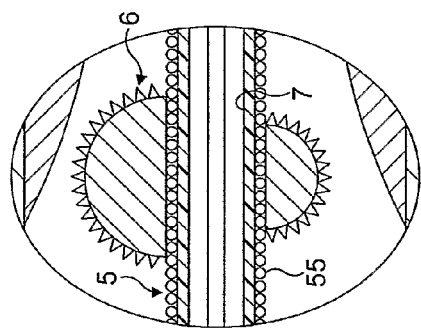
FIG. 2²
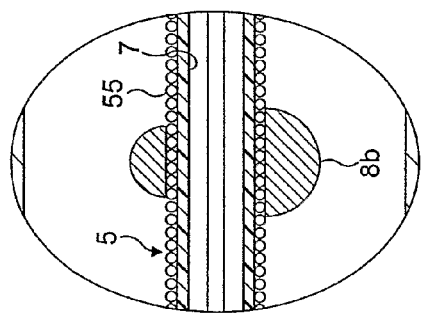
FIG. 2¹
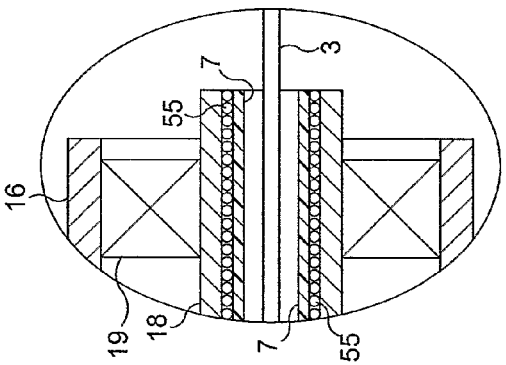
FIG. 2⁵
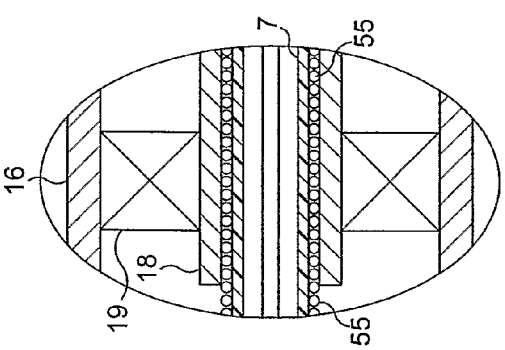
FIG. 2⁴

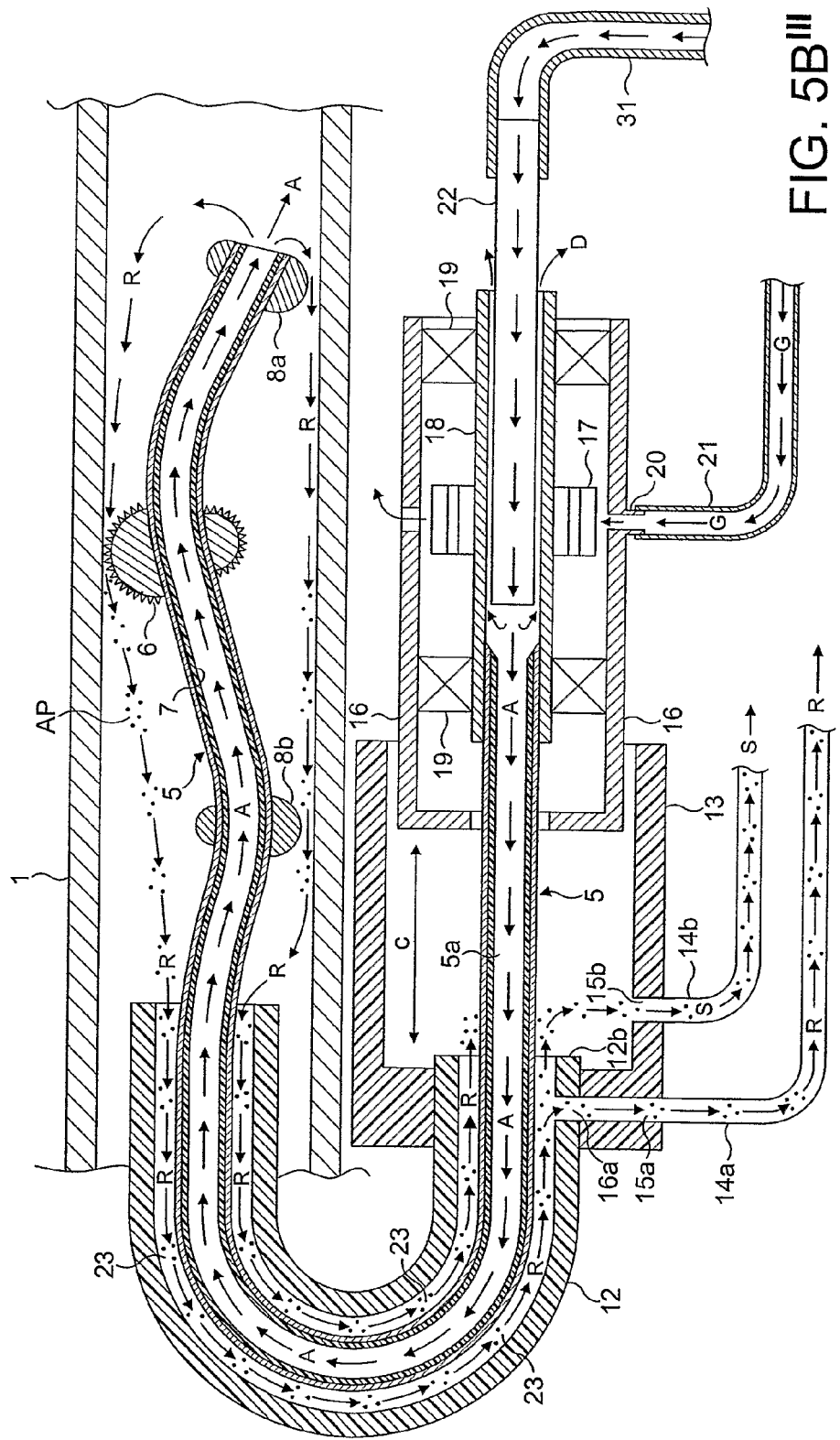
FIG. 5B^III

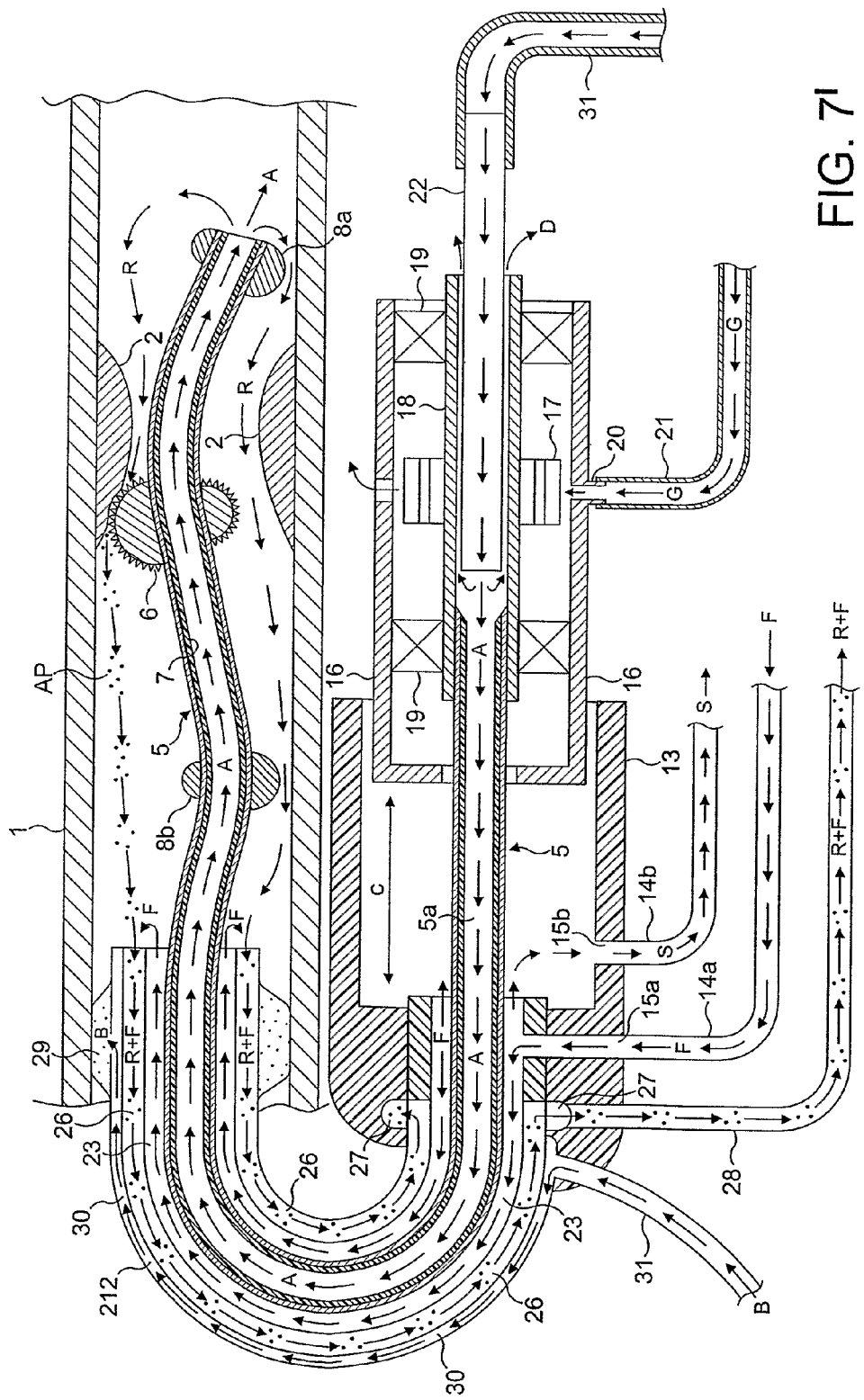
FIG. 7¹

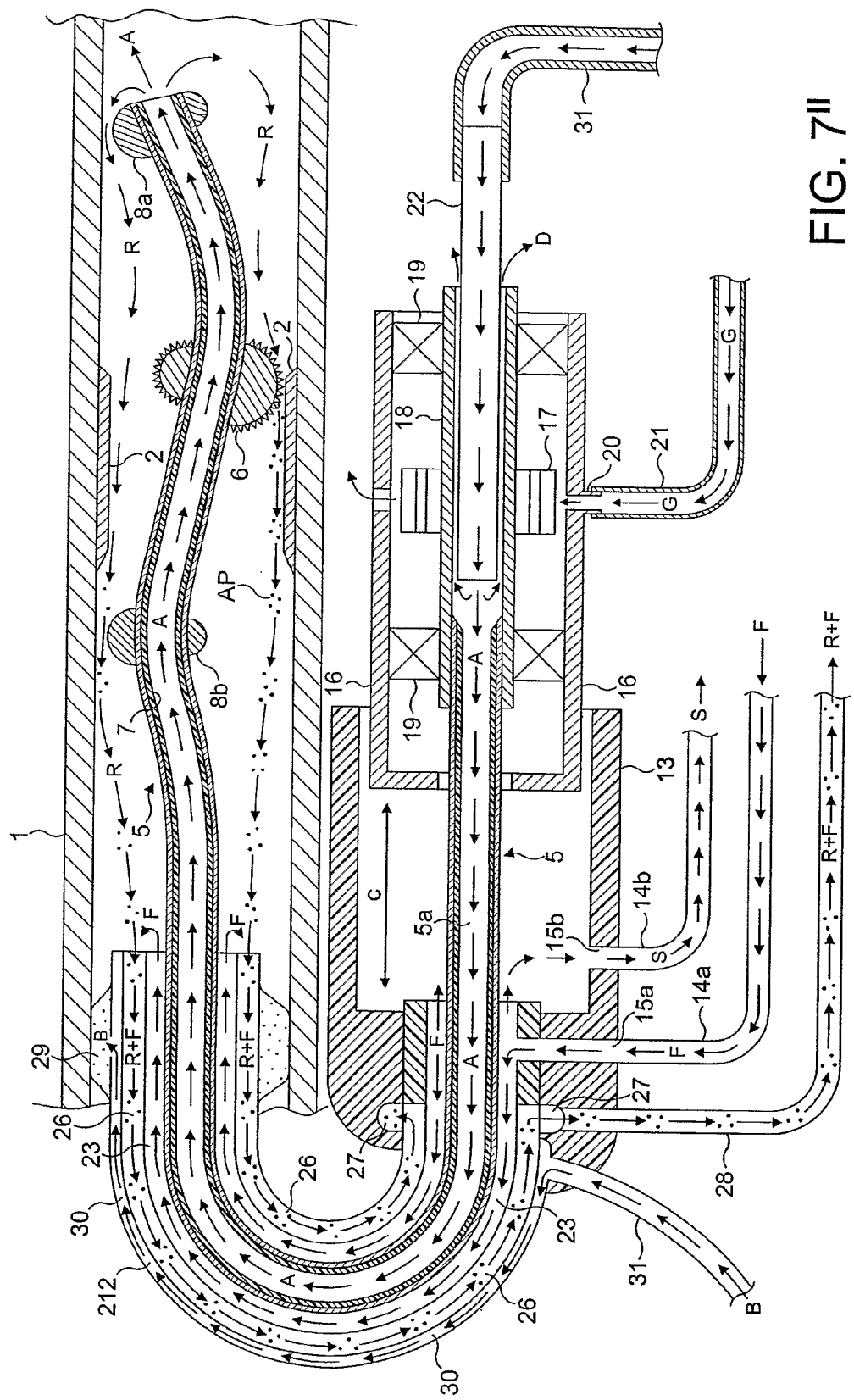
FIG. 7"

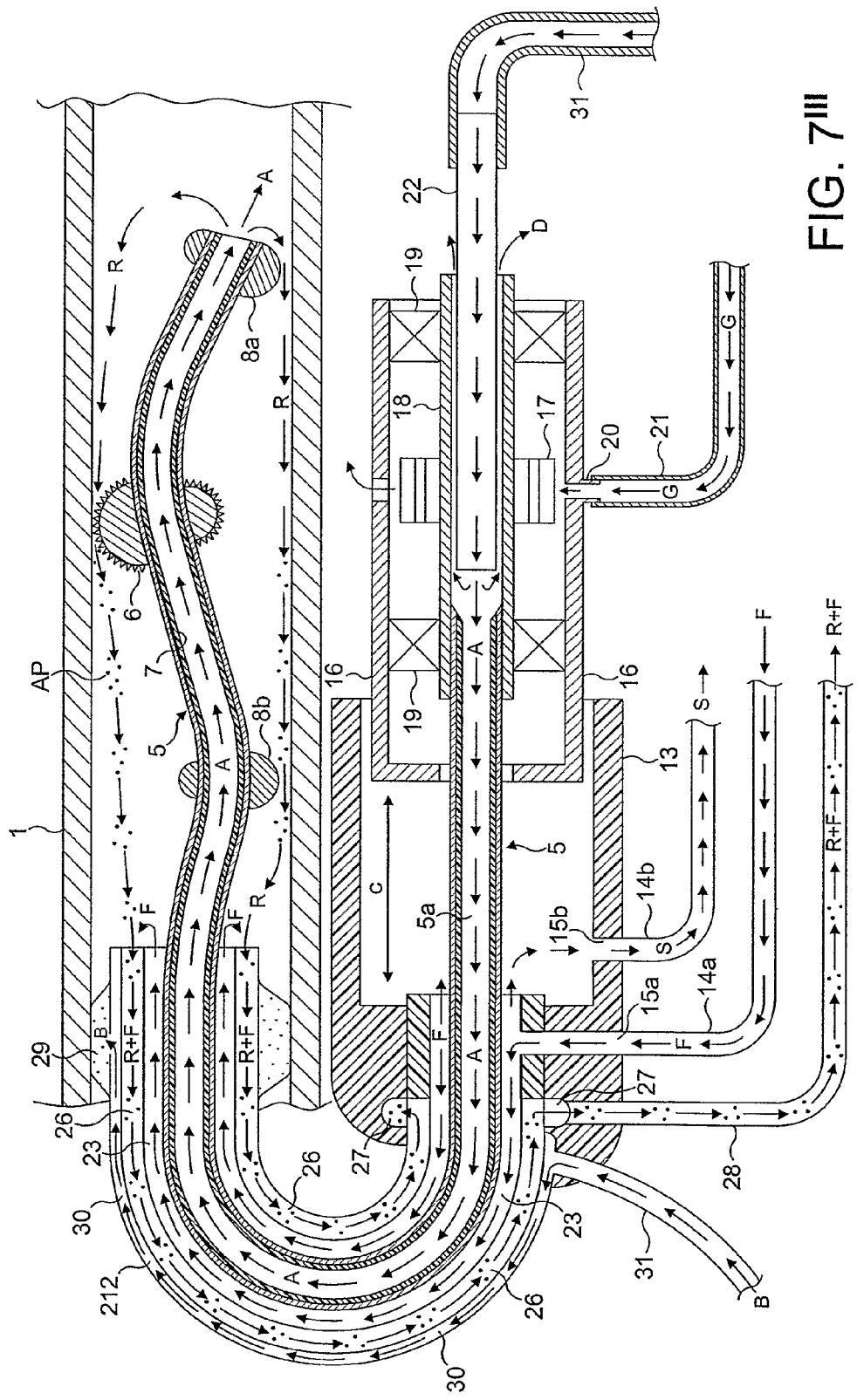
FIG. 7III

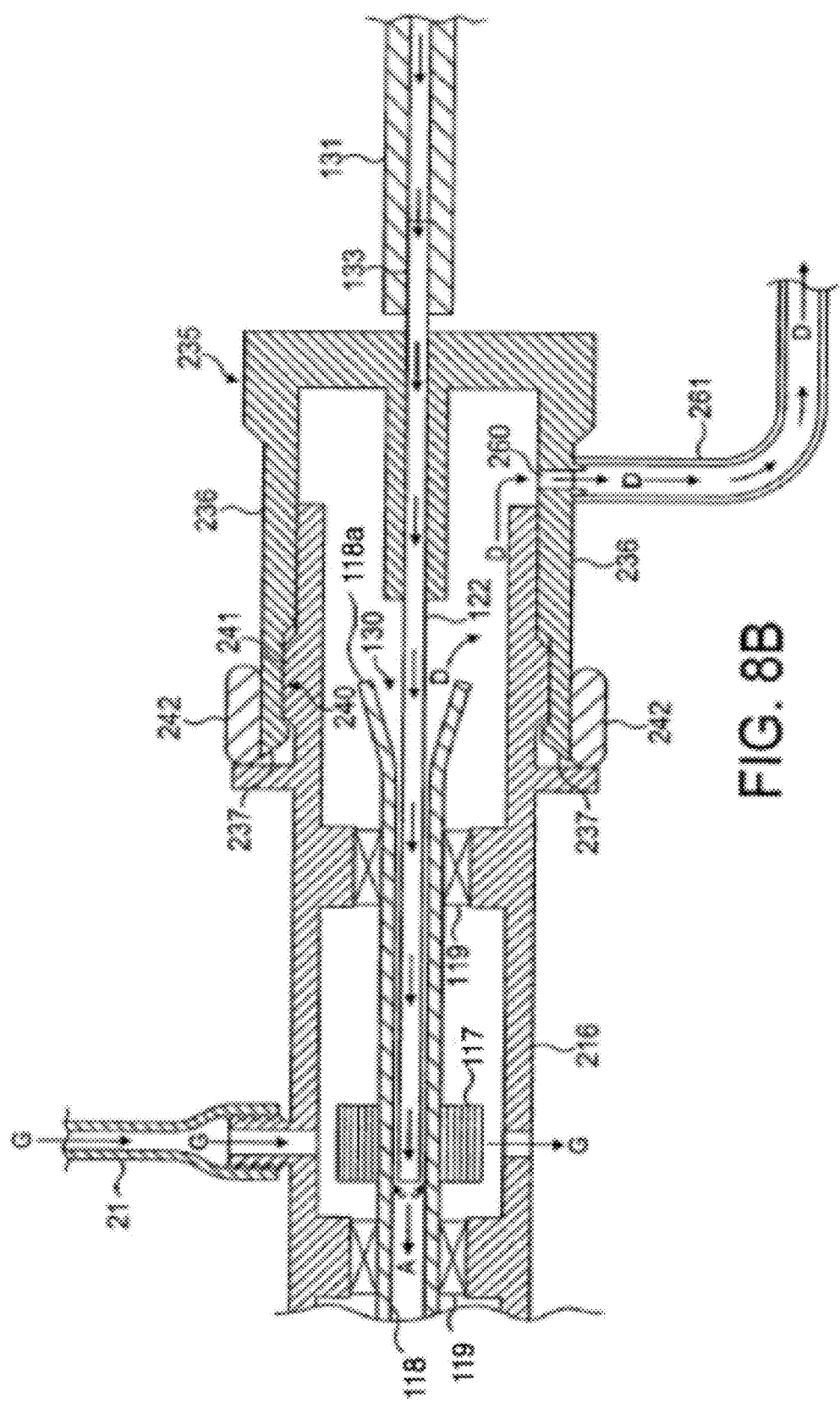

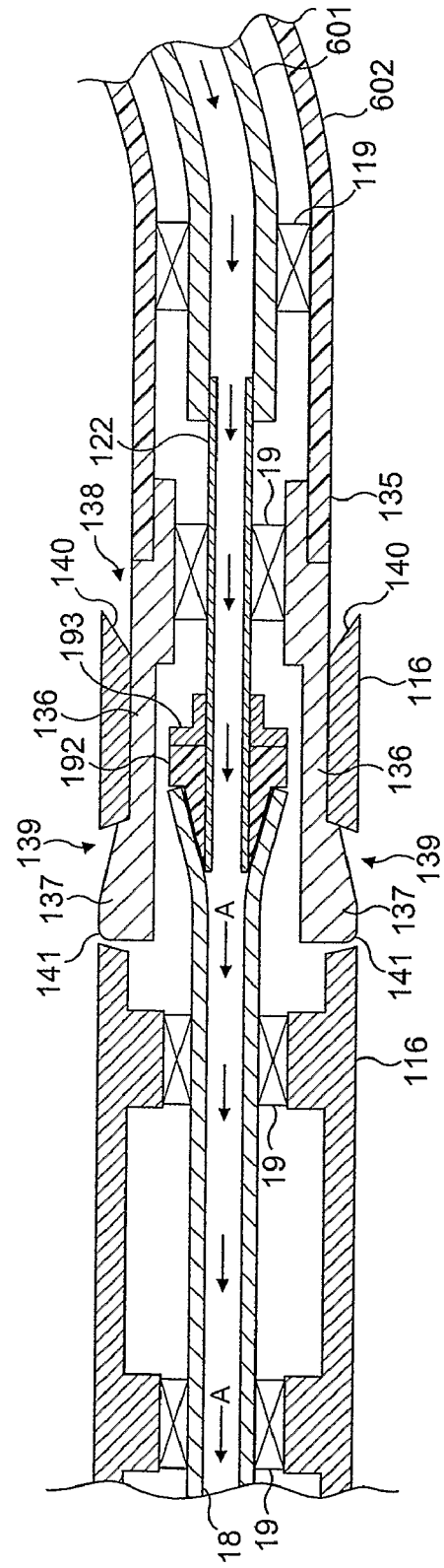

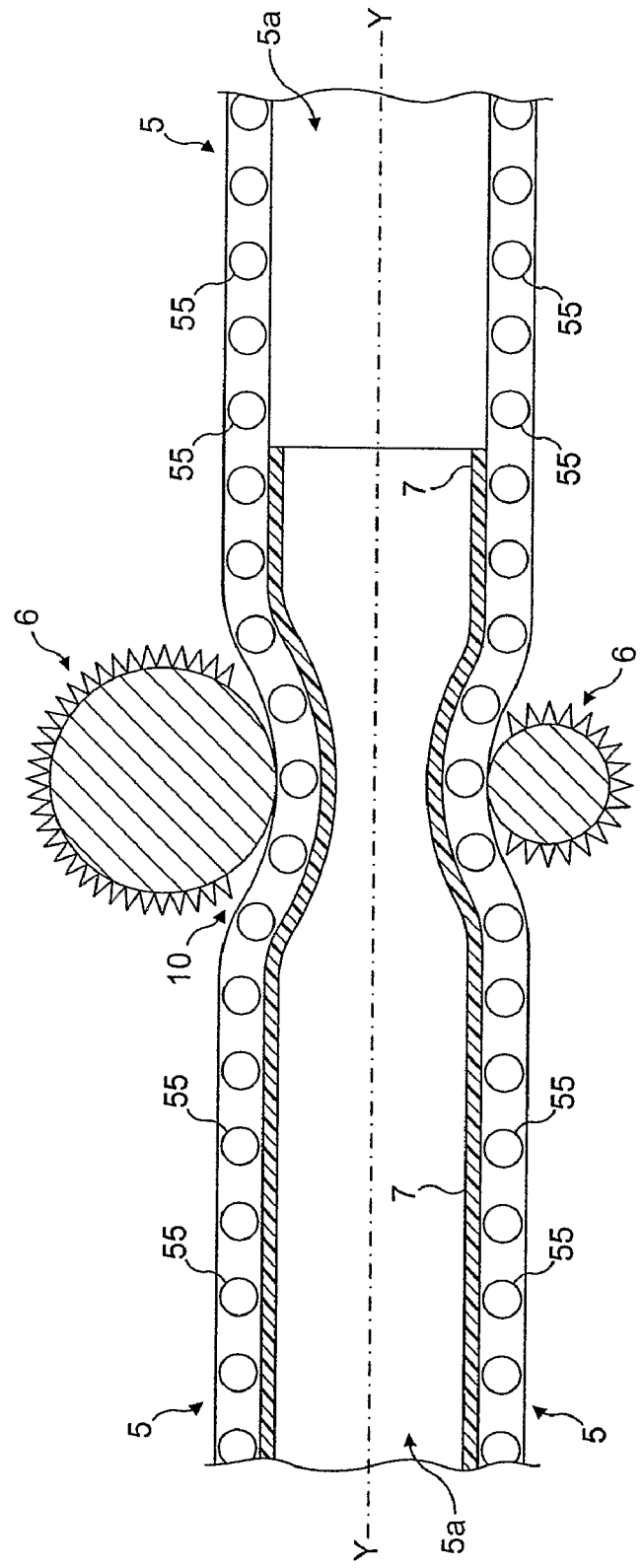

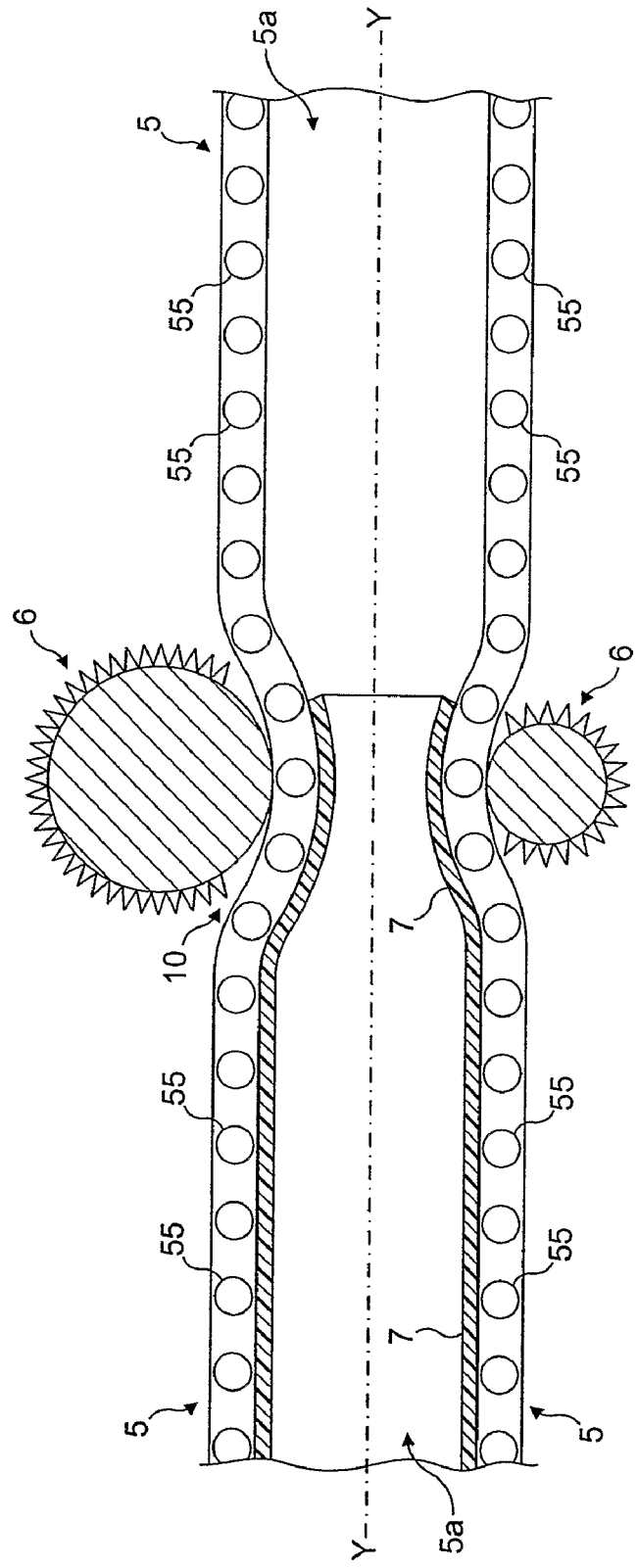

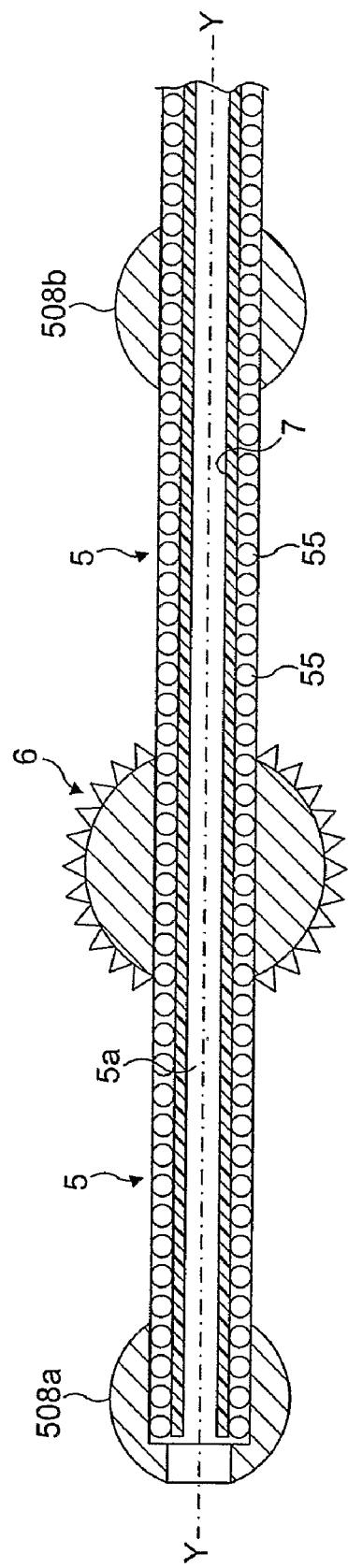

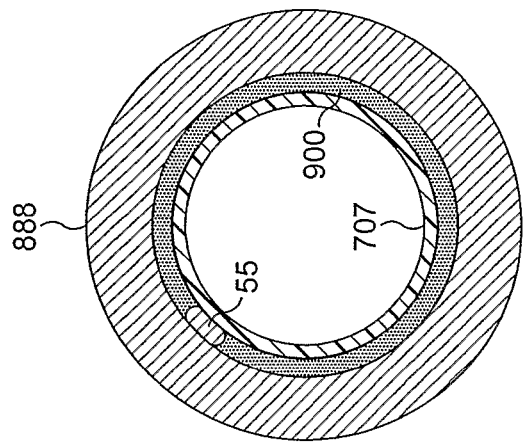
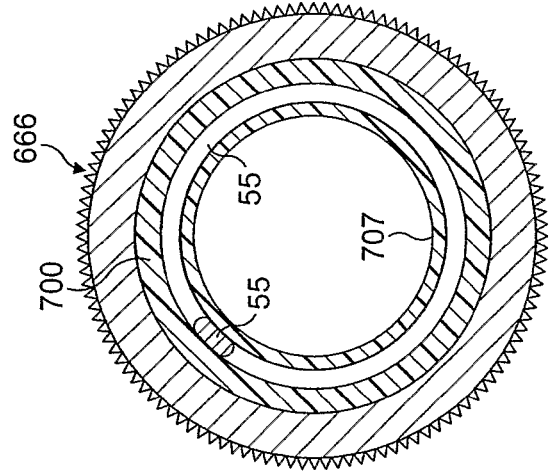
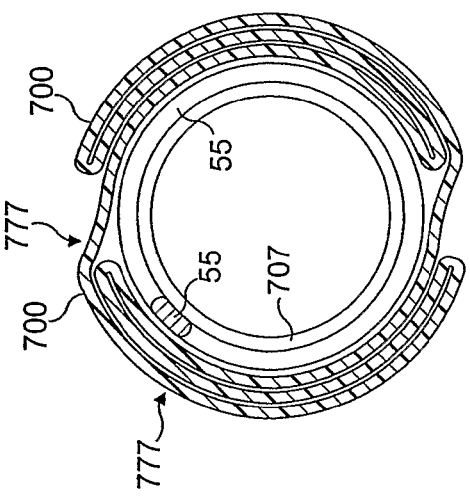

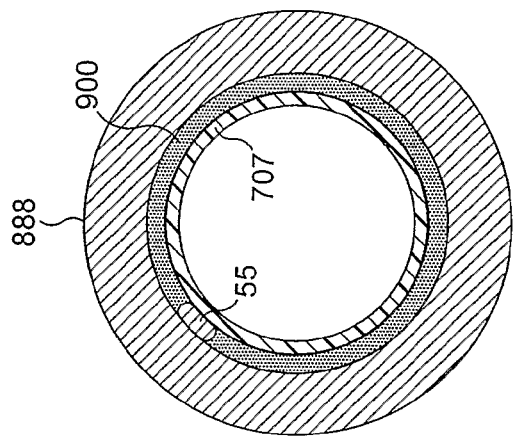
FIG. 18B^III
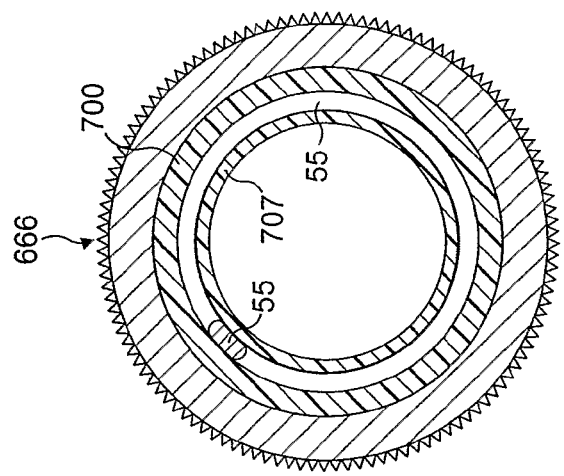
FIG. 18B^II
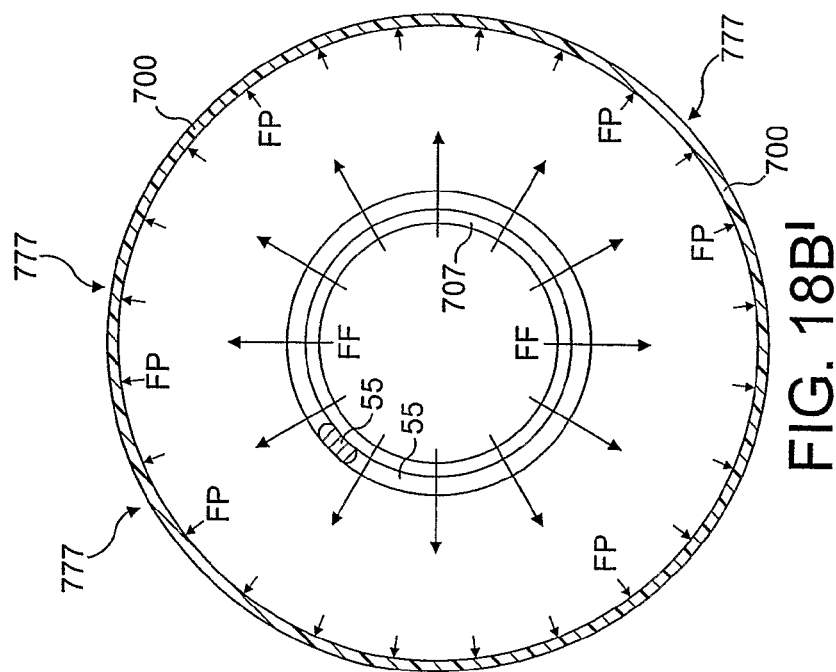
FIG. 18B^I

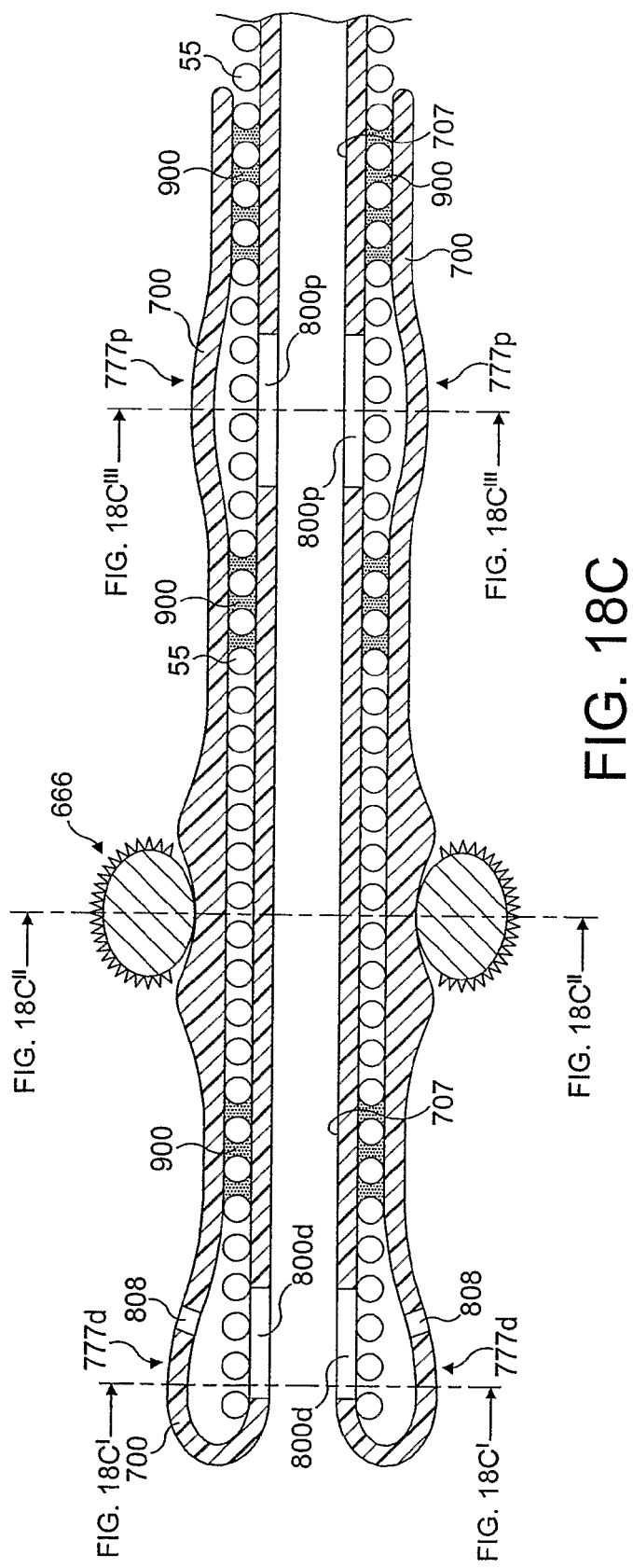

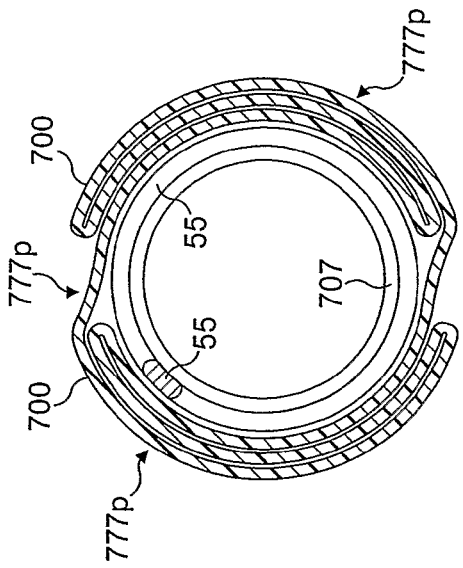
FIG. 18C^III
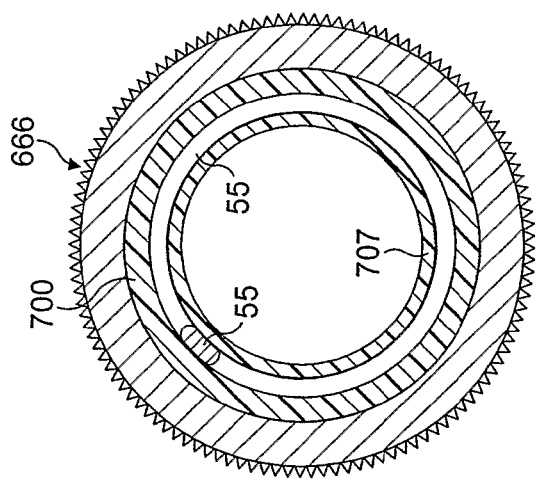
FIG. 18C^II
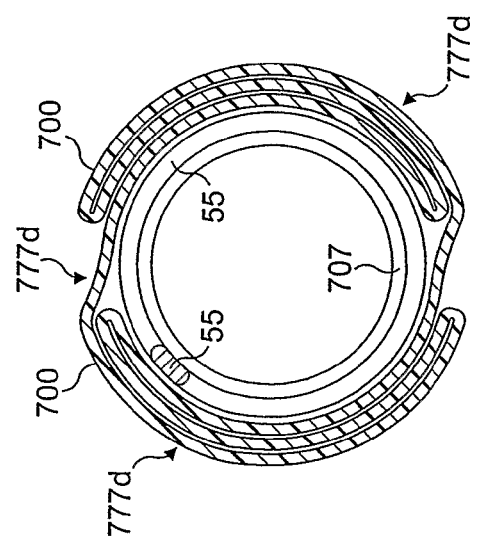
FIG. 18C^I

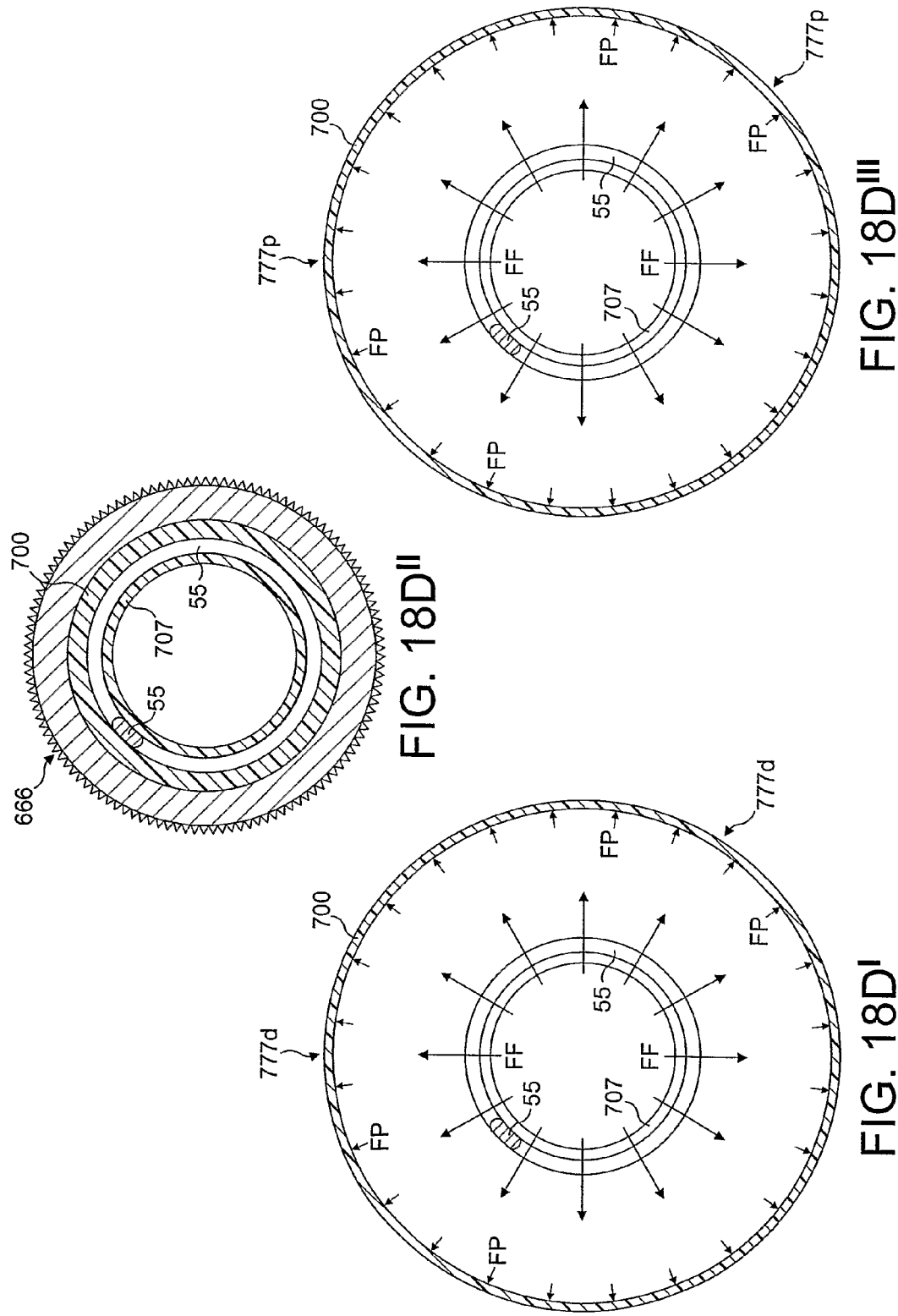

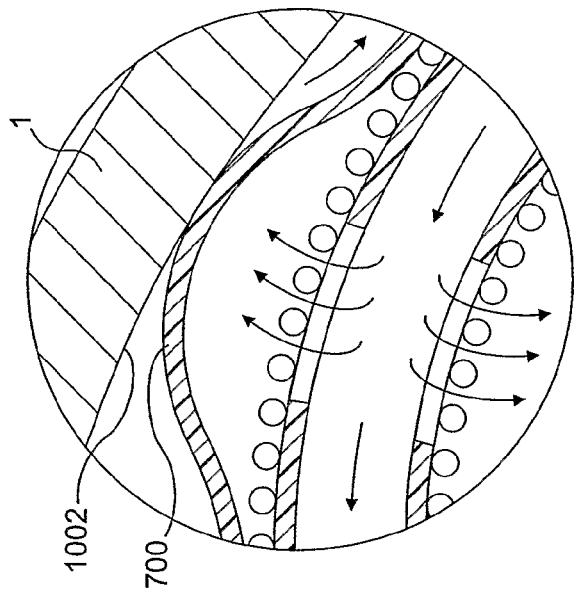
FIG. 18E^III
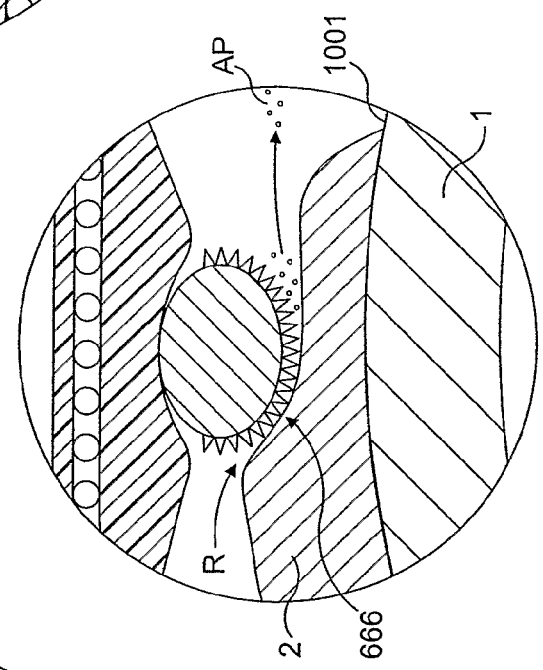
FIG. 18E^II
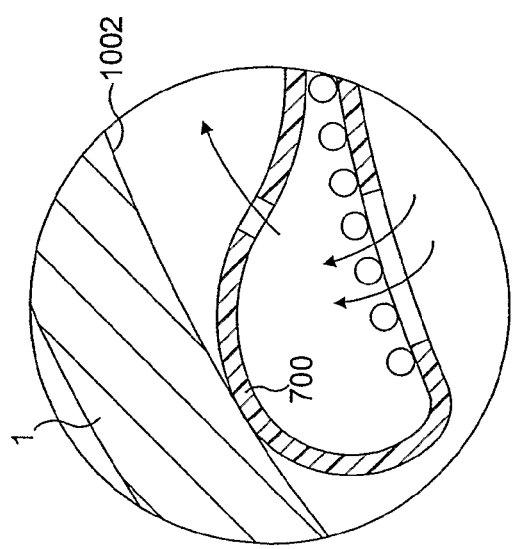
FIG. 18E^I

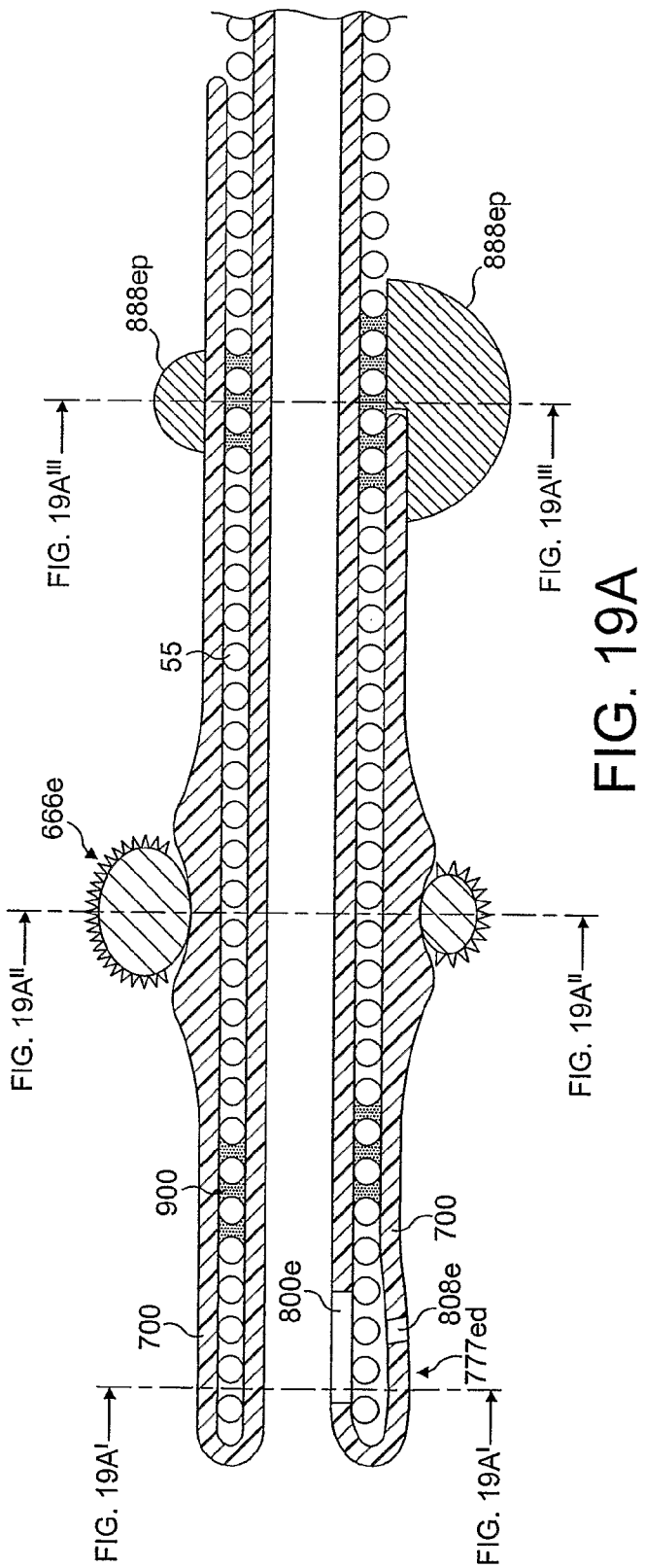

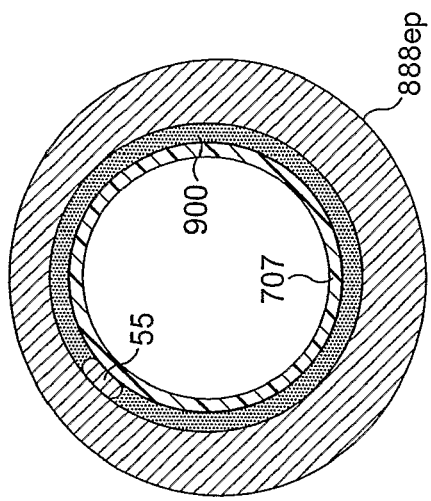
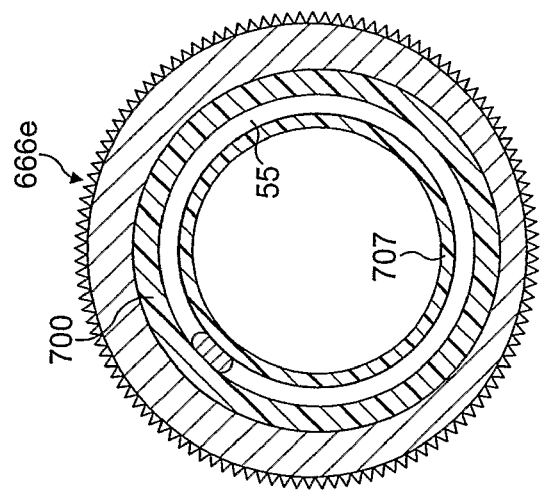
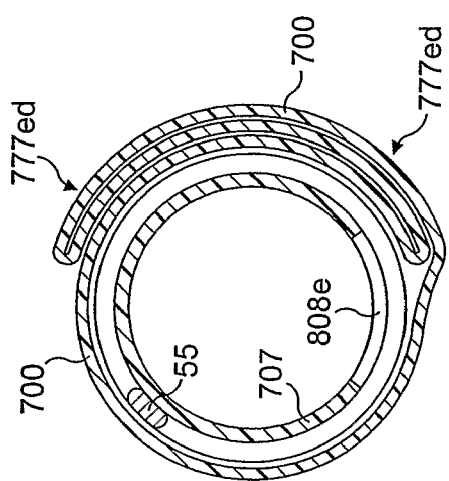

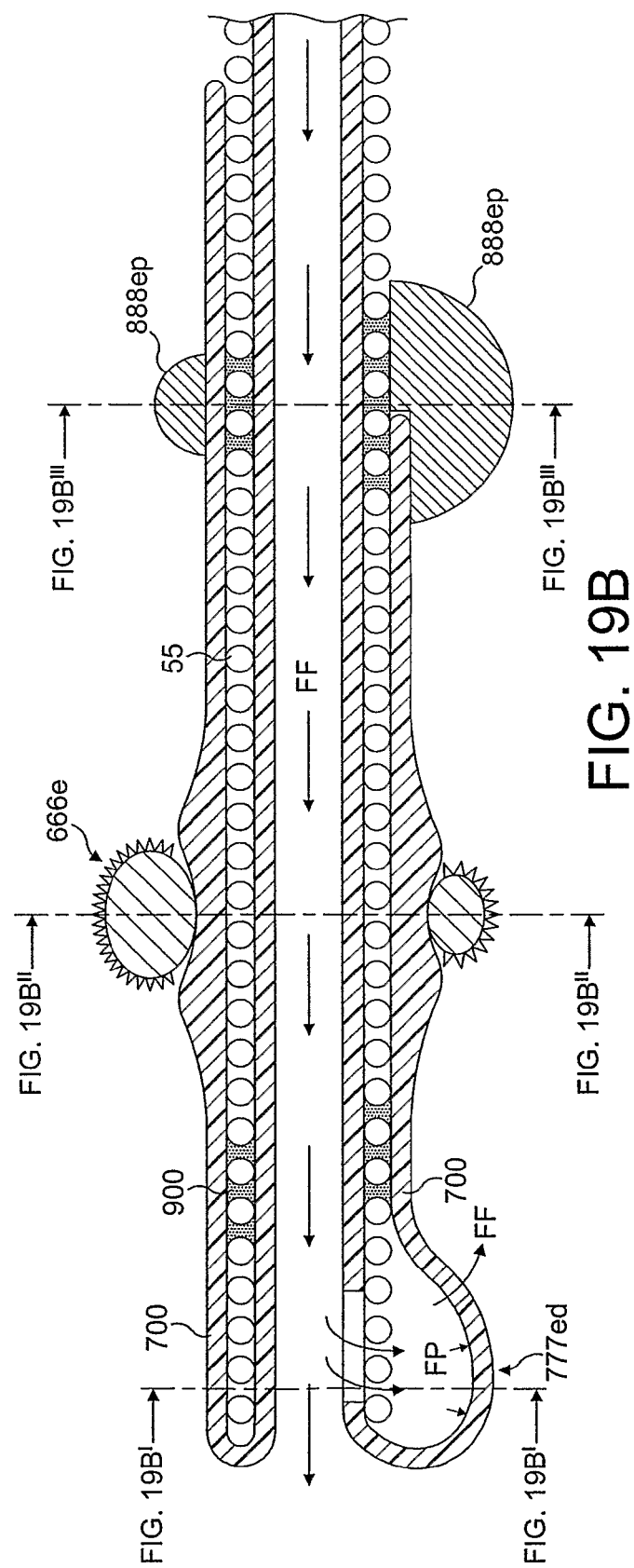

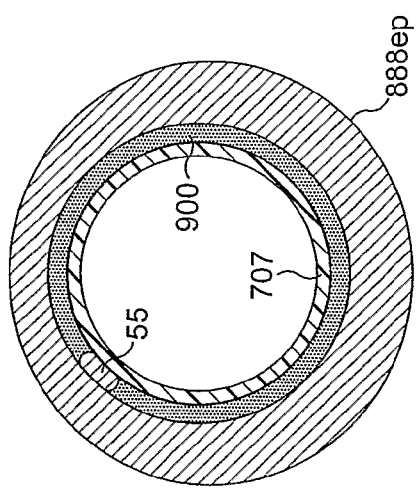
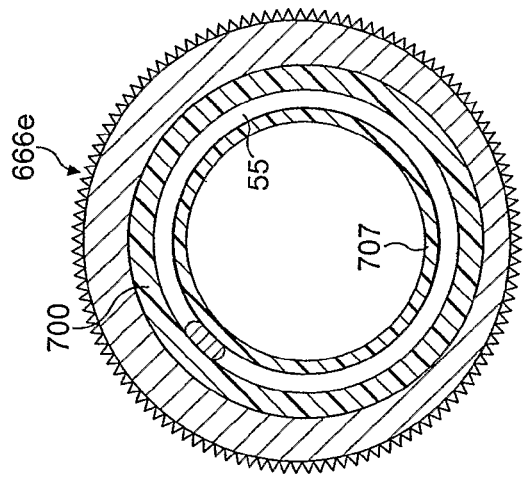
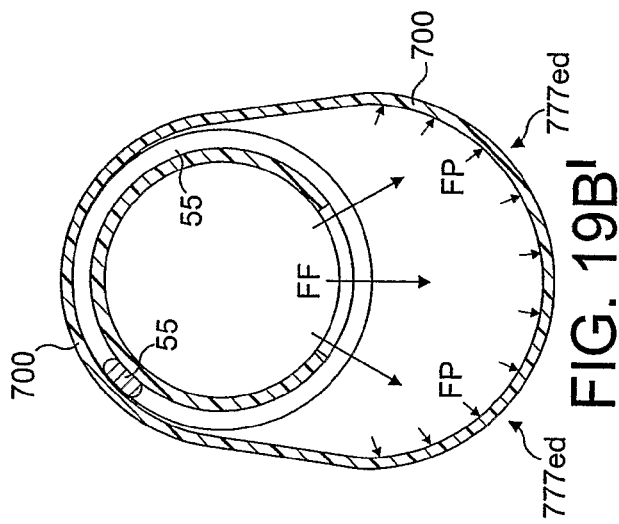
FIG. 19B^I   FIG. 19B^II   FIG. 19B^III

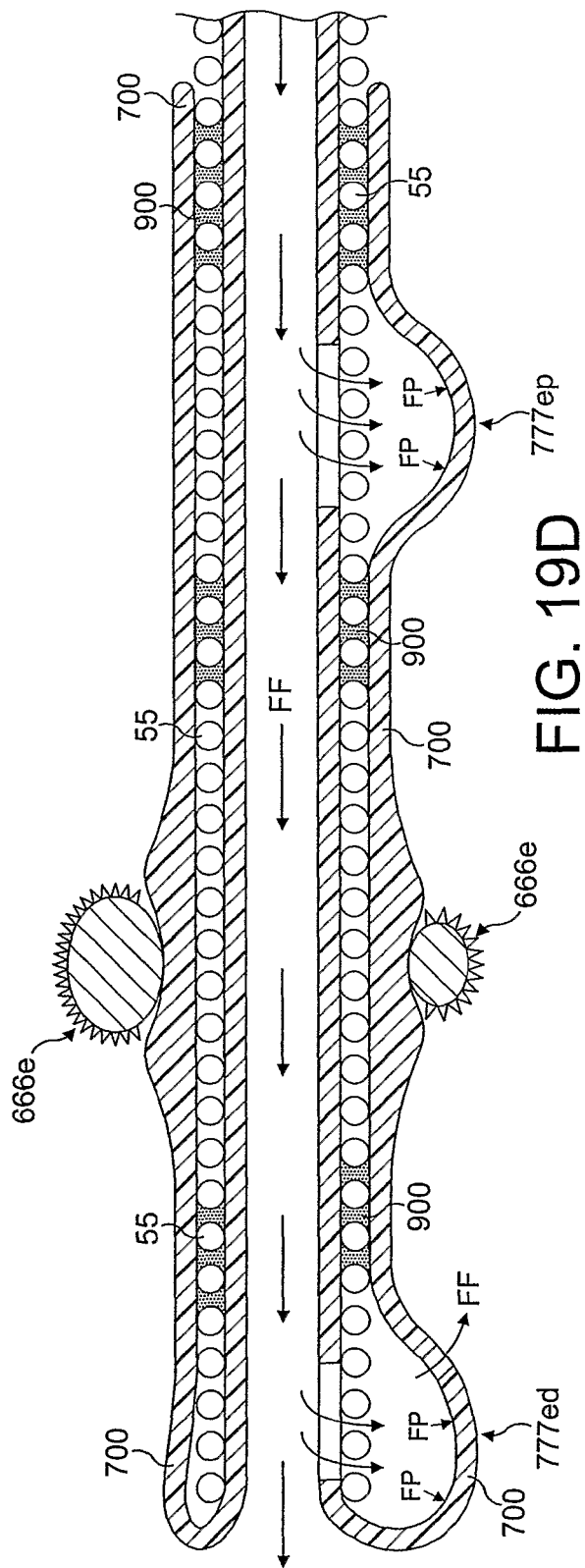

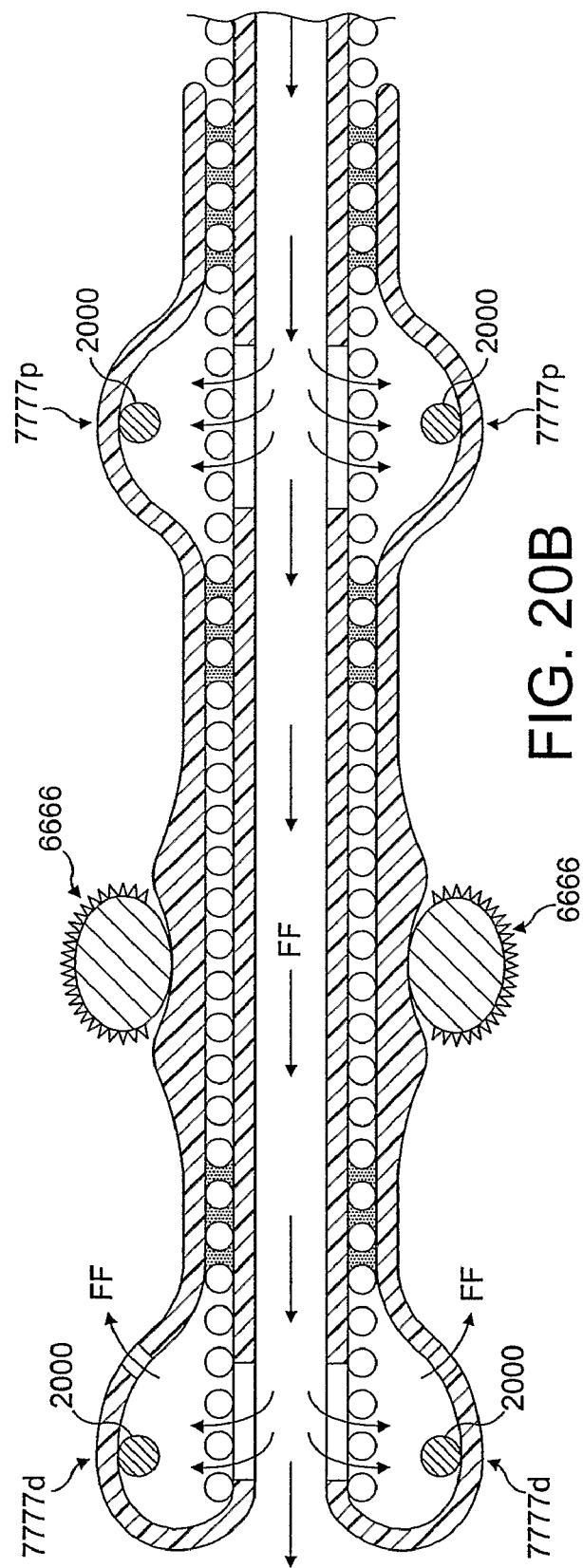

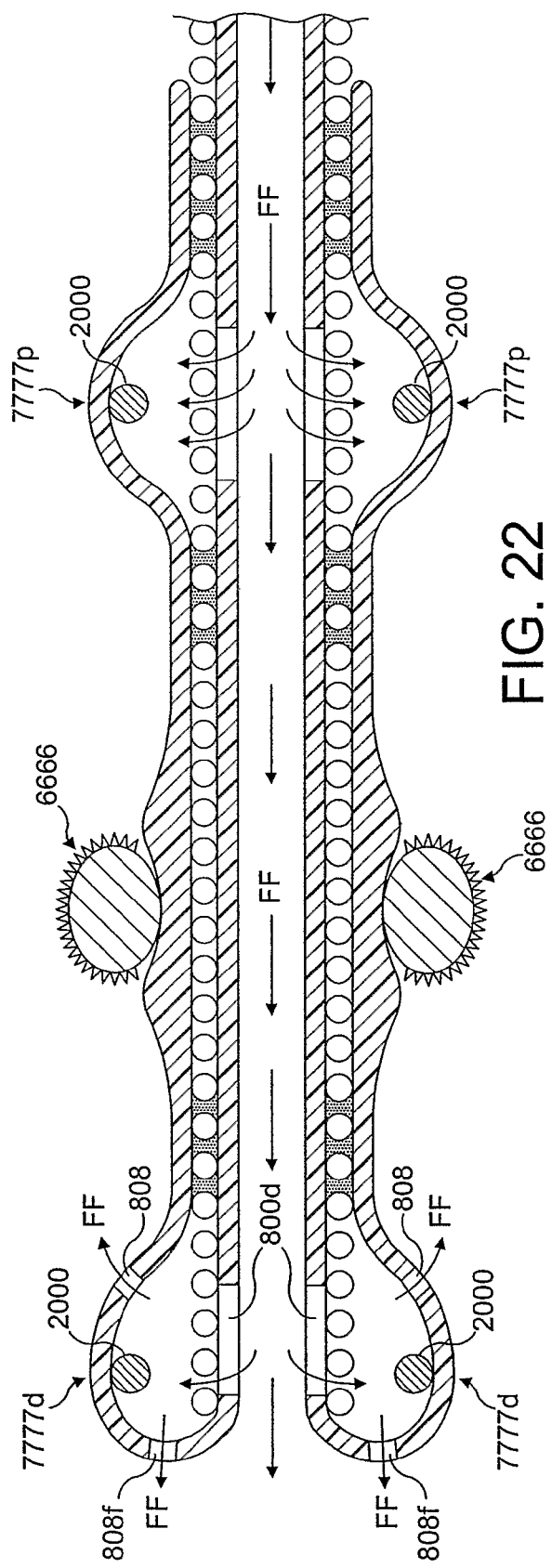

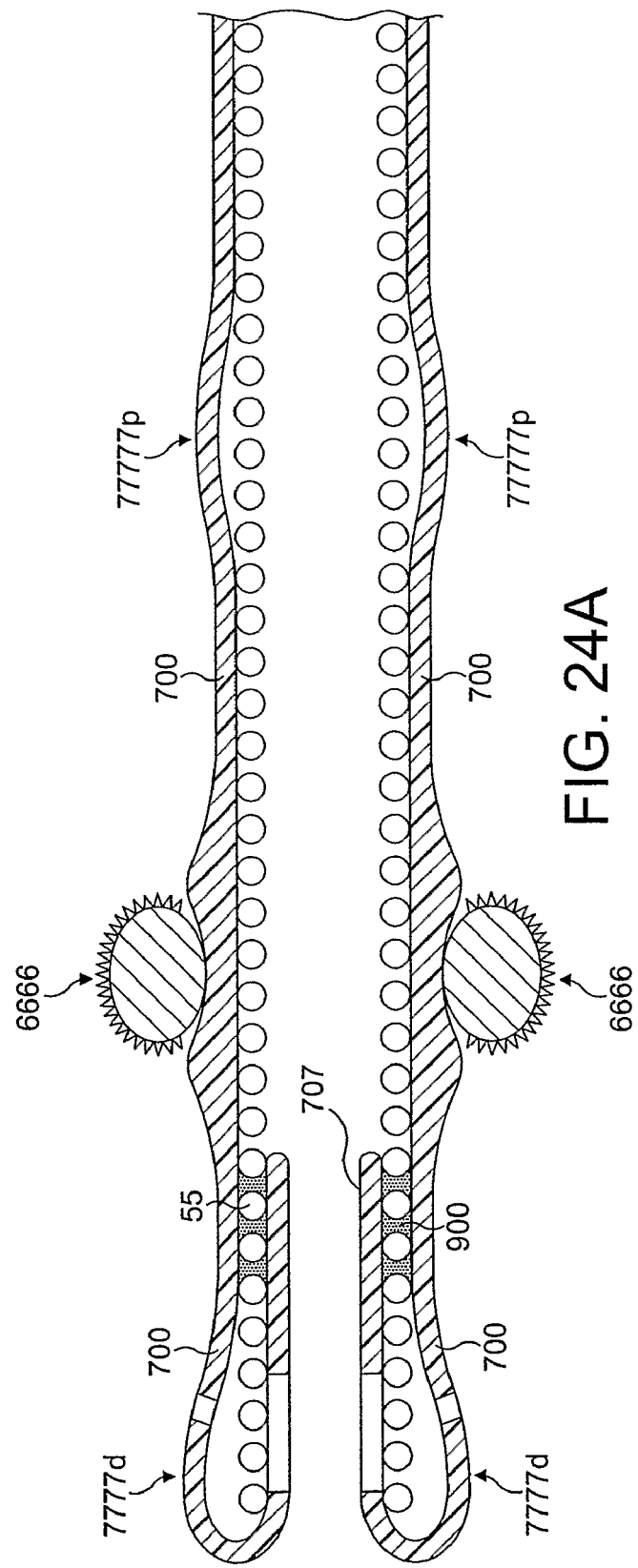

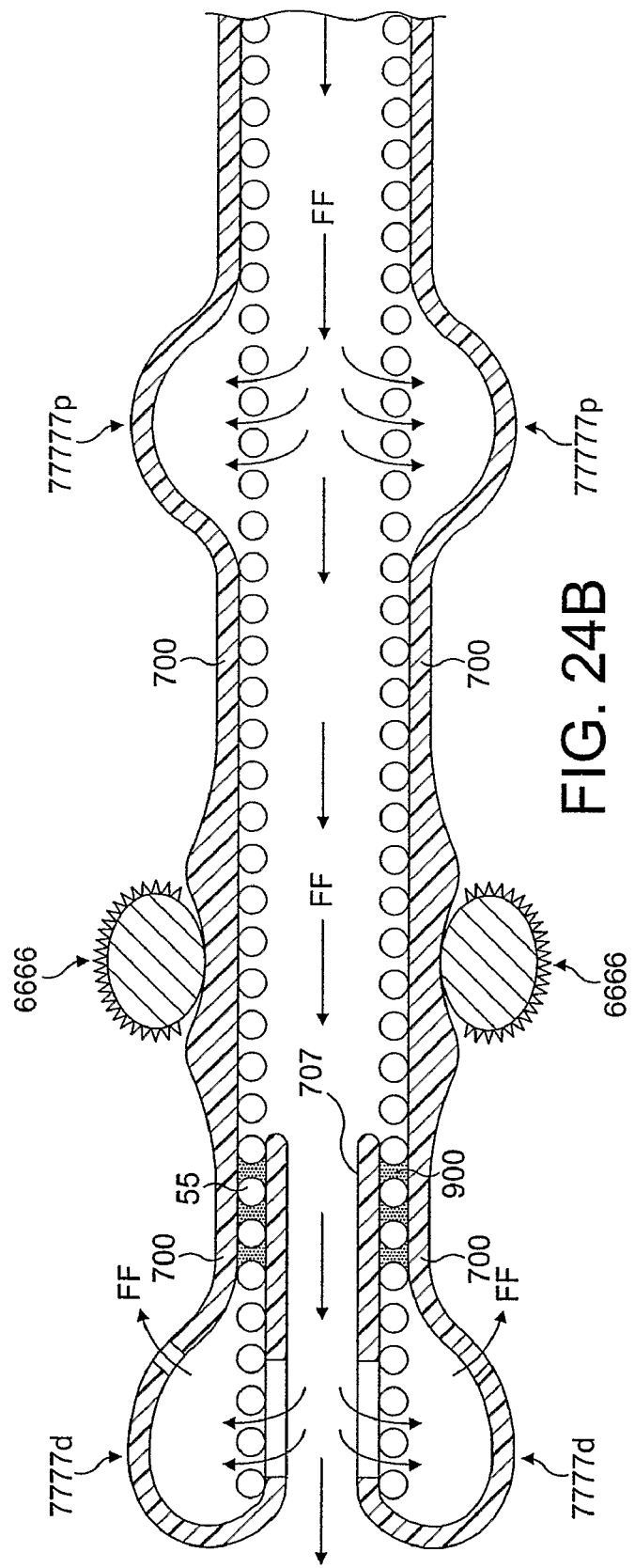

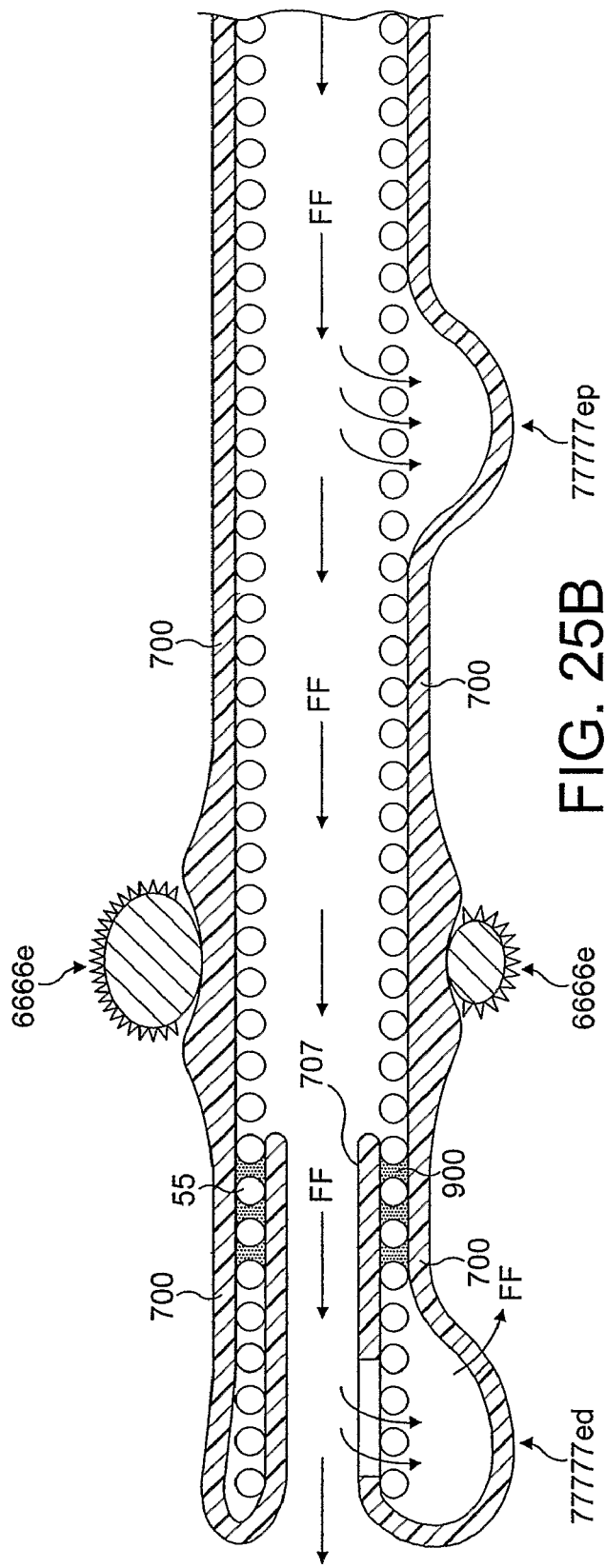

ROTATIONAL ATHERECTOMY DEVICE WITH DISTAL PROTECTION CAPABILITY AND METHOD OF USE

CROSS-REFERENCE TO RELATED APPLICATIONS

The present application claims the benefit of and priority to International Application No. PCT/IB2006/001368 filed on May 25, 2006 claiming priority from British Patent Application No. 0510802.5 filed on May 26, 2005, the entire contents of each of which are incorporated herein by reference.

The invention relates to a device for removing material from the interior of a vessel. More specifically, the invention relates to a rotational atherectomy device for removing or reducing stenotic lesions in blood vessels such as a human artery by rotating an abrasive element within the vessel to partially or completely ablate the unwanted material.

Atherosclerosis, the clogging of arteries, is a leading cause of coronary heart disease. Blood flow through the peripheral arteries (e.g., carotid, femoral, renal, etc.), is similarly affected by the development of atherosclerotic blockages. A conventional method of removing or reducing blockages in blood vessels is known as rotational atherectomy. A long guidewire is advanced into the diseased blood vessel and across the stenotic lesion. A hollow drive shaft is then advanced over the guidewire. The distal end of the drive shaft terminates in a burr provided with an abrasive surface formed from diamond grit or diamond particles. The burr is positioned against the occlusion and the drive shaft rotated at extremely high speeds (e.g., 20,000-160,000 rpm). As the burr rotates, the physician slowly advances it so that the abrasive surface of the burr scrapes against the occluding tissue and disintegrates it, reducing the occlusion and improving the blood flow through the vessel. Such a method and a device for performing the method are described in, for example, U.S. Pat. No. 4,990,134 to Auth. It is also known from U.S. Pat. No. 6,132,444 to Shturman (the instant inventor) et al., to provide a drive shaft with an abrasive element eccentrically positioned proximally to and spaced away from the distal end of the drive shaft.

Rotational angioplasty (atherectomy) is frequently used to remove atherosclerotic or other blocking material from stenotic (blocked) coronary arteries and other blood vessels. However, a disadvantage with this technique is that abraded particles can migrate along the blood vessel distally and block very small diameter vessels including capillaries of the heart muscle itself. The effect of the particulate debris produced by this procedure is of major concern to physicians who practice in this field. Clearly, the existence of particulate matter in the blood stream is undesirable and can cause potentially life-threatening complications, especially if the particles are over a certain size.

Although the potentially detrimental effect caused by the presence of abraded particles in the blood vessels is reduced if they are very small microparticles, it is much more preferable to remove from the treated blood vessel any debris abraded or otherwise released from the stenotic lesion during treatment and thereby prevent migration of debris to other locations along the treated blood vessel.

A rotational atherectomy device, described in U.S. Pat. No. 5,681,336 (to Clement et al.), has been proposed which attempts to prevent migration of abraded particles along the blood stream by removing the ablated material from the blood vessel whilst the device is in use. This device includes a balloon mounted close to the distal end of a hollow guidewire that is advanced into the treated vessel so that the guidewire balloon is located distal to the stenotic lesion. The guidewire balloon is then inflated via a lumen extending through the hollow guidewire so that abraded debris produced by the rotating burr is prevented from travelling in a distal direction along the vessel by the balloon located dose to the distal end of the guidewire. A suction device removes the ablated material through an annular space between a drive shaft and a sheath surrounding the drive shaft. In one modified embodiment of the device disclosed in this document, a balloon cuff surrounds the distal end of a modified guide catheter to enable the treatment site to be isolated from the rest of the circulatory system distally by the balloon of the hollow guidewire and proximally by the balloon cuff at the distal end of the modified guide catheter.

The rotational atherectomy device known from U.S. Pat. No. 5,681,336 (to Clement et al.) has a complicated construction and is difficult to manufacture on a commercial scale. Notably, it is very difficult to make a hollow flexible guidewire combining both a sufficiently small diameter to facilitate its passage through the narrow coronary arteries and, a strength sufficient to prevent its breakage due to metal fatigue which develops in the guidewire during very rapid rotation of the flexible hollow drive shaft around the guidewire.

The present invention seeks to provide a rotational device that overcomes or substantially alleviates the problems associated with the prior art and other disadvantages associated with known atherectomy devices of this type.

SUMMARY

According to one embodiment of the present invention, there is provided a rotational atherectomy device for removing a stenotic lesion from within a vessel of a patient, the device comprising a rotatable, flexible, hollow, fluid impermeable drive shaft having an abrasive element located on the drive shaft proximal to its distal end and rotatable together with the drive shaft, the fluid impermeable drive shaft being insertable into the vessel to be treated to enable flushing fluid to be pumped into the fluid impermeable drive shaft through its proximal end portion in an antegrade direction, the flushing fluid flowing along the fluid impermeable drive shaft and entering the vessel to be treated through at least one luminal opening located distally to the abrasive element so that, upon entering the vessel distal to the abrasive element, said flushing fluid develops such fluid pressure in the vessel located distal to the abrasive element which is sufficient to generate a retrograde flow of at least a portion of the flushing fluid around the abrasive element and the fluid impermeable drive shaft for removal from the treated vessel debris abraded by the rotating abrasive element during rotation of the drive shaft and entrained in the retrograde flowing flushing fluid.

According to a preferred embodiment of the invention, the device comprises a rotatable, flexible, hollow, fluid impermeable drive shaft which may be advanced into shaft proximal to its distal end to abrade a stenotic lesion when the drive shaft rotates, wherein the flexible, hollow, fluid impermeable drive shaft has a fluid impermeable drive shaft lumen for pumping pressurised flushing fluid in an antegrade direction therealong into the vessel through at least one luminal opening located distal to the abrasive element so that at least a portion of said pressurised flushing fluid entering the vessel distal to the abrasive element through the or each luminal opening flows in a retrograde direction around the abrasive element and the fluid impermeable drive shaft to entrain debris abraded by the rotating abrasive element for removal of said debris from the treated vessel.

According to a preferred embodiment of the invention, the abrasive element which is located on the fluid impermeable drive shaft proximal to its distal end is also spaced away from the distal end of the drive shaft. In one preferred embodiment of the invention, the abrasive element is spaced away from the distal end of the drive shaft by a distance not less than about 1 mm and not more than about 60 mm. In the most preferred embodiment of the invention, the abrasive element is spaced away from the distal end of the drive shaft by a distance not less than about 3 mm and not more than about 30 mm.

According to a preferred embodiment of the invention, the pressurised flushing fluid is pumped along the fluid impermeable drive shaft lumen and into the vessel through the or each luminal opening located distal to the abrasive element at a fluid flow rate that generates a fluid pressure gradient between a region distal to the abrasive element and a region proximal to the abrasive element thereby causing at least a portion of the pressurised flushing fluid entering the vessel to flow in a retrograde direction around the abrasive element and the drive shaft to entrain debris abraded by the rotating abrasive element for removal of said debris from the treated vessel.

In a preferred embodiment of the invention, flushing fluid is pumped in an antegrade direction into a proximal end of the fluid impermeable drive shaft, the flushing fluid entering the proximal end of the drive shaft along an axis which is coaxial with the longitudinal axis of the proximal end portion of the drive shaft.

According to one embodiment of the present invention, the rotational atherectomy device includes a drive shaft sheath that extends around the drive shaft and terminates proximal to the abrasive element, the sheath having an inner diameter larger than the outer diameter of the drive shaft so as to define an annular lumen around the fluid impermeable drive shaft so that the flushing fluid together with debris entrained in the flushing fluid, that has flowed in a retrograde direction around the abrasive element and the fluid impermeable drive shaft, flows into the annular lumen defined by the sheath for removal of said debris from the treated vessel.

The annular lumen between the drive shaft and the sheath may be in communication with a suction device operable to assist or cause retrograde flow of fluid and debris along the annular lumen for subsequent removal from the patient.

According to another embodiment of the present invention, the rotational atherectomy device includes a drive shaft sheath that extends around the fluid impermeable drive shaft and terminates proximal to the abrasive element, the sheath having an inner diameter larger than the outer diameter of the fluid impermeable drive shaft so as to define an annular lumen around the fluid impermeable drive shaft along which flushing fluid is pumped initially in an antegrade direction in addition to the flushing fluid to be pumped along the lumen of the fluid impermeable drive shaft to enable flushing fluid to rapidly flood a vessel to be treated before initiating rotation of the drive shaft and reversing a direction of fluid flow along the annular lumen from the antegrade to a retrograde direction just prior to or shortly after rotation of the drive shaft has been initiated, so that the flushing fluid from the fluid impermeable drive shaft lumen, which has flowed in the retrograde direction around the abrasive element together with debris entrained in this fluid flows into the annular lumen defined by the sheath for removal of said debris from the treated vessel.

According to yet another embodiment, the rotational atherectomy device includes a modified drive shaft sheath that extends around the fluid impermeable drive shaft and terminates proximal to the abrasive element, the sheath having an inner diameter larger than the outer diameter of the fluid impermeable drive shaft so as to define an annular lumen around the fluid impermeable drive shaft, the modified drive shaft sheath including at least one additional discrete lumen which is separate to the annular lumen through which the drive shaft extends so that flushing fluid may be pumped in an antegrade direction along the annular lumen defined by the sheath in addition to pumping flushing fluid along a lumen of the fluid impermeable drive shaft, both the flushing fluid from the annular lumen defined by the sheath and the flushing fluid from the fluid impermeable drive shaft lumen which has flowed in a retrograde direction around the abrasive element together with debris entrained in this fluid being directed into the, or each, additional discrete lumen in this multi-lumen drive shaft sheath for subsequent removal from the treated vessel.

Advantageously, the flushing fluid, which may be pumped in an antegrade direction through the annular lumen defined by the sheath lubricates the drive shaft as it rotates within the drive shaft sheath.

According to a modified embodiment of the invention, the multi-lumen drive shaft sheath includes at least one lumen along which fluid is allowed to flow in more than one direction, the flushing fluid being pumped initially in an antegrade direction along the or each lumen in the drive shaft sheath in addition to the flushing fluid pumped along the fluid impermeable drive shaft, to enable flushing fluid to rapidly flood a vessel to be treated before initiating rotation of the drive shaft and reversing a direction of fluid flow along both the annular lumen and the or each additional discrete lumen in the multi-lumen drive shaft sheath from the antegrade to the retrograde direction just prior to or shortly after rotation of the drive shaft has been initiated, so that flushing fluid from the fluid impermeable drive shaft lumen, which has flowed in a retrograde direction around the abrasive element together with debris entrained in this fluid flows into both the annular lumen and the or each additional discrete lumen of the multi-lumen drive shaft sheath for removal of said debris from the treated vessel.

According to yet another modified embodiment of the invention, the multi-lumen drive shaft sheath includes at least one lumen along which fluid is allowed to flow in more than one direction, the flushing fluid being pumped initially in an antegrade direction along the or each lumen in the drive shaft sheath in addition to the flushing fluid pumped along the fluid impermeable drive shaft, to enable flushing fluid to rapidly flood a vessel to be treated before initiating rotation of the drive shaft and, just prior to or shortly after rotation of the drive shaft has been initiated, substantially reducing the antegrade flow of flushing fluid along the annular lumen of the drive shaft sheath and a reversing direction of fluid flow along the or each additional discrete lumen in the multi-lumen drive shaft sheath from the antegrade to the retrograde direction, so that flushing fluid from the fluid impermeable drive shaft lumen, which has flowed in a retrograde direction around the abrasive element together with debris entrained in this fluid flows into the or each additional discrete lumen of the multi-lumen drive shaft sheath for removal of said debris from the treated vessel.

In one embodiment of the invention, the annular lumen formed between the drive shaft and the sheath may be in communication with at least one fluid moving device, the or each fluid moving device being operable to move fluid along the annular lumen in at least one direction.

The or each lumen of the fluid impermeable drive shaft sheath which is separate to the annular lumen between the drive shaft and the sheath may also be in communication with at least one fluid moving device, the or each fluid moving device being operable to move fluid along said separate lumen(s) in at least one direction.

A peristaltic pump or pumps may be utilised to move fluids in both antegrade and retrograde directions along the or each lumen of the drive shaft sheath.

The device comprising a multi-lumen drive shaft sheath preferably includes means for controlling the pressure of the flushing fluid pumped in the antegrade direction along the annular lumen around the driver shaft sheath relative to the pressure of the flushing fluid pumped along the fluid impermeable drive shaft so that, just prior to or shortly after initiating rotation of the drive shaft, pressure of the flushing entering the vessel from the annular lumen is reduced to a level at which a fluid pressure gradient is generated within the treated vessel between a region distal to the abrasive element and a region around a distal end of the drive shaft sheath so that any flushing fluid which enters the vessel from the annular lumen of the sheath is forced by the fluid pressure gradient to enter the or each separate lumen(s) in the sheath and flow in a retrograde direction along at least one such separate lumen together with the flushing fluid which has flowed in a retrograde direction around the abrasive element.

The above described modified embodiment of the drive shaft sheath with both an annular lumen around the drive shaft and at least one additional discrete lumen, may become impractical for use in smaller diameter coronary arteries due to an unacceptable increase in diameter of such a multi-lumen drive shaft sheath.

The flushing fluid may comprise saline solution, X-ray contrast solution or any other suitable solution or mixture thereof. In some applications even oxygenated blood or other oxygen carrying solution may be used as a flushing fluid.

In yet another embodiment of the invention, the rotational atherectomy device preferably comprises an inflatable element on the drive shaft sheath which, when partially inflated within the vessel, reduces the antegrade flow of blood around the inflatable element of the sheath. Consequently, the amount of flushing fluid that needs to be supplied through the drive shaft lumen to achieve retrograde flow of fluid over the abrasive element is reduced.

The inflatable element on the drive shaft sheath may be inflated to a point at which it contacts the vessel wall and locates the drive shaft sheath in the vessel so that the inflatable element prevents both the antegrade flow of blood and the retrograde flow of the flushing fluid around the inflatable element of the sheath.

In one embodiment, an inflation lumen may extend through the drive shaft sheath and communicate the inflatable element of the sheath with an inflation source located at or near the proximal end of the drive shaft sheath. The inflation source may be located remotely and connected to the inflation lumen at or near the proximal end of the drive shaft sheath.

In one embodiment, the inflatable element may be a balloon mounted adjacent to the distal end of the drive shaft sheath.

In another embodiment, the inflatable element comprises a flexible sleeve extending around the outside of the drive shaft sheath which forms a potentially inflatable annular space around the sheath. The sleeve has distal and proximal ends, the distal end is bonded to an outer surface of the drive shaft sheath near its distal end while the potentially inflatable annular space around the sheath is in communication with an inflation device at or near the proximal end of the sleeve so that said space between the sheath and the sleeve may be inflated to restrict or block the flow of fluids around the sleeve as well as locate the sheath within the vessel, depending on the degree of inflation of the sleeve.

In a preferable embodiment, the sleeve is made from a stretchable material. However, the sleeve may also be made from a thin substantially non-stretchable material and be furled around the outside of the drive shaft sheath.

The inflation medium which is used to inflate the inflatable element of the sheath may be helium or other gas which is soluble in blood and which will not cause the formation of an embolism if it leaks into the vessel. Liquid X-ray contrast material or saline solution may alternatively be used. The use of a gaseous inflation medium which is soluble in blood is preferable because a capilliary effect is avoided and short inflation and deflation times are enabled.

At least that portion of the drive shaft which is proximal to the abrasive element and distal to a rigid, hollow, bearing supported shaft is fluid impermeable, thereby preventing flushing fluid pumped along the fluid impermeable drive shaft lumen from being transmitted through the wall of the drive shaft into a portion of the vessel which is located proximal to the abrasive element.

At least a portion of the drive shaft distal to the abrasive element may be fluid permeable so as to form said luminal openings and allow flushing fluid to flow out of the drive shaft lumen into the vessel through a portion of the drive shaft which is located distal to the abrasive element.

Alternatively, the whole of the drive shaft may be fluid impermeable, in which case the luminal opening is the opening at the distal end of the fluid impermeable drive shaft.

The fluid impermeable drive shaft may comprise a substantially fluid impervious membrane to prevent the transmission of fluid out from the lumen of the fluid impermeable drive shaft through a wall of the drive shaft.

The fluid impervious membrane may line the inside of the flexible, hollow drive shaft or, it may cover the outside of the drive shaft. In either case the fluid impervious membrane should extend at least along that portion of the flexible, hollow drive shaft which is proximal to the abrasive element.

In any of the above described embodiments, the fluid impervious membrane may terminate distally proximal to the distal end of the drive shaft but distal to the abrasive element or, it may terminate within the abrasive element.

The fluid impervious membrane may be formed from plastic tubing, silicon resin tubing or other suitable fluid impervious materials and can be applied to the drive shaft by any suitable method. For instance, the membrane may be applied to the drive shaft by heat-shrinking plastic tubing onto the outside of the drive shaft or by placing the drive shaft on a mandrel and immersing the drive shaft into a liquid material which forms the thin membrane on the shaft after removing the shaft from such liquid material. Alternatively, the membrane may comprise a non-stretchable flexible tube, said tube being applied to the drive shaft by stretching the drive shaft and inserting the stretched drive shaft into the tube before releasing the drive shaft. It will be appreciated that many other manufacturing techniques may be envisaged to enable manufacture of a fluid impermeable drive shaft.

In a preferred embodiment, the drive shaft is formed from at least one helically coiled wire and the fluid impervious membrane which prevents flow of fluid out from a lumen of the drive shaft between adjacent turns of said helically coiled wire. In this case, the fluid impervious membrane advantageously terminates distally proximal to the distal end of the drive shaft but distal to the abrasive element to allow the flow of fluid between adjacent turns of said helically coiled wire from the drive shaft lumen into a portion of the vessel which is located distal to the abrasive element. In this case, the luminal openings in the drive shaft are formed by the space or spaces between the turns of the coiled wire or wires through which fluid may pass from the drive shaft lumen into said portion of the vessel which is located distal to the abrasive element.

In one embodiment of the invention which is intended for use primarily in small diameter distal segments of coronary arteries, at least a distal portion of the drive shaft which is expected to enter the diseased vessel or section thereof may be made only from the fluid impermeable membrane, thereby allowing this distal portion of the drive shaft to be made very thin walled and of very small outer diameter. It is envisaged that said very small diameter distal portion of the drive shaft comprised only of the fluid impermeable membrane and a very small abrasive element mounted to or around the membrane may be introduced by the surgeon into the most distal segment(s) of the coronary artery or arteries during coronary bypass surgery via an opening made in the diseased vessel distal to the area to be bypassed by the bypass graft. It is also envisaged that the extremely small diameter distal end portion of the above-described drive shaft may be advanced into the diseased vessel without use of a guidewire and using a modified device which does not have a drive shaft sheath which extends around the flexible, hollow, fluid impermeable drive shaft. In one preferred embodiment, the outer diameter of the proximal portion of the drive shaft which may be used during coronary bypass surgery should be less than about 1 mm. In the most preferred embodiment, the said distal end portion of the drive shaft should have its outer diameter less than about 0.6 mm, thereby making it possible to completely or partially remove stenotic lesion(s) located in the diseased vessel distally to the location of the anastomosis between the diseased vessel and the coronary bypass graft. It is envisaged that operation of the above described thin walled drive shaft during open heart surgery may require to maintain the pressure of the flushing fluid in the rotating drive shaft at a certain sufficiently high level to prevent buckling or collapsing of said distal portion of the drive shaft formed only by the fluid impermeable membrane.

The distal portion of the drive shaft which is formed only by the membrane may extend distally from the distal end of that section of the drive shaft which is formed from both the coiled wire and the fluid impermeable membrane. The membrane may be made from plastic tubing (e.g. Polytetrafluorothylene (PTFE) or Nylon), silicon resin tubing or some other lubricious fluid impermeable material.

The drive shaft of the atherectomy device may be configured so that rotation of the drive shaft in a particular direction at least partially generates a desired direction of fluid flow. For example, the hollow drive shaft lined from inside by the fluid impermeable membrane may be wound from at least one helically coiled wire and the direction of rotation of the fluid impermeable drive shaft is then selected such that coil windings of the drive shaft at least partially generate or assist in the generation of the retrograde flow of fluid and debris around the drive shaft. Alternatively, the hollow drive shaft which is wound from at least one helically coiled wire may be covered by the fluid impermeable membrane and the direction of rotation of the fluid impermeable drive shaft is then selected such that the coil windings of the drive shaft at least partially generate or assist in the generation of the antegrade flow of flushing fluid along the lumen of the fluid impermeable drive shaft. In yet another arrangement, the surface of the drive shaft can be provided with at least one helically formed groove in which case the direction of rotation of the drive shaft is selected such that the or each helical groove at least partially generates or assists in the generation of the retrograde fluid flow around the drive shaft. If the drive shaft sheath extends over the drive shaft and forms an annular lumen around the drive shaft it is also possible to form the inner surface of the sheath with a helical groove to achieve or assist in generating a directional fluid pumping effect.

In a preferred embodiment, the distal end of the flexible, hollow, fluid impermeable drive shaft is rounded. Alternatively, an element having a rounded outer surface may be mounted or formed at the distal end of the drive shaft.

In one embodiment of the present invention, the fluid impermeable drive shaft has a generally round support element located at the distal end of the drive shaft and spaced away from the abrasive element, both the abrasive element and the support element having their centre of mass collinear with the longitudinal axis of the drive shaft so that the generally round support element located distal to the abrasive element prevents the abrasive element from being turned into a wall of the vessel when the drive shaft has been moved forward within the vessel beyond a distal end of a guidewire which was advanced into the vessel prior to advancement of the drive shaft over the guidewire or, after the distal end of the guidewire has been withdrawn into a lumen of the hollow drive shaft or the guidewire has been completely removed from the lumen of the hollow drive shaft.

In another embodiment of the present invention, the fluid impermeable drive shaft of the present invention has two generally round support elements located on either side and spaced away from the abrasive element, both the abrasive element and support elements having their centres of mass collinear with the longitudinal axis of the drive shaft, at least one of the support elements preventing the abrasive element from being turned into a wall of the vessel and the support elements located on either side of the abrasive element allowing the abrasive element only to slide or, only to rotate and slide, along the wall of the vessel removing a thin layer of the stenotic material with each pass of the rotating abrasive element across the stenotic area of the vessel.

One of the support elements is positioned at the distal end of the drive shaft and the other proximal to the abrasive element. Preferably, each support element is positioned at or about the same distance from the abrasive element.

In a preferred embodiment, the drive shaft is formed from resilient flexible material such that a portion of the drive shaft located between the support elements attempts to maintain a straight configuration when extending through a curved portion of a vessel, the resilience of the drive shaft together with the support elements thereby urging the abrasive element towards an inner curvature of said curved portion of the vessel and away from an outer curvature of said curved portion of the vessel. In this way, the risk of penetrating the outer curvature of a curved portion of the vessel is significantly reduced. This is particularly important if stenotic lesion is asymmetric and stenotic material is located predominantly, or sometimes even exclusively, on the inner curvature of a vascular wall.

In yet another embodiment, the abrasive element has its centre of mass offset from the longitudinal axis of the drive shaft and the drive shaft has a rounded element mounted or otherwise formed at the distal end of the drive shaft, the rounded element being a counterweight which has its centre of mass offset from the longitudinal axis of the drive shaft in a direction diametrically opposite to the direction in which the centre of mass of the abrasive element is offset from the longitudinal axis of the drive shaft.

Advantageously, a second counterweight is mounted or otherwise formed on the drive shaft proximal to such eccentric abrasive element and has its centre of mass also offset from the longitudinal axis of the drive shaft in a direction diametrically opposite to the direction in which the centre of mass of the eccentric abrasive element is offset from the longitudinal axis of the drive shaft.

If the first and second counterweights are of a similar mass, then each of them is preferably positioned at the same or about the same distance from the abrasive element. In the most preferred embodiment, each of the two counterweights has a mass which is equal to one-half of a mass of the eccentric abrasive element. However, a solid body of the eccentric abrasive element and solid bodies of the counterweights may be made from materials having different density.

Counterweights having similar mass and positioned at the same or about the same distance from the abrasive element may be made from materials having different density and so may therefore differ significantly in their size. If the mass of one counterweight differs from the mass of the other, then they may be located at unequal distances from the abrasive element.

In any one of the preferred embodiments of the invention at least either a support element or a counterweight located at the distal end of the fluid impermeable drive shaft is made inflatable. In any one of the most preferred embodiments of the invention either both the distal and the proximal support elements or both the distal and the proximal counterweights are made inflatable.

In one of the most preferred embodiments of the invention either the support element(s) or counterweight(s) are formed by a fluid impermeable membrane which lines the inside of the flexible, hollow, drive shaft and extends out from the distal end of the torque transmitting layer of the drive shaft flaring radially outward and making at least about 180 degrees turn in order to extend proximally around the torque transmitting layer of the drive shaft for a distance sufficient to form at least one rounded inflatable support element or one rounded inflatable counterweight at the distal end of the drive shaft. In the most preferred embodiment of the invention, the fluid impermeable membrane makes at least about 270 degrees turn when it defines a distal support element or a distal counterweight after said support element or counterweight has been inflated.

In the most preferred embodiment(s) of the invention, the fluid impermeable membrane, upon making its at least about 180 degrees turn and forming one rounded inflatable support element or counterweight at the distal end of the drive shaft, extends further proximally around the torque transmitting layer of the drive shaft to form another rounded inflatable support element or counterweight, located proximally to and spaced away from the abrasive element mounted to or around the drive shaft.

In one preferred embodiment of the invention the fluid impermeable membrane, which lines the lumen of the flexible drive shaft has at least one opening located in its wall, distal to the abrasive element for communicating the lumen of the fluid impermeable drive shaft with a space within a fluid inflatable support element or counterweight located at the distal end of the drive shaft.

If the fluid impermeable drive shaft has both a distal and a proximal fluid inflatable support elements, then the fluid impermeable membrane, which lines the lumen of the flexible drive shaft preferably has at least two openings in its wall, the opening or openings located distal to the abrasive element communicating the lumen of the drive shaft with the space within the distal fluid inflatable support element and the other opening(s) located proximal to the abrasive element communicating the lumen of the fluid impermeable drive shaft with a space within the proximal fluid inflatable support element.

If the fluid impermeable drive shaft has both a distal and a proximal fluid inflatable counterweights, then the fluid impermeable membrane, which lines the lumen of the flexible drive shaft preferably has at least two openings in its wall, the opening or openings located distal to the eccentrically mounted abrasive element communicating the lumen of the drive shaft with a space within the distal fluid inflatable counterweight and the other opening(s) located proximal to the eccentrically mounted abrasive element communicating the lumen of the fluid impermeable drive shaft with a space within the proximal inflatable counterweight.

If the flexible, hollow, fluid impermeable drive shaft has a generally symmetrical inflatable support element, located at the distal end of the drive shaft, then the fluid impermeable membrane, which lines the lumen of the flexible drive shaft preferably should have two or more openings in it's wall for communication the lumen of the fluid impermeable drive shaft with the space within the inflatable support element, said openings being located in the wall of the membrane at about the same distance away from each other about the circumference of the drive shaft.

If the flexible, hollow, fluid impermeable drive shaft has both the distal and the proximal generally symmetrical fluid inflatable support elements, then the fluid impermeable membrane, which lines the lumen of the flexible drive shaft, preferably should have a set of two or more openings in its wall for communicating the lumen of the fluid impermeable drive shaft with the space within the distal supporting element and another set of two or more openings for communicating the lumen of the drive shaft with the space within the proximal support element, located proximally to the generally symmetric abrasive element mounted to or around the drive shaft.

Preferably, the atherectomy device of the invention includes a bearing support housing to which the drive shaft is rotatably coupled so that the drive shaft can be rotated with respect to the bearing support housing and flushing fluid may be pumped into a lumen of the fluid impermeable drive shaft.

The drive shaft sheath is preferably coupled to a drive shaft sheath support housing, which slideably receives the bearing support housing thereby forming a handle assembly which allows longitudinal movement of the fluid impermeable drive shaft with respect to the drive shaft sheath.

The bearing support housing may include at least one bearing disposed therein which rotatably supports a rigid hollow bearing supported shaft. The proximal end portion of the flexible, hollow, fluid impermeable drive shaft is coupled to a distal end portion of the rigid hollow bearing supported shaft so that the drive shaft rotates when the rigid hollow bearing supported shaft is rotated.

In one embodiment of the invention, the atherectomy device comprises a flushing fluid supply tube which may be releasably and operatively coupled to the proximal end portion of the fluid impermeable drive shaft such that after the flushing fluid supply tube has been coupled to the drive shaft, the longitudinal axis of the flushing fluid supply tube and the proximal end portion of the drive shaft are disposed in a coaxial relationship to each other so that flushing fluid can be pumped in a straight forward direction from the flushing fluid supply tube into the fluid impermeable lumen of the flexible drive shaft.

In a preferred embodiment of the invention, after the flushing fluid supply tube has been operatively coupled to the drive shaft, the longitudinal axis of the flushing fluid supply tube and the drive shaft become disposed in a coaxial relationship to each other so that flushing fluid can flow straight out of the distal end of the flushing fluid supply tube into a proximal end of the drive shaft lumen.

In one embodiment of the invention, the hollow bearing supported shaft slideably receives, through its distal end, a flushing fluid supply tube therein to enable flushing fluid to be supplied from a flushing fluid source through the fluid supply tube and the rigid hollow bearing supported shaft into the flexible fluid impermeable drive shaft. The hollow bearing supported shaft can freely rotate around a stationary fluid supply tube coaxially received within it through its proximal end, thereby forming a rotatable fluid supply coupling between these two elements to facilitate the straight forward flow of flushing fluid from the distal end of the stationary fluid supply tube into the rotatable hollow bearing supported shaft.

To rotate the rigid hollow bearing supported shaft and, in turn, the flexible drive shaft, a gas turbine is preferably mounted on the hollow bearing supported shaft and serves as a prime mover for rotating the flexible, hollow, fluid impermeable drive shaft. Alternatively, the rigid, hollow bearing supported shaft may serve as a shaft for an electric motor or may be operatively connected to an electric motor via a gear train or other type of transmission system. If a gas turbine is utilised as a prime mover then the bearing support housing is provided with at least one gas or air supply port to facilitate the supply of gas or air into the housing to drive the turbine.

A flexible fluid supply hose may connect a proximal end of a relatively rigid fluid supply tube to a remotely located source of flushing fluid. Alternatively, at least a distal end portion of the fluid supply tube is made rigid relative to the remainder of the fluid supply tube and said rigid distal end portion of the tube is received within the hollow bearing supported shaft to rotatably couple the fluid supply tube thereto.

In accordance with the above described embodiments of the invention, flushing fluid is supplied into the fluid impermeable lumen of the drive shaft from the flushing fluid supply tube. The distal end portion of the fluid supply tube being coaxial with the proximal end portion of the fluid impermeable flexible drive shaft, thereby enabling flushing fluid to flow in a straight forward direction from the flushing fluid supply tube into a fluid impermeable lumen of the flexible drive shaft.

In accordance with the above-described embodiments of the invention, the flushing fluid may be pumped directly from the flushing fluid supply tube into the lumen of the fluid impermeable drive shaft.

In another embodiment of the invention, the proximal end of the rigid hollow bearing supported shaft is releasably connected to another hollow fluid impermeable torque transmitting shaft for rotating the bearing supported shaft and for supplying flushing fluid into a lumen of the fluid impermeable drive shaft.

The torque transmitting shaft is connected to a rotatable centrifugal pump housing for rotation together with the pump housing and for supplying pressurised flushing fluid out of the pump housing through the bearing supported shaft and into the flexible, hollow, fluid impermeable drive shaft. The centrifugal pump housing, torque transmitting shaft and ultimately the flexible drive shaft are rotated by one prime mover separate from another prime mover dedicated to rotate an impeller so that during operation of the device, rotation of the impeller by a dedicated prime mover may be initiated before, and stopped after, rotation of the pump housing thereby allowing the physician to achieve retrograde flow of flushing fluid around the abrasive element prior to, and after, its rotation.

In one embodiment of the invention, the impeller is traditionally offset in the now rotatable centrifugal pump housing in order to maintain a sufficiently close clearance between the impeller and the housing at a "cut-water" area of the centrifugal pump.

In the most preferred embodiment of the invention a modified centrifugal pump comprising a modified impeller is utilised, the modified impeller being provided with teeth spaced from each other and protruding radially from a hub of the impeller, the modified impeller having its rotational axis coaxial with the rotational axis of the rotatable centrifugal pump housing, thereby allowing both the modified impeller and the rotatable centrifugal pump housing to rotate in either the same or opposite directions. In one embodiment, both the modified impeller and the rotatable centrifugal pump housing may be rotated by a common prime mover.

In one preferred embodiment of the invention, both the modified impeller and the rotatable centrifugal pump housing are rotated by separate prime movers so that during operation of the device, rotation of the impeller may be initiated before and stopped after rotation of the pump housing thereby allowing the physician to achieve retrograde flow of flushing fluid around the abrasive element prior to and after its rotation. Two independent electric motors may be used as the independent prime movers for rotating the modified impeller and rotatable centrifugal pump housing. Alternatively, gas turbines may be used instead of the electric motors.

In the preferred embodiment of the invention, the hollow fluid impermeable torque transmitting shaft is also flexible so that the rotational axis of the rotatable centrifugal pump housing and rotational axis of the rigid hollow bearing supported shaft may be oriented at an angle with respect each other.

In the most preferred embodiment of the invention, the rotational axes of the rotatable centrifugal pump housing is substantially vertically orientated while the flexible torque transmitting shaft allows the physician to position the rigid, hollow bearing supported shaft and its housing at any desirable angle relative to the vertically oriented axis of the rotatable centrifugal pump housing.

It is also within the scope of the invention to utilise two or more centrifugal pumps mounted on a common platform and rotatable together with such a platform. The rotatable platform is connected to the torque transmitting shaft for rotation of the drive shaft and the pumps are connected either sequentially or in parallel for providing adequate flushing fluid flow through the fluid impermeable drive shaft.

In one embodiment of the invention, a releasable housing coupling member is provided to releasably couple the fluid supply tube to the rigid hollow bearing supported shaft.

Preferably, the releasable housing coupling member includes at least one resiliently deformable arm that releasably couples the coupling member to the bearing support housing.

Preferably, the bearing support housing includes an opening, recess or groove to receive and locate the or each resiliently deformable arm therein.

A portion of the bearing support housing may be releasably and slideably receivable within the coupling member. Alternatively, a portion of the coupling member may be releasably and slideably receivable within the bearing support housing.

The releasable housing coupling member preferably includes a locking collar slideable into a locking position to prevent accidental disengagement of the or each resiliently deformable arm(s) from its locked position on the bearing support housing and operative disengagement of the fluid supply tube from the rigid bearing supported shaft.

In one embodiment, a modified releasable housing coupling member is provided to releasably couple the hollow fluid impermeable torque transmitting shaft to the rigid hollow bearing supported shaft. The modified releasable housing coupling member may also include a locking collar to prevent disengagement of the modified coupling member from the bearing supported housing and operative disengagement of the flexible torque transmitting shaft from the rigid bearing supported shaft.

If a rotatable torque transmitting shaft is utilised to rotate the rigid bearing support shaft, a protective sheath may extend around the torque transmitting shaft proximally from the modified housing coupling member. One or more bearings may be mounted along the length of the flexible torque transmitting shaft to reduce or eliminate friction between the torque transmitting shaft and the protective sheath around it.

In one embodiment, the device includes an optical sensing mechanism for detecting the speed of rotation of the flexible, fluid impermeable drive shaft. Preferably, the sensing mechanism comprises a pair of optical fibres comprising a light emitting fibre, a light receiving fibre and, an actuator mounted on the rigid hollow bearing supported shaft for rotation together with the bearing supported shaft and located between the light emitting and light receiving optical fibres, the actuator being configured to intermittently block light emitted by the light emitting optical fibre from being received by the light receiving optical fibre when the drive shaft is rotated.

In one embodiment of the invention, the light emitting and light receiving optical fibres have end surfaces facing each other so that light may be transmitted directly from the light emitting optical fibre to the light receiving optical fibre. In an alternative arrangement, the end surfaces of the optical fibres may not face each other, in which case light is transmitted from the end surface of the light emitting optical fibre to the end surface of the light receiving optical fibre via at least one light reflecting prism element.

In a preferred embodiment of the invention, the optical sensing mechanism comprises a pair of optical fibres which are parallel to each other and a prism element which includes at least two light reflecting surfaces for transmitting light from one optical fibre to another.

In one embodiment, the actuator comprises an opaque disc mounted on the rigid bearing support shaft and has one or more translucent or transparent regions or windows therein to allow light to pass through said regions from the light emitting to the light receiving optical fibre.

In the preferred embodiment of the invention, the optical sensing mechanism may be provided with control means for determining the speed of rotation of the drive shaft based on the frequency of the intermittent interruption of the passage of light from the light emitting optical fibre to the light receiving optical fibre.

As described above, in one embodiment of the device a flushing fluid supply tube is releasably coupled to the rigid hollow bearing supported shaft and, in a particularly preferred embodiment of the invention, improper coupling of the said tube to the said shaft prevents at least one optical fibre or a light reflecting prism element from being properly positioned with respect to the actuator, thereby causing rotation of the drive shaft to be stopped by a control signal when rotation of the drive shaft is not immediately accompanied by an appropriate interruption of light between light emitting and light receiving optical fibres.

If a hollow fluid impermeable torque transmitting shaft is releasably coupled to the rigid hollow bearing supported shaft for rotation thereof, then improper coupling of the said torque transmitting shaft to the said bearing supported shaft also prevents at least one optical fibre or a light reflecting prism element from being properly positioned with respect to the actuator, thereby causing rotation of the drive shaft to be stopped by a control signal when rotation of the drive shaft is not immediately accompanied by an appropriate interruption of light between light emitting and light receiving optical fibres.

The rotational atherectomy device may be used with a guidewire which is placed in the vessel to be treated prior to advancement of the drive shaft over the guidewire. Once the hollow fluid impermeable drive shaft has been advanced over the guidewire to a desired location in the vessel, and before rotation of the drive shaft, the guidewire is removed from the vessel and from the drive shaft lumen to enable flushing fluid pumped into the drive shaft lumen to flow in an antegrade direction through the entire internal cross-section of the fluid impermeable drive shaft lumen including a portion of the cross-section of the drive shaft lumen which was occupied by the guidewire prior to its removal.

According to the invention, there is also provided a method of using a rotational atherectomy device to remove a stenotic lesion from within a vessel of a patient, comprising the steps of advancing a flexible, hollow, fluid impermeable drive shaft, having an abrasive element located thereon proximal to its distal end, into a vessel to be treated and locating the drive shaft in the vessel with the abrasive element adjacent to the stenotic lesion and, initiating rotation of the drive shaft and an antegrade flow of pressurised flushing fluid into a drive shaft lumen extending through the drive shaft so that flushing fluid enters the vessel through at least one luminal opening in the drive shaft distal to the abrasive element and so that at least some of the flushing fluid entering the vessel distal to the abrasive element flows in a retrograde direction over the abrasive element and the drive shaft to entrain debris abraded by the abrasive element for removal of said debris from the patient.

In accordance with the method of the invention, the pressure of the flushing fluid is chosen so that fluid pressure in the vessel distal to the abrasive element increases to a level at which a pressure gradient is generated across the point or region of entry of the fluid into the vessel. This pressure gradient results in the generation of retrograde flow of fluid over the drive shaft to entrain debris abraded by the abrasive element.

The method preferably includes the step of operatively coupling a fluid supply tube to the proximal end of the drive shaft lumen prior to initiation of rotation of the drive shaft and antegrade flow of pressurised flushing fluid. The coupling of the fluid supply tube to the proximal end of the drive shaft may be direct or indirect. However, the longitudinal axis of the fluid supply tube and the drive shaft are preferably disposed in a coaxial relationship to each other when coupled so that fluid can flow straight out of the distal end of the fluid supply tube and into the proximal end of the drive shaft lumen.

The step of initiating rotation of the drive shaft to abrade a stenotic lesion may be undertaken after an antegrade flow of pressurised flushing fluid has been established and, most preferably, after a retrograde flow of at least a portion of that flushing fluid over the abrasive element and the drive shaft has been established.

In accordance with one embodiment of the invention, the method includes the step of advancing a guidewire into the vessel so that it extends across the stenotic lesion prior to advancing the flexible, hollow, fluid impermeable drive shaft over the guidewire, the method further including the step of withdrawing the guidewire from the vessel and the drive shaft by pulling it out of the proximal end of the drive shaft when the abrasive element has been located adjacent to the stenotic lesion and before initiating rotation of the drive shaft or antegrade flow of flushing fluid.

If the method includes the step of operatively coupling a fluid supply tube to the proximal end of the drive shaft lumen, the step of withdrawing the guidewire from the vessel and the drive shaft is carried out prior to the step of operatively coupling the fluid supply tube to the proximal end of the drive shaft lumen.

The atherectomy device of the present invention may include a drive shaft sheath that extends over the drive shaft and terminates proximal to the abrasive element and which defines an annular lumen around the drive shaft so that the flushing fluid and debris entrained in the flushing fluid, that has flowed in a retrograde direction over the abrasive element and the drive shaft, flows into the annular lumen in the sheath for removal of said debris from the patient.

If the drive shaft sheath includes at least one additional discrete lumen which is separate to the annular lumen through which the drive shaft extends the method may include the step of pumping lubricating fluid in an antegrade direction along the or each additional discrete lumen and into the vessel from the distal end of the drive shaft sheath.

The annular lumen defined by the sheath may advantageously be in communication with a suction device to generate or assist in the generation of retrograde flow of fluid and debris over the abrasive element so that said fluid and debris are drawn into the annular lumen in the sheath from the vessel for removal from the patient. In this case, the method includes the step of actuating the suction device after initiating an antegrade flow of flushing fluid along the drive shaft lumen.

Alternatively, the suction device may then be in communication with the separate discrete lumen in the sheath so that flushing fluid and entrained debris is sucked into said discrete lumen for removal from the patient rather than into the annular channel between the drive shaft and the sheath. Lubricating fluid may then also be pumped in an antegrade direction through the annular channel in the sheath, in addition to the flushing fluid pumped in an antegrade direction through the drive shaft lumen. The lubricating fluid lubricates the drive shaft as it rotates within the sheath. Furthermore, the absence of debris in the fluid flowing along the annular channel may be preferable as the presence of the debris may increase friction between the drive shaft and the sheath.

The method may also include the step of controlling the flow of lubricating fluid in an antegrade direction through the annular channel in the sheath and the suction of fluid through the discrete lumen in the sheath, so that fluid entering the vessel from the annular channel in the sheath is drawn into the discrete lumen in the sheath together with fluid and debris that has flowed in a retrograde direction over the abrasive element and which has entered the vessel from the distal end of the drive shaft, or that portion of the drive shaft which is distal to the abrasive element.

If the drive shaft is formed from at least one helically coiled wire, the method preferably includes the step of rotating the drive shaft in a direction such that the outer surface of the helically coiled wire itself at least partially contributes to generating a retrograde flow of fluid over the abrasive element and through the annular channel between the drive shaft and the sheath so that the need for a source of suction may be eliminated altogether.

In one embodiment of the invention, the proximal end of the fluid impermeable drive shaft is operatively coupled to a flushing fluid supply tube. The longitudinal axis of the flushing fluid supply tube and the drive shaft may be disposed in a coaxial relationship to each other so that flushing fluid can flow straight out of the distal end of the flushing fluid supply tube and into the proximal end of the drive shaft lumen.

According to another aspect of the invention, there is provided a rotational atherectomy device comprising a prime mover for rotating a hollow flexible drive shaft and a fluid supply line for providing an antegrade flow of fluid along a lumen of said hollow flexible drive shaft, the fluid supply line comprising a straight, stationary fluid supply tube at its distal end and a flexible fluid supply tube at its proximal end, at least the distal end portion of the straight, stationary fluid supply tube being located inside a hollow shaft of the prime mover, the hollow prime mover shaft and the straight, stationary fluid supply tube being coaxial relative to each other thereby permitting rotation of the hollow prime mover shaft around said straight stationary fluid supply tube.

According to another aspect of the invention, there is provided a rotational atherectomy device for removing a stenotic lesion from within a vessel of a patient, the device comprising a rotatable, flexible, hollow drive shaft having a longitudinal axis of rotation and an abrasive element mounted on a region of the drive shaft proximal to its distal end, wherein said region of the drive shaft which receives the abrasive element has a non-circular cross section when viewed in a cross-section which is transverse with respect to the longitudinal and/or rotational axis of the drive shaft, thereby preventing rotation of the abrasive element relative to the drive shaft.

In a preferred embodiment, the drive shaft is fluid impermeable.

A short region of the drive shaft may comprise a specially formed seat to receive the abrasive element.

The present invention also provides a rotational atherectomy device for removing a stenotic lesion from within a vessel of a patient, the device comprising a rotatable, flexible, hollow fluid impermeable drive shaft having a longitudinal axis of rotation and a symmetric abrasive element mounted on a region of the drive shaft proximal to and spaced away from its distal end, characterised in that the drive shaft also includes two fluid inflatable support elements, a distal fluid inflatable support element located at a distal end of the drive shaft and spaced away from the abrasive element and, a proximal fluid inflatable support element located proximal to and spaced away from the abrasive element.

In a preferred embodiment, the distal and proximal fluid inflatable support elements are equally spaced from the abrasive element.

The distal fluid inflatable support element preferably includes at least one inflow opening communicating a lumen of the fluid impermeable drive shaft with an interior space of the distal fluid inflatable support element, said space at least partially defined by a fluid impermeable membrane, the at least one inflow opening preferably having an axis which is perpendicular to a rotational axis of the fluid impermeable drive shaft.

In a preferred embodiment, the distal fluid inflatable support element includes at least one outflow opening communicating the interior space of the distal fluid inflatable support element with a vascular space within the vessel of the patient.

The at least one outflow opening is preferably located in a portion of the fluid impermeable membrane which tapers inwards and faces rearwards towards the abrasive element when the distal fluid inflatable support element is inflated.

Advantageously, the distal fluid inflatable support element is configured to convert a flow of fluid in an antegrade direction along the fluid impermeable drive shaft to a retrograde flow of fluid around the fluid impermeable drive shaft and its abrasive element.

In a preferred embodiment, the proximal inflatable support element includes at least one inflow opening communicating a lumen of the fluid impermeable drive shaft with an interior space of the proximal fluid inflatable support element, said space at least partially defined by a fluid impermeable membrane.

The present invention further provides a rotational atherectomy device for removing a stenotic lesion from within a vessel of a patient, the device comprising a rotatable, flexible, hollow fluid impermeable drive shaft having a longitudinal axis of rotation and an eccentric abrasive element mounted on a region of the drive shaft proximal to and spaced away from its distal end, characterised in that the drive shaft also includes two fluid inflatable counterweights, a distal fluid inflatable counterweight located at a distal end of the drive shaft and spaced away from the abrasive element and, a proximal fluid inflatable counterweight located proximal to and spaced away from the abrasive element.

Preferably, the distal and proximal fluid inflatable counterweights are equally spaced from the abrasive element.

In a preferred embodiment, the distal fluid inflatable counterweight includes at least one inflow opening communicating a lumen of the fluid impermeable drive shaft with an interior space of the distal fluid inflatable counterweight, said space at least partially defined by a fluid impermeable membrane, the at least one inflow opening has an axis which is perpendicular to a rotational axis of the fluid impermeable drive shaft.

The distal fluid inflatable counterweight preferably includes at least one outflow opening communicating the interior space of the distal fluid inflatable counterweight with a vascular space within the vessel of the patient, the at least one outflow opening preferably being located in a portion of the fluid impermeable membrane which tapers inwards and faces rearwards towards the abrasive element when the distal fluid inflatable counterweight is inflated.

The distal fluid inflatable counterweight is advantageously configured to convert a flow of fluid in an antegrade direction along the fluid impermeable drive shaft to a retrograde flow of fluid around the fluid impermeable drive shaft and its abrasive element.

In a preferred embodiment, the proximal fluid inflatable counterweight includes at least one inflow opening communicating a lumen of the fluid impermeable drive shaft with an interior space of the proximal inflatable counterweight, said space at least partially defined by a fluid impermeable membrane.

Preferably, a centre of mass of each of the inflated distal and proximal fluid inflatable counterweights is located in the same plane as a centre of mass of the eccentric abrasive element, but diametrically opposite with respect to the rotational axis of the fluid impermeable drive shaft.

DETAILED DESCRIPTION OF THE DRAWINGS

Embodiments of the invention will now be described, by way of example only, in conjunction with the following drawings, in which.

Figure 2:
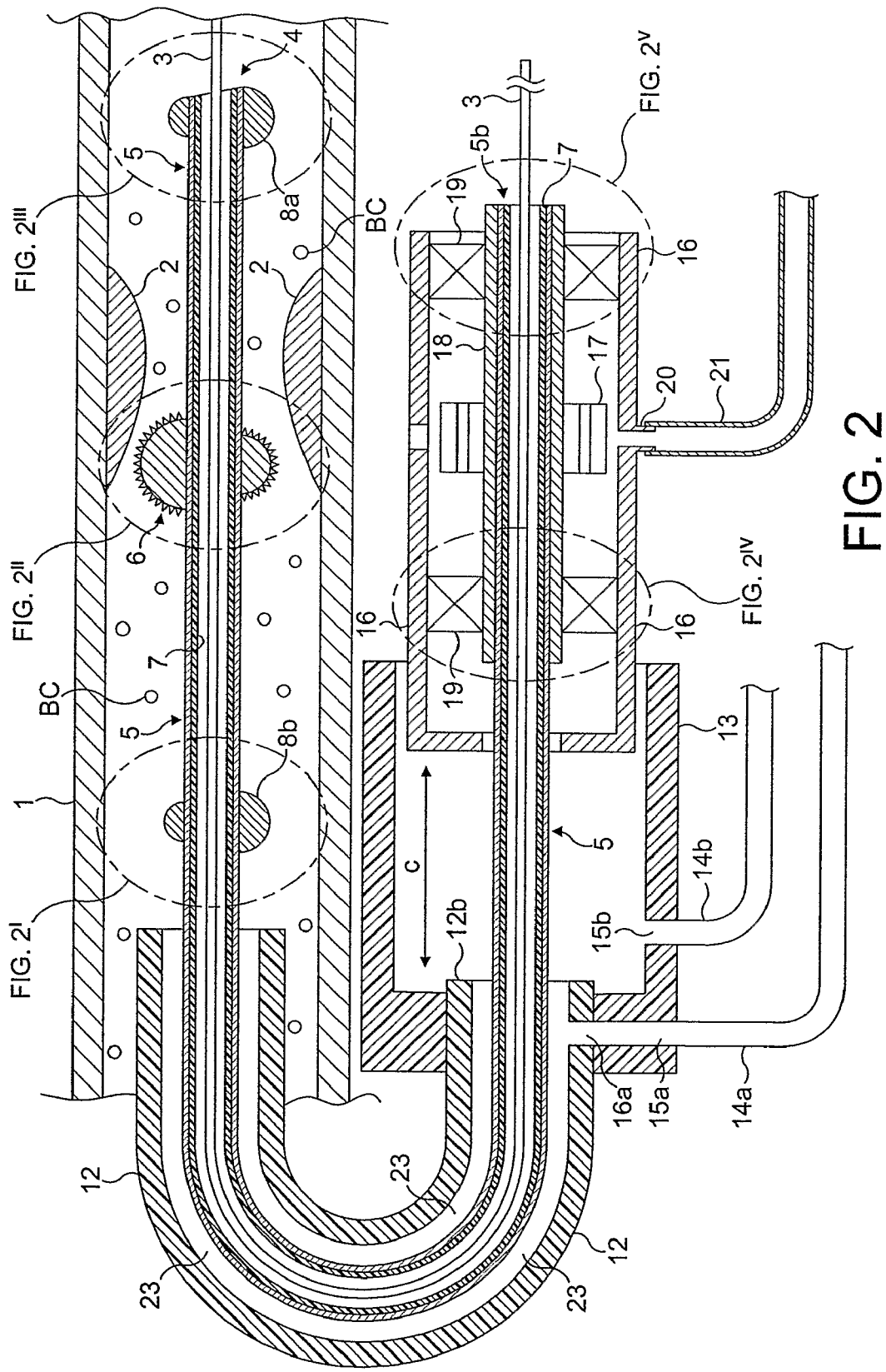
FIG. 2 is a side sectional view of the portion of the blood vessel and guidewire shown in FIG. 1 and illustrating a side sectional view of a rotational atherectomy device which has been advanced over the guidewire until an abrasive element mounted on the drive shaft is located adjacent to the stenotic lesion, the guidewire being shown advanced distally further along the vessel.
Figure 3:
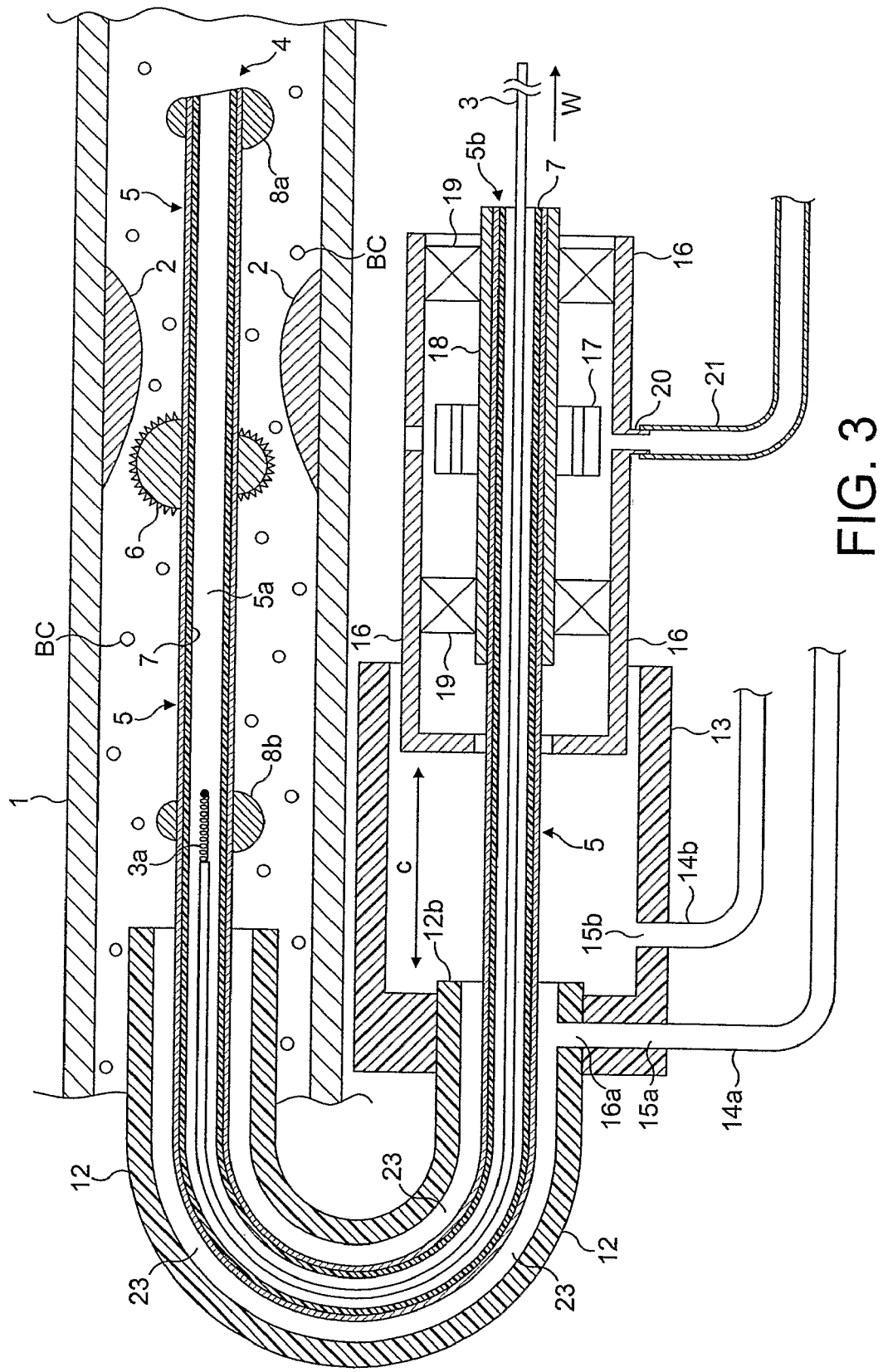
Figure 4A:
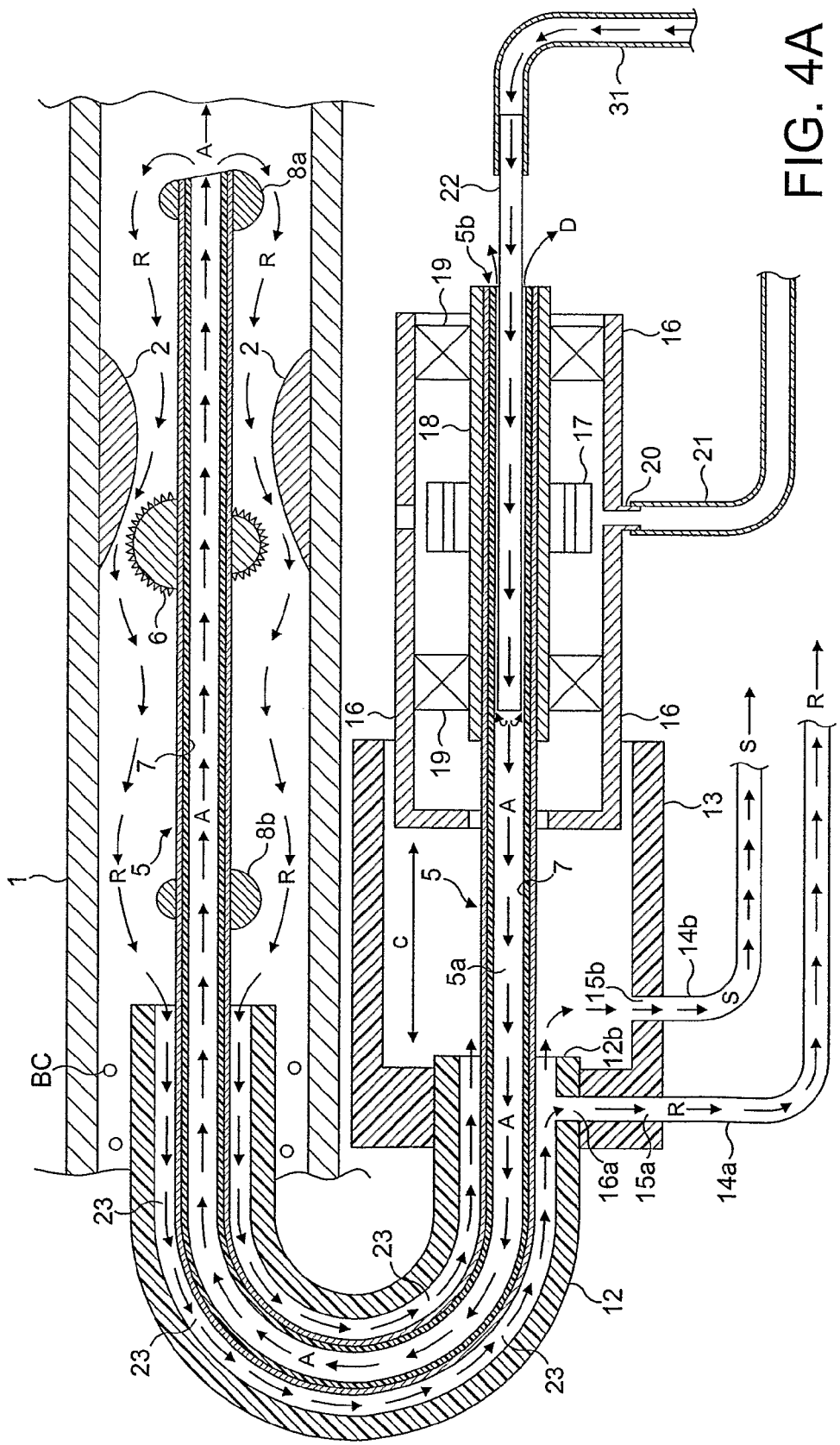
Figure 4B:
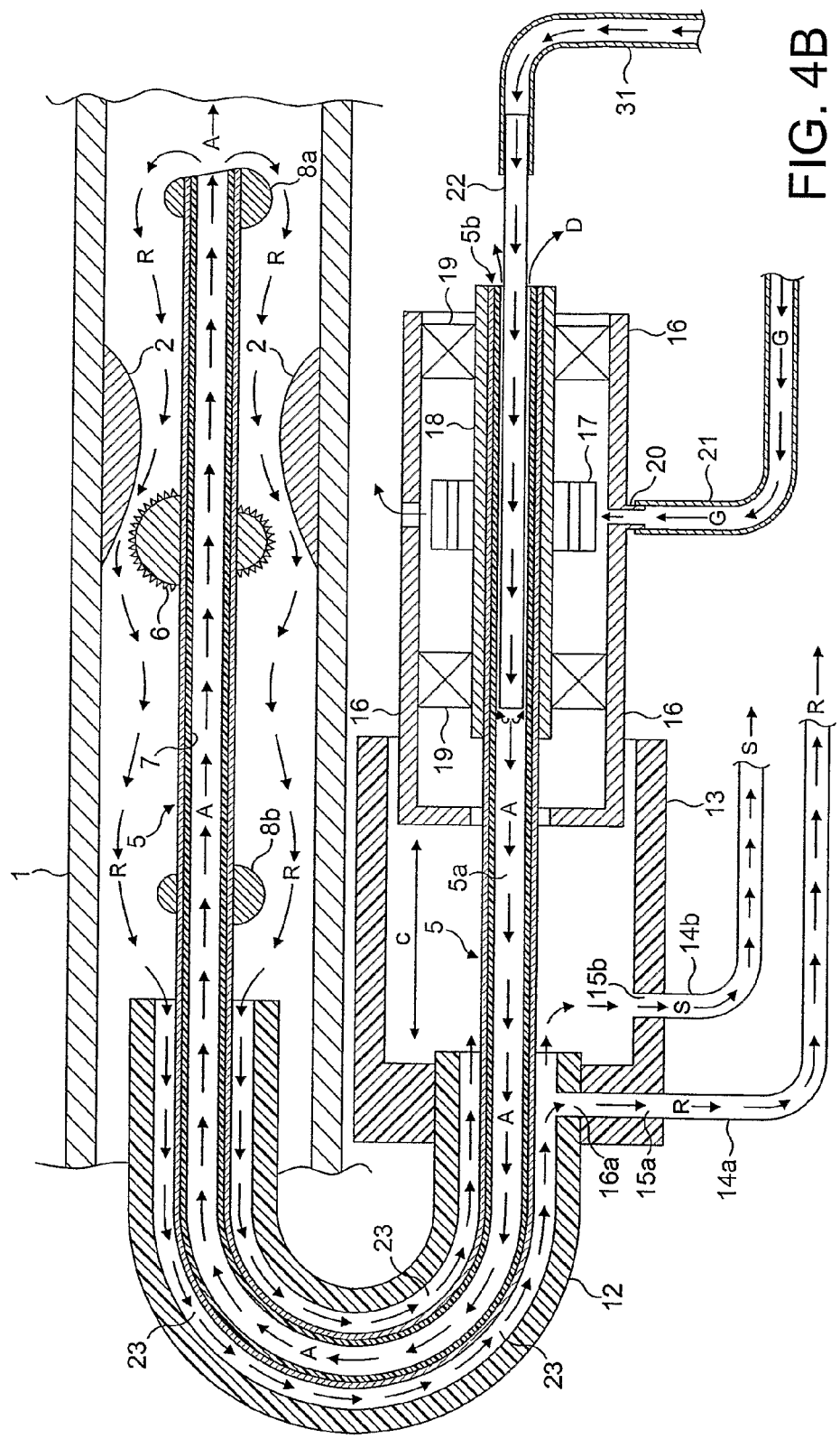
Figure 5A:
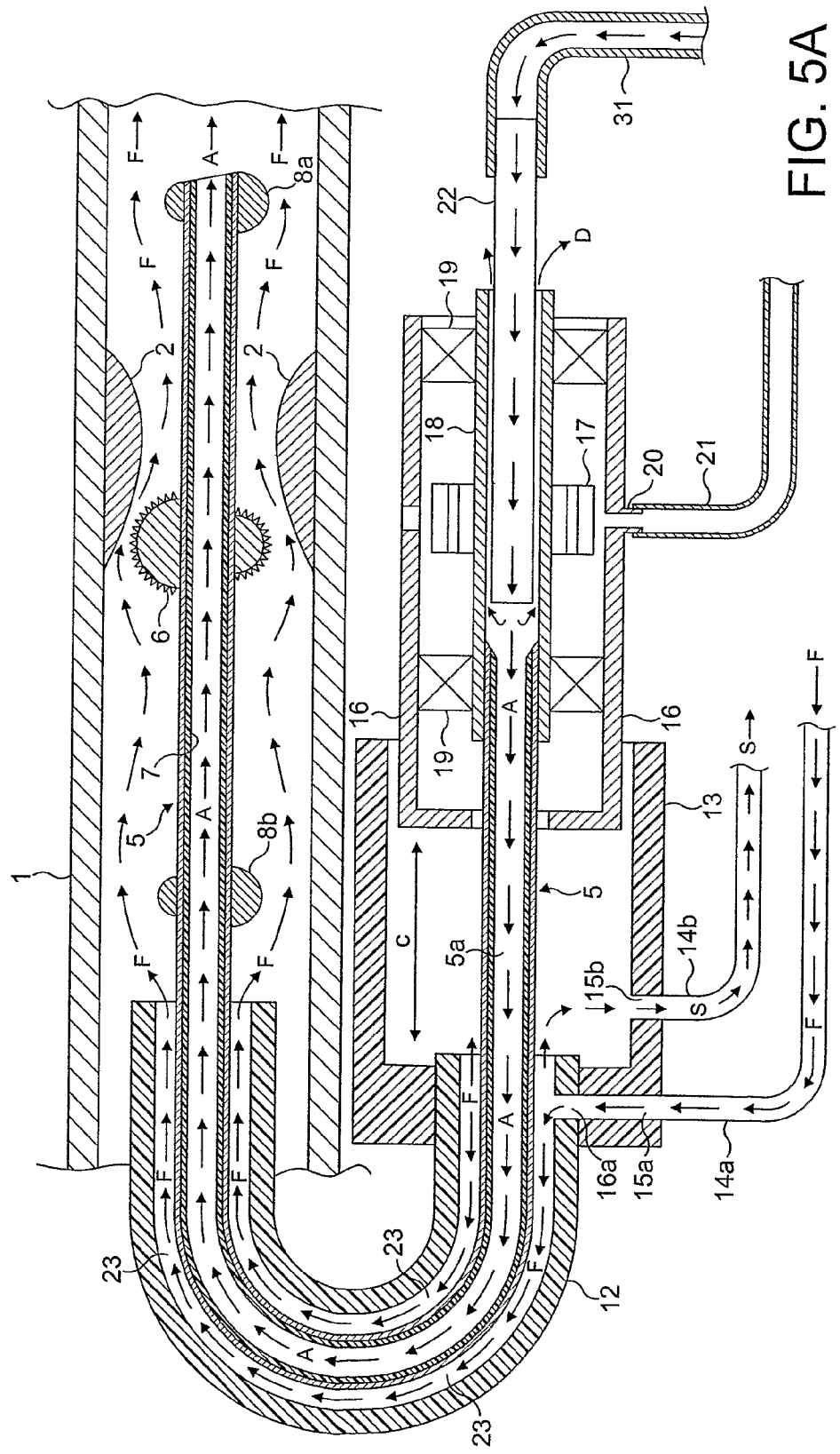
Figure 5B:
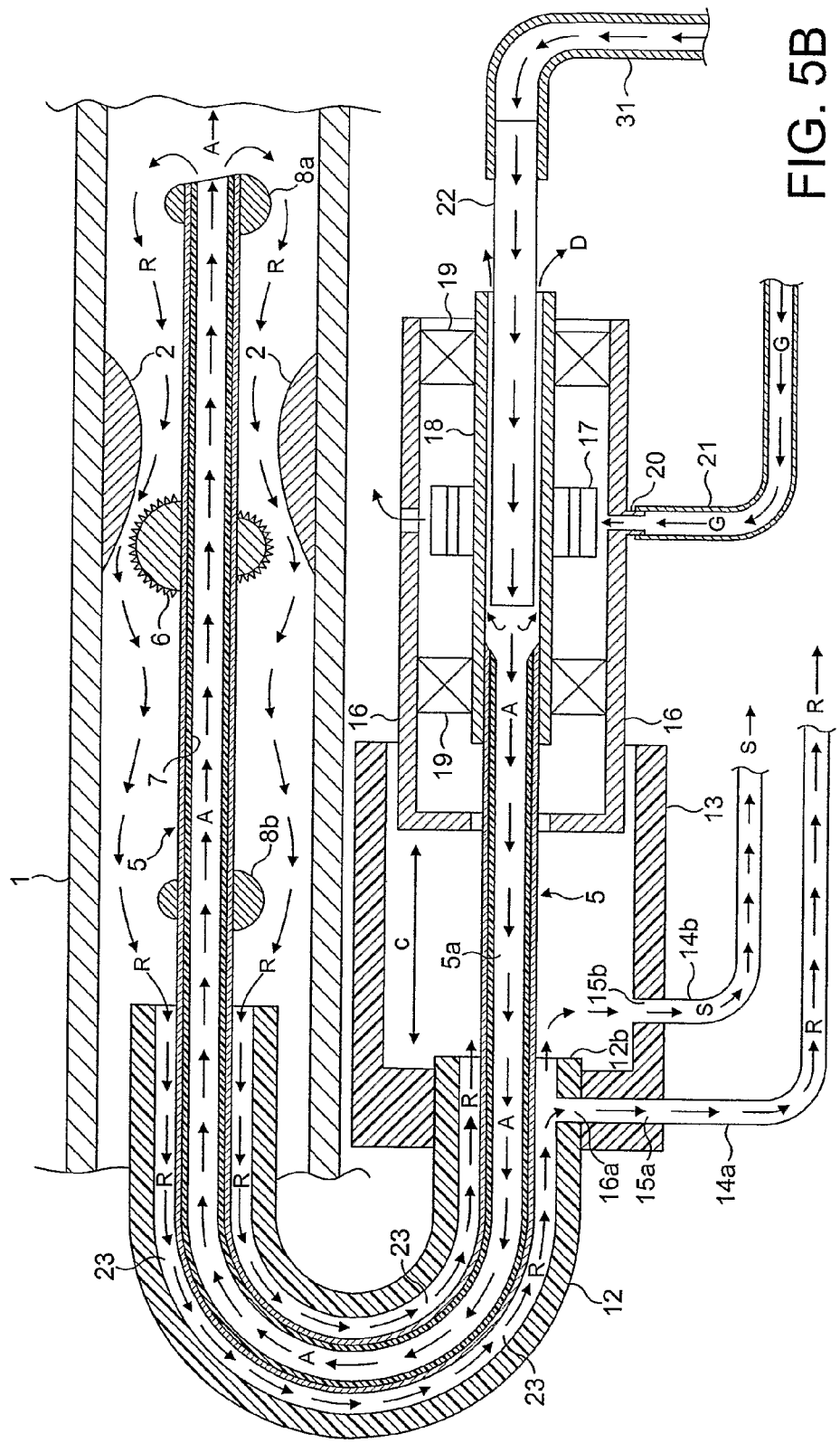
Figure 5B:
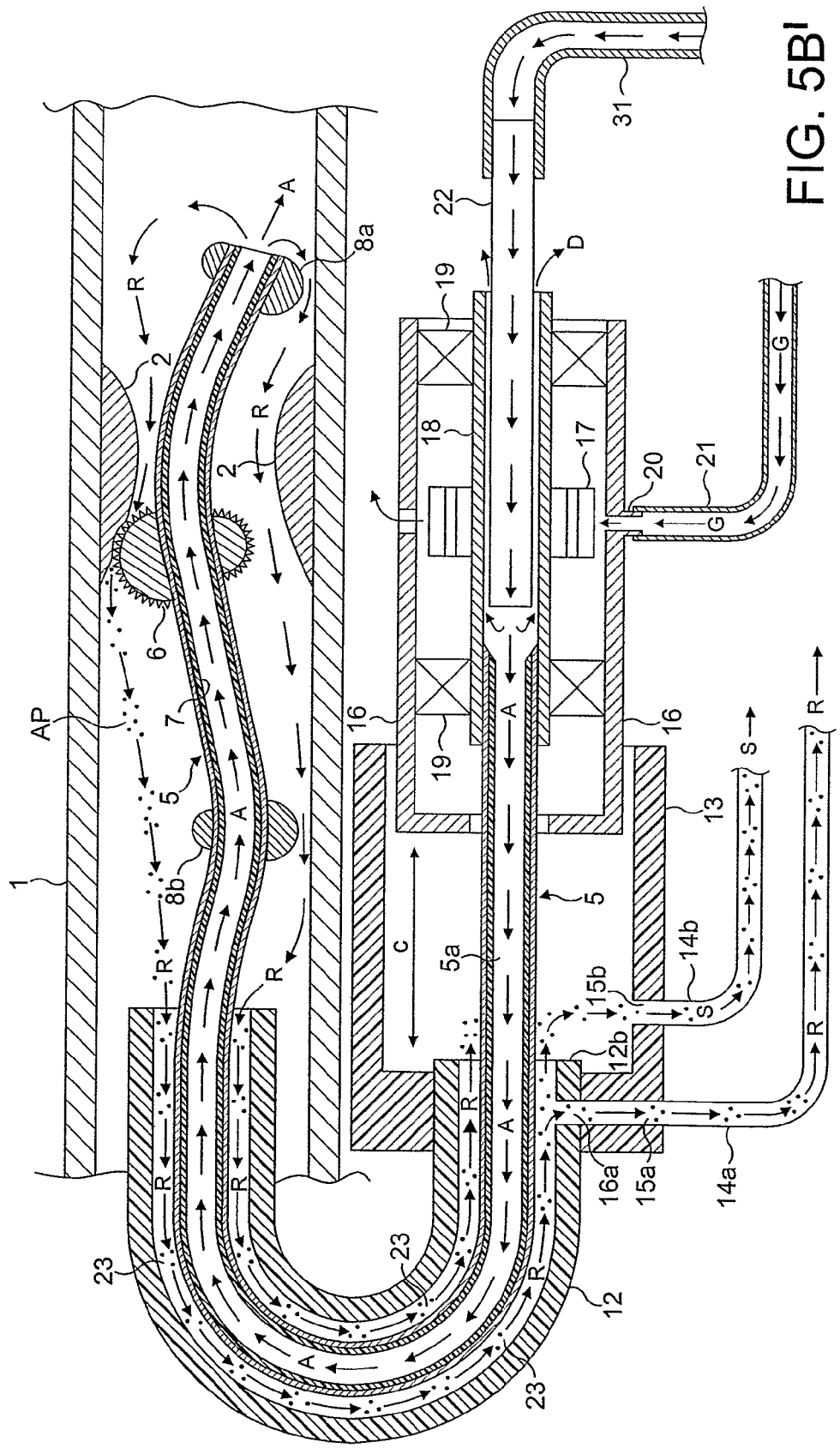
Figure 5B:
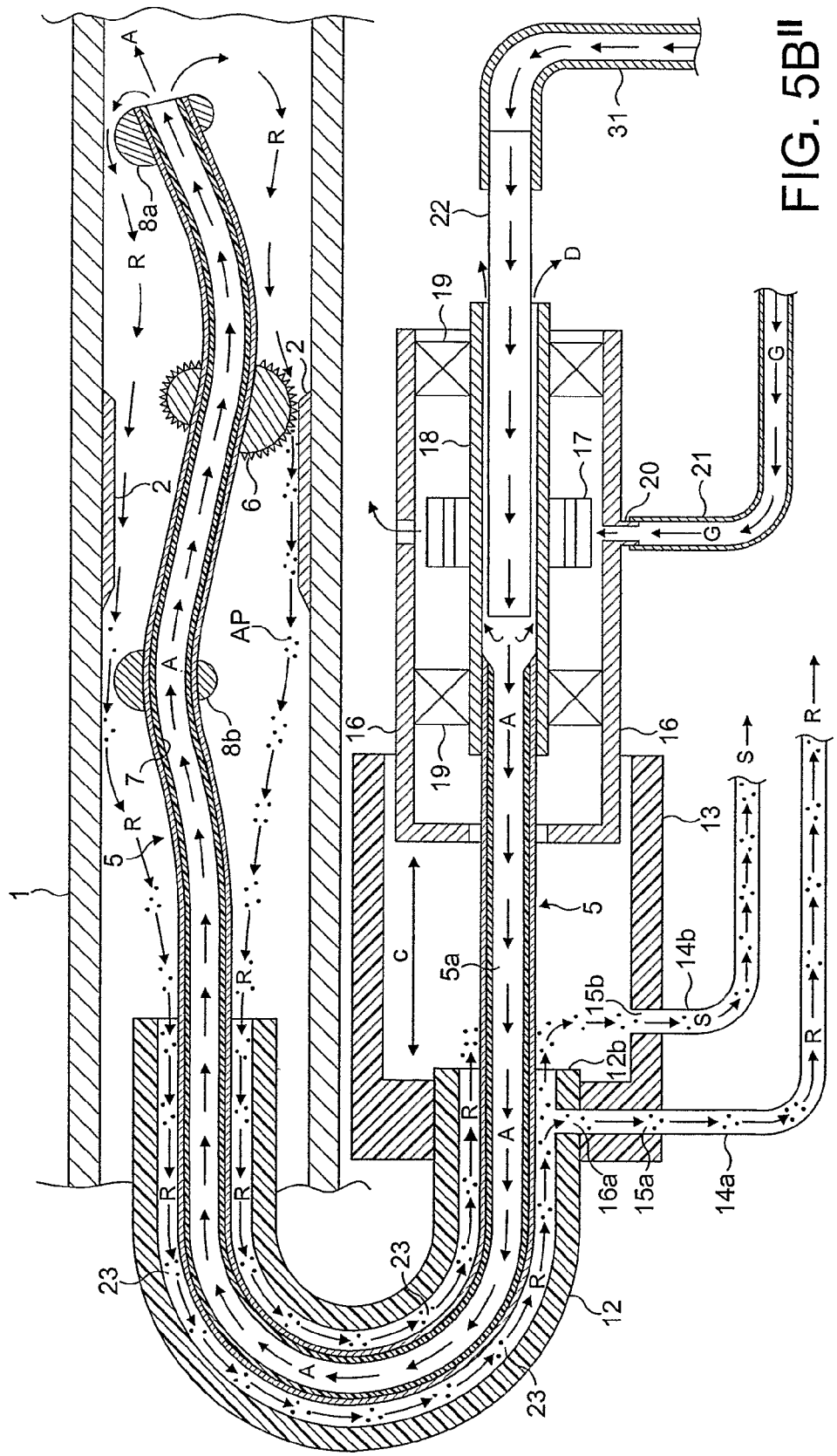
Figure 6A:
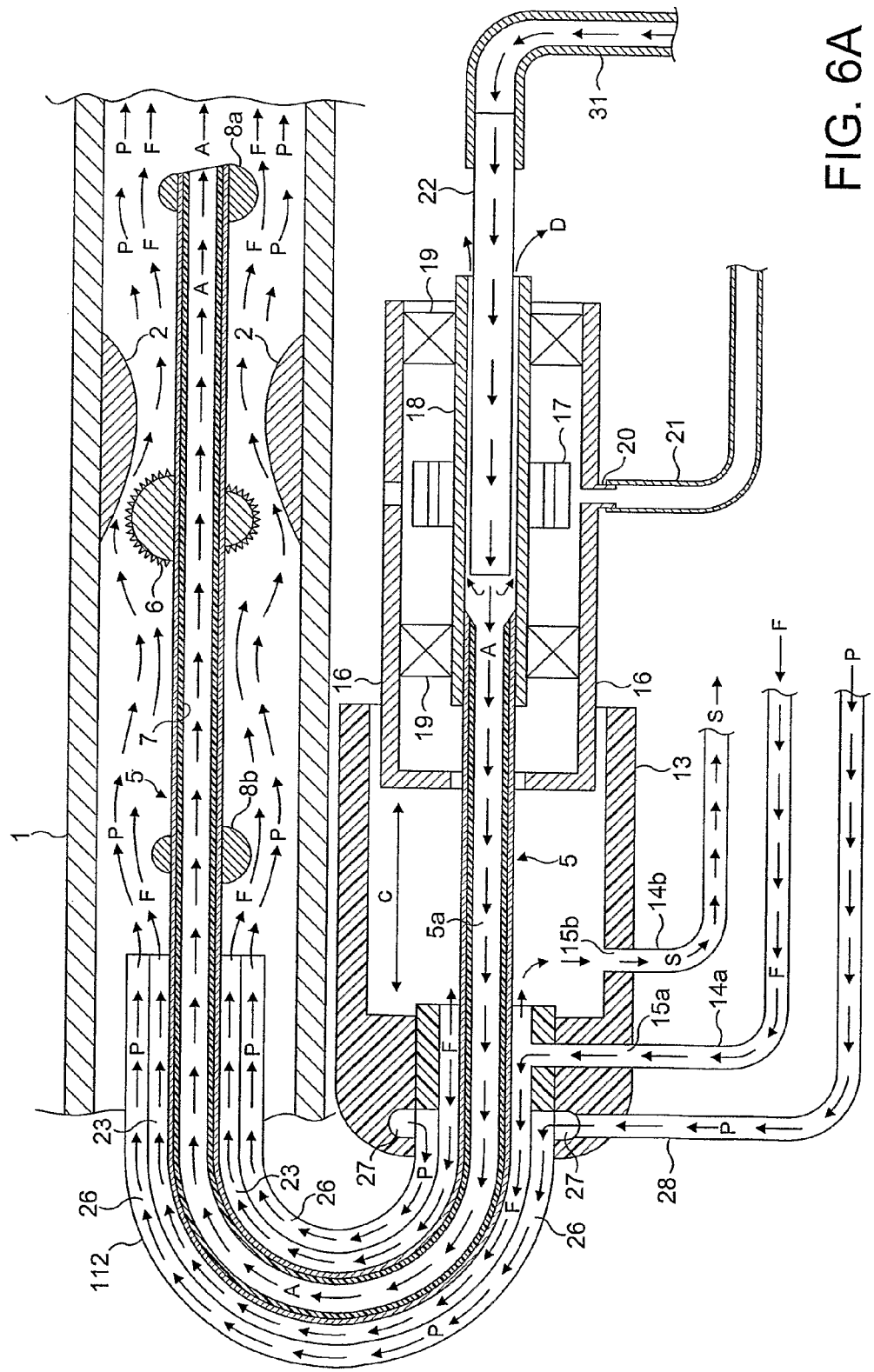
Figure 6B:
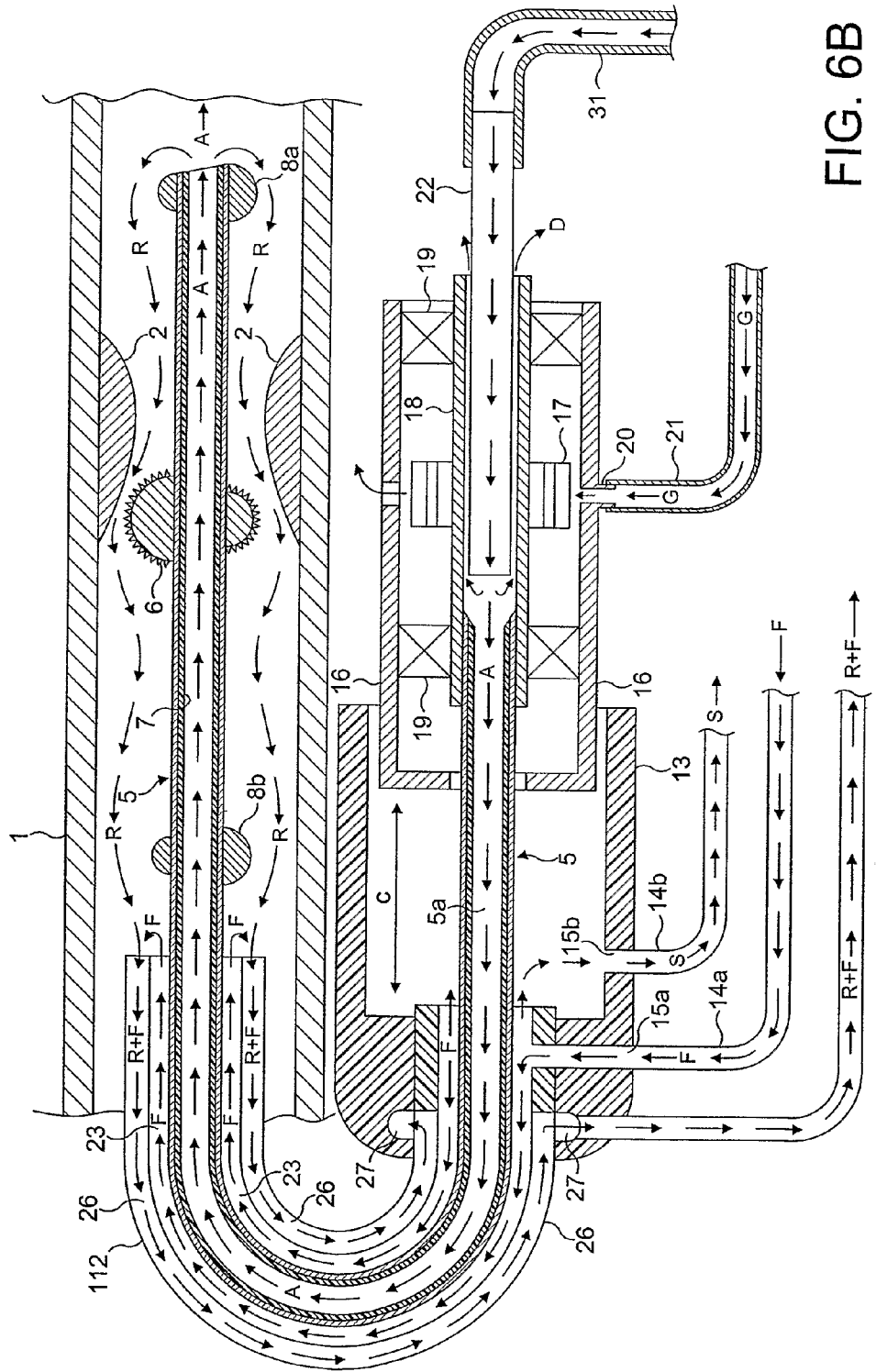
Figure 7:
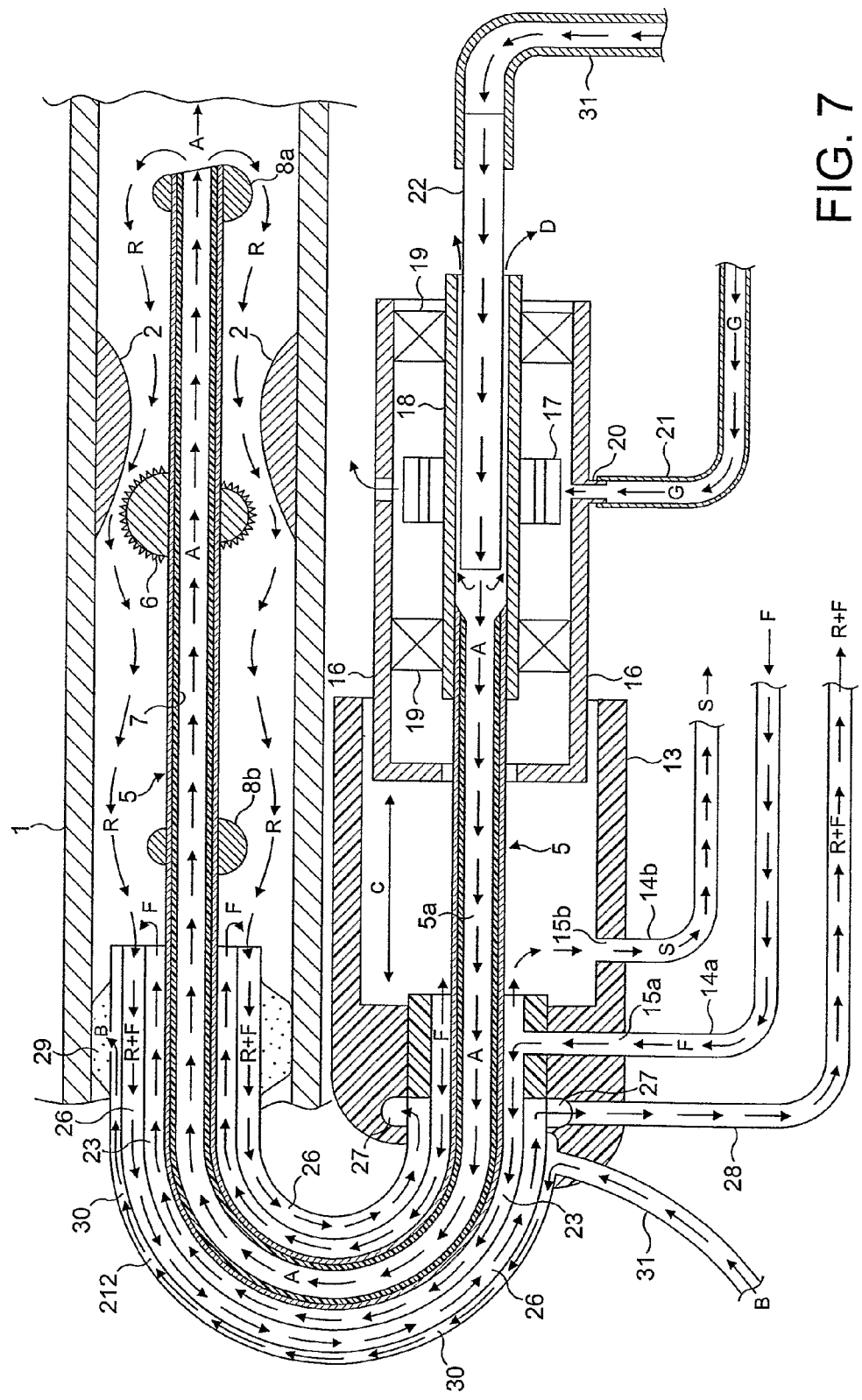
Figure 8A:
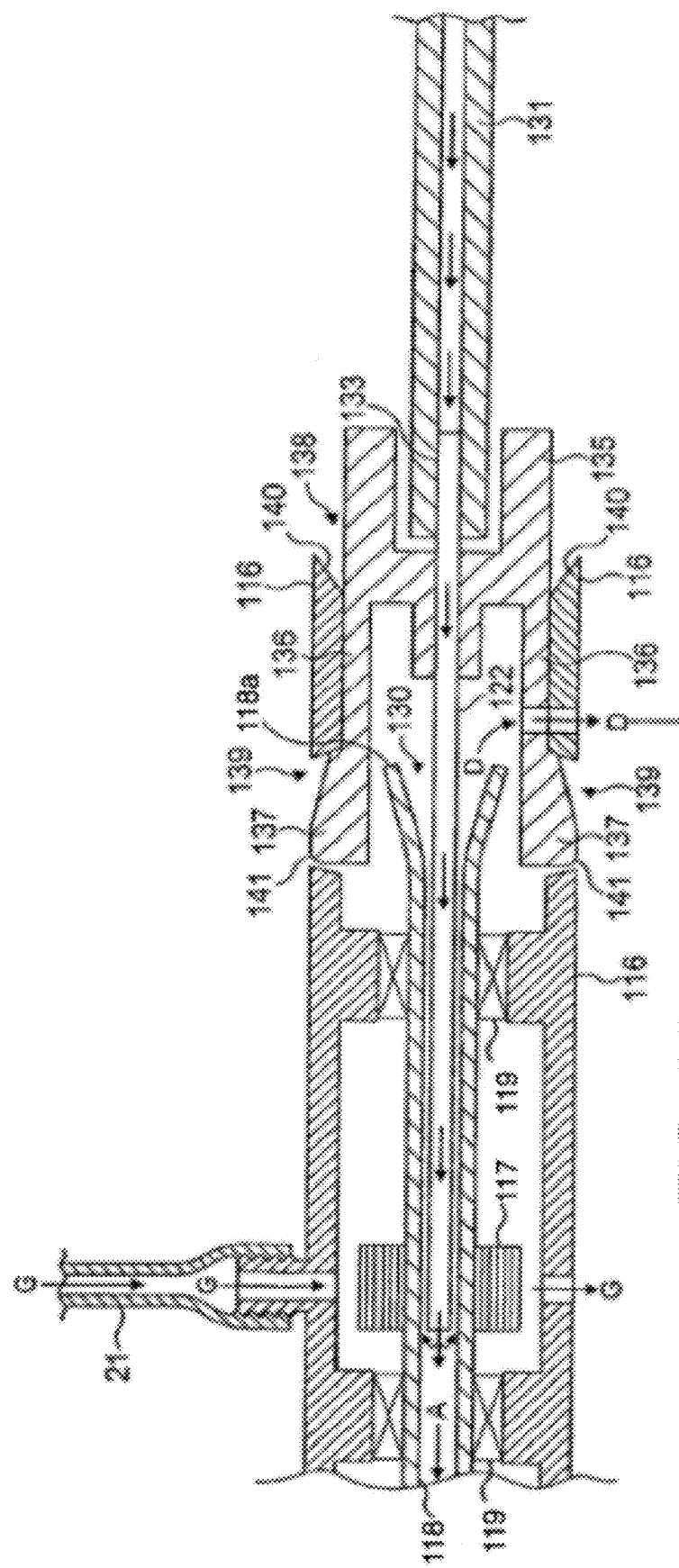
Figure 9A:
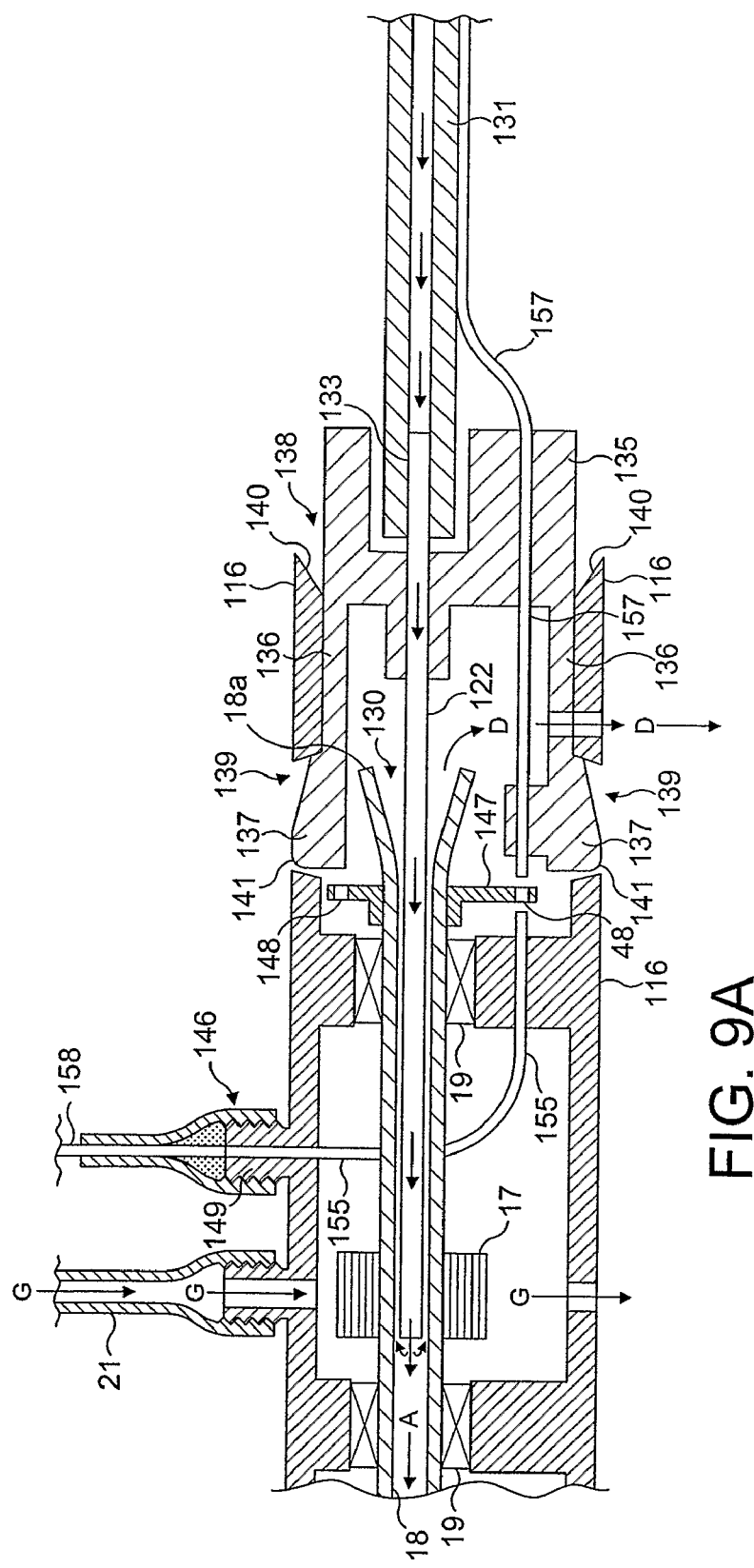
Figure 9B:
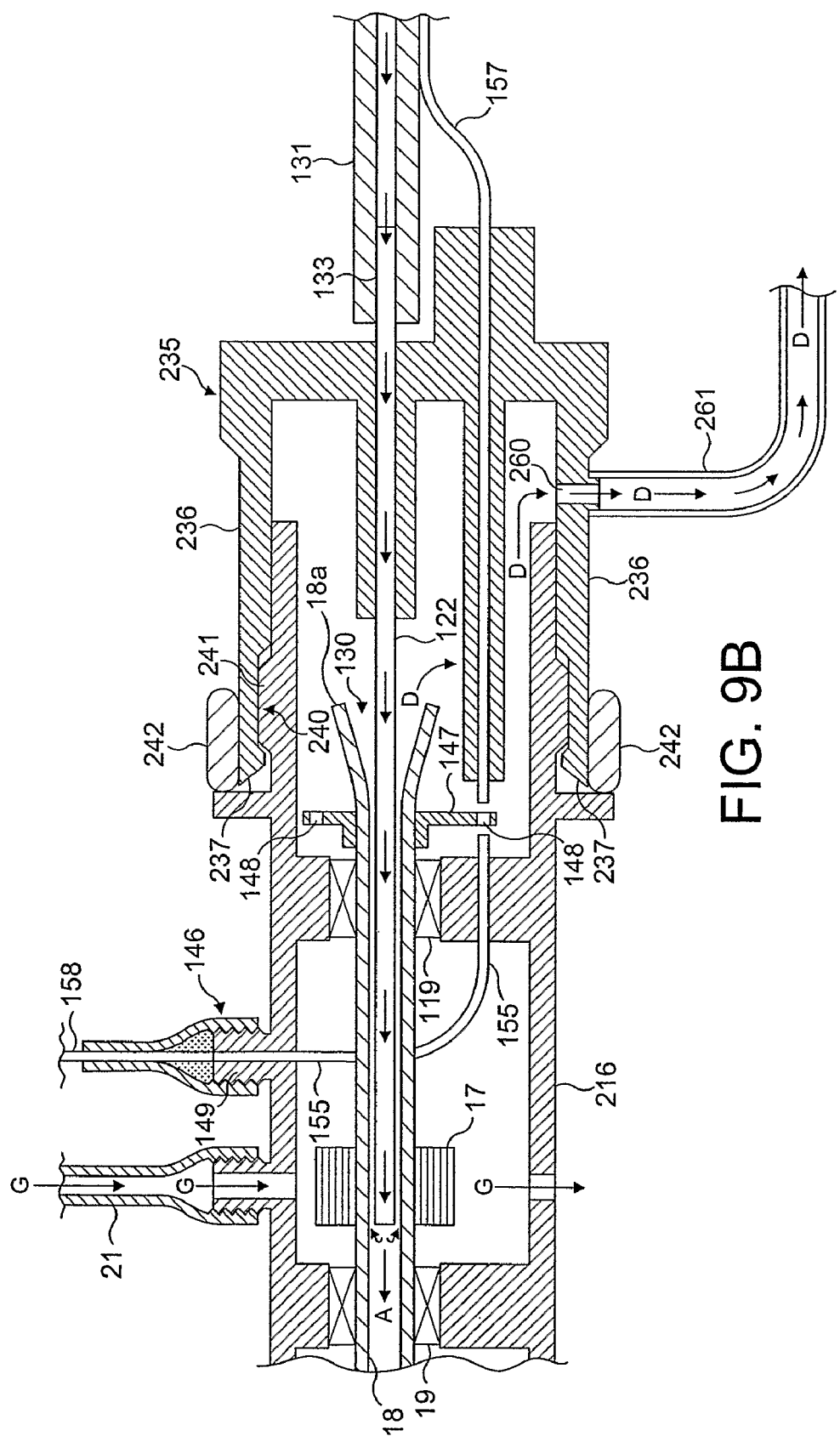
Figure 11:
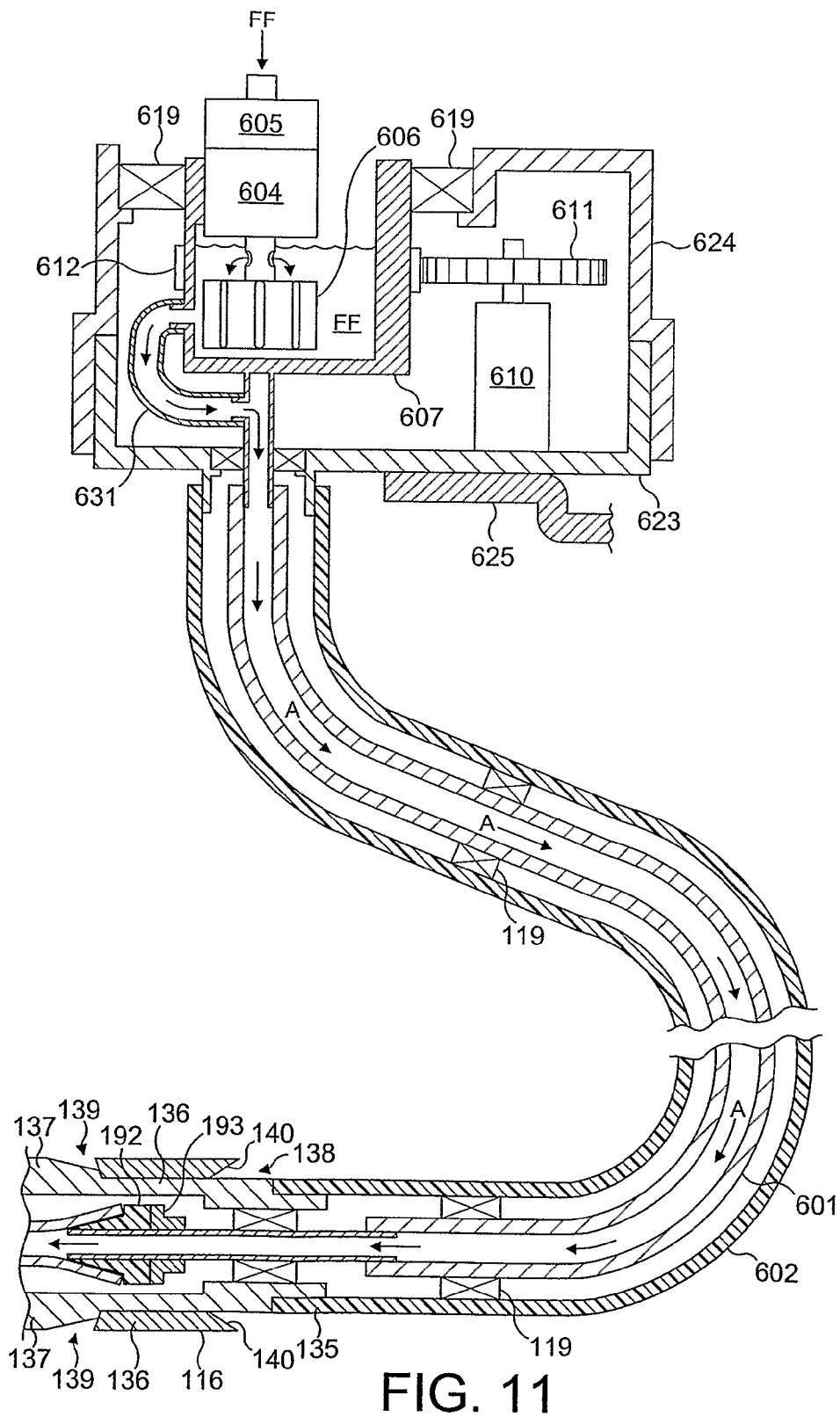
Figure 12:
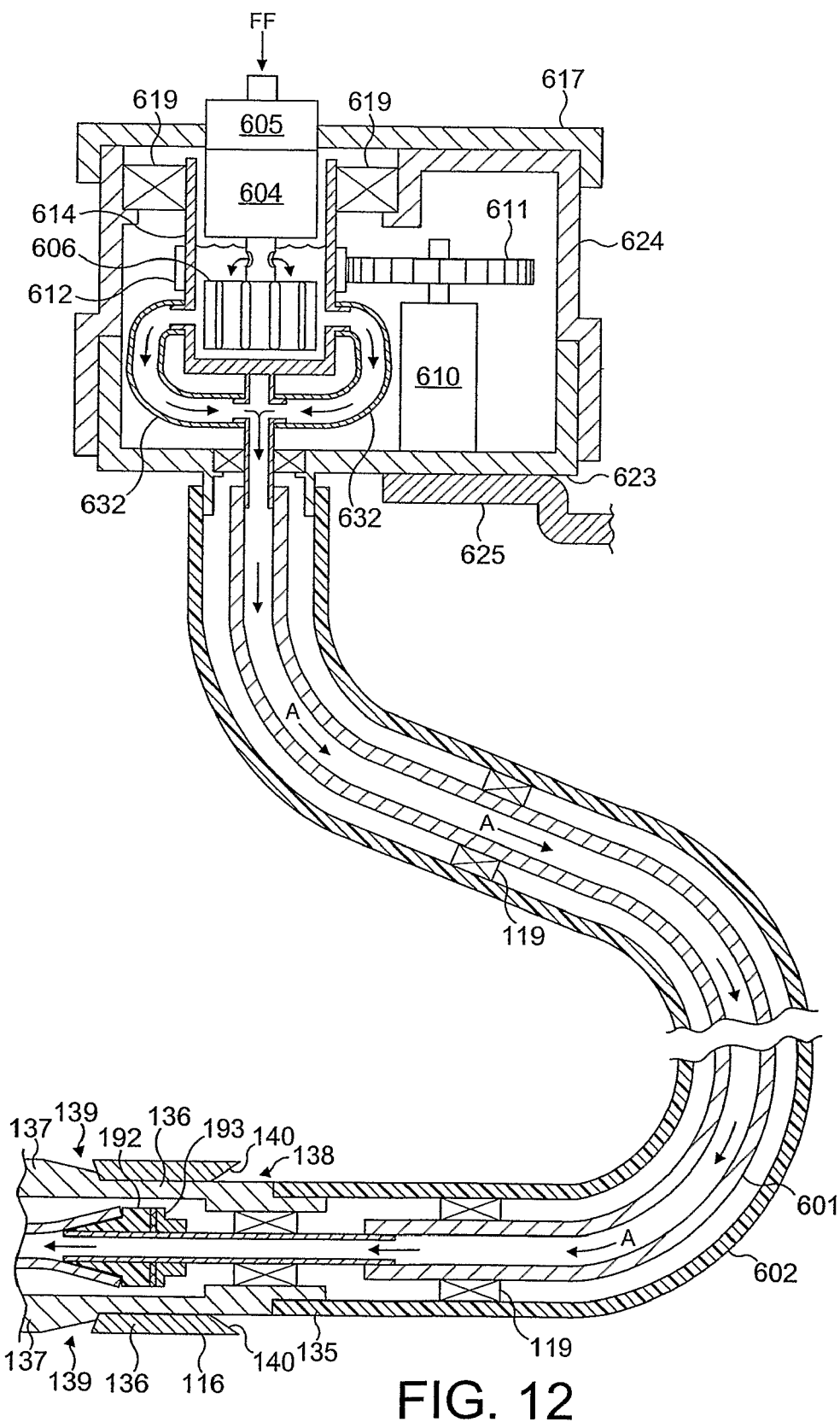
Figure 14:
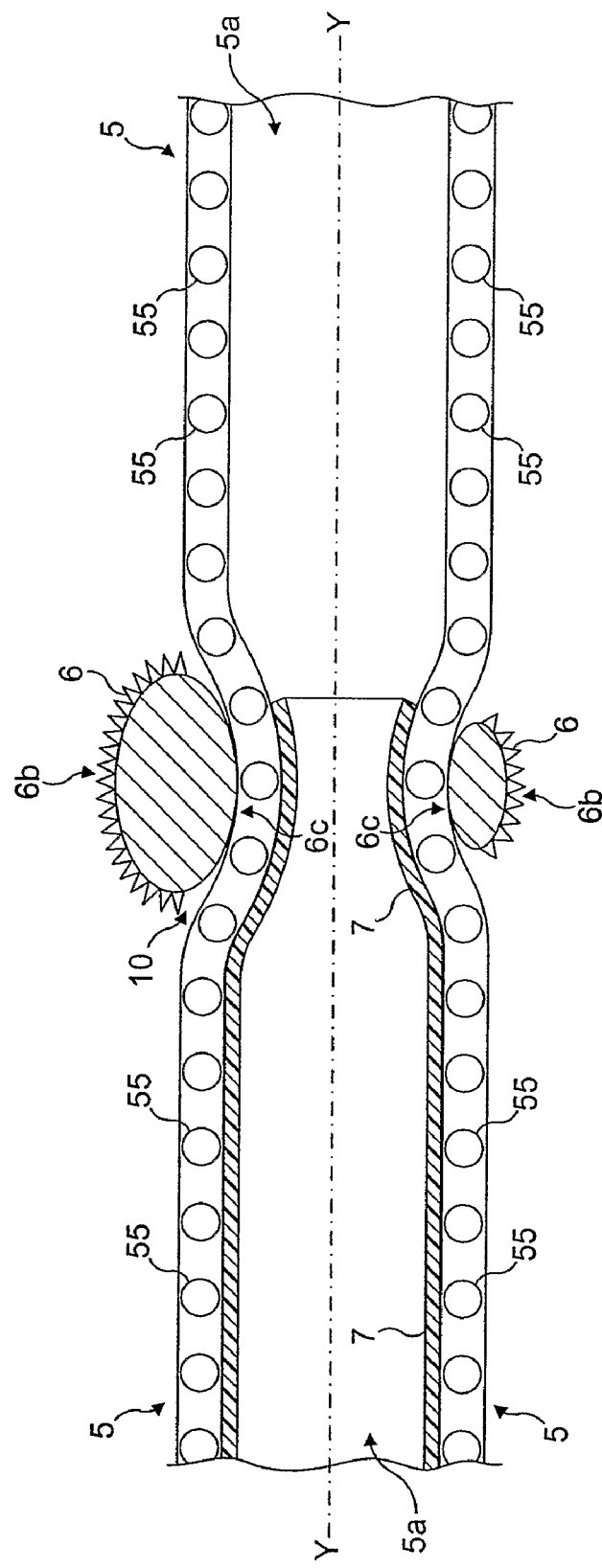
Figure 15:
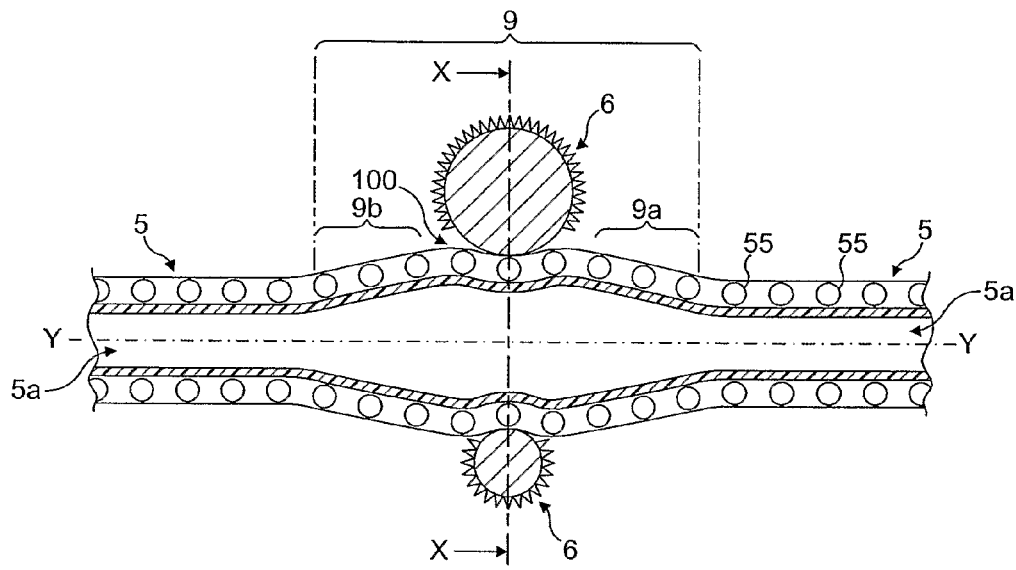
Figure 16:
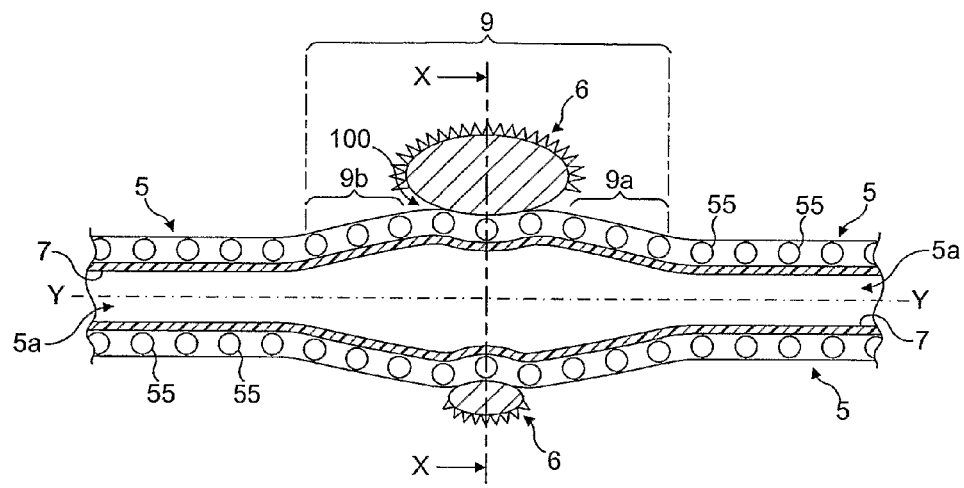
Figure 16A:
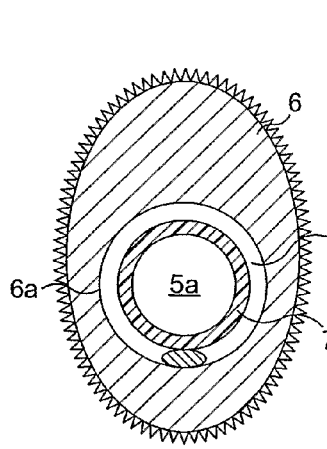
Figure 16B:
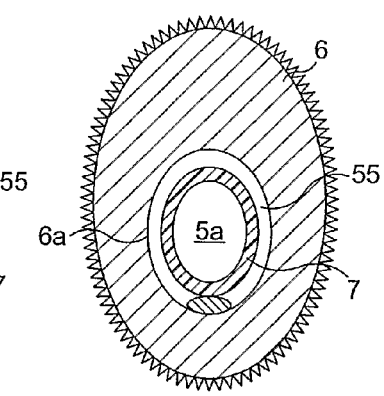
Figure 16C:
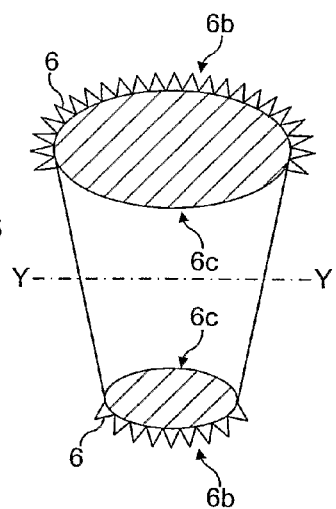
Figure 17B:
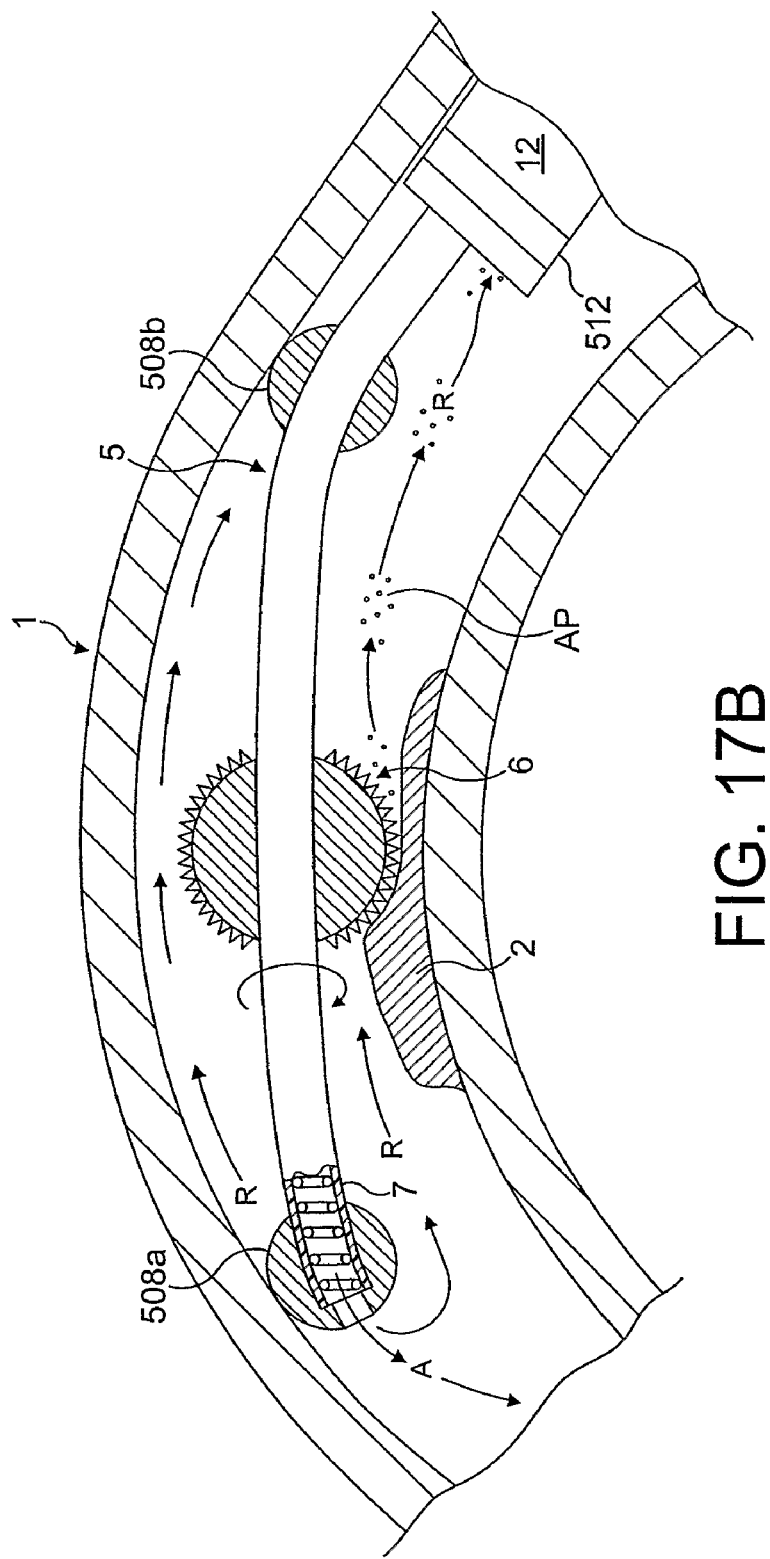
Figure 18A:
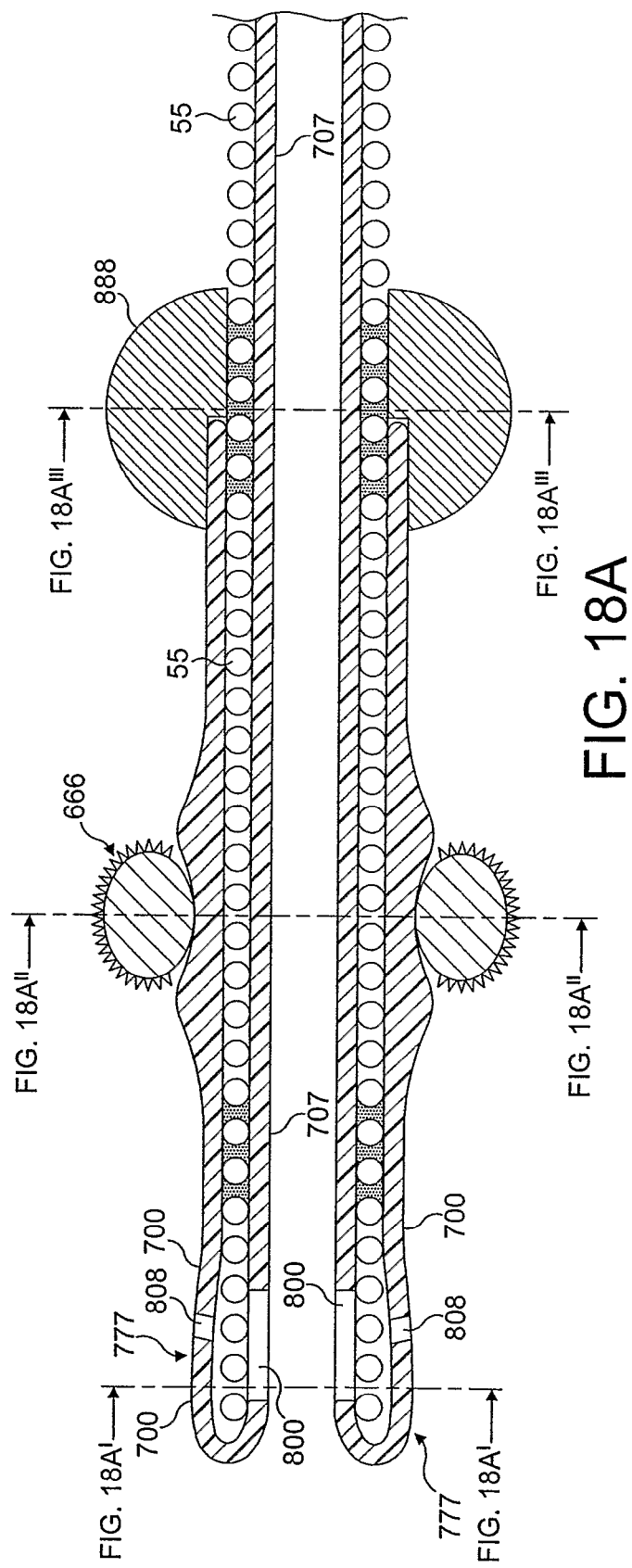
Figure 18B:
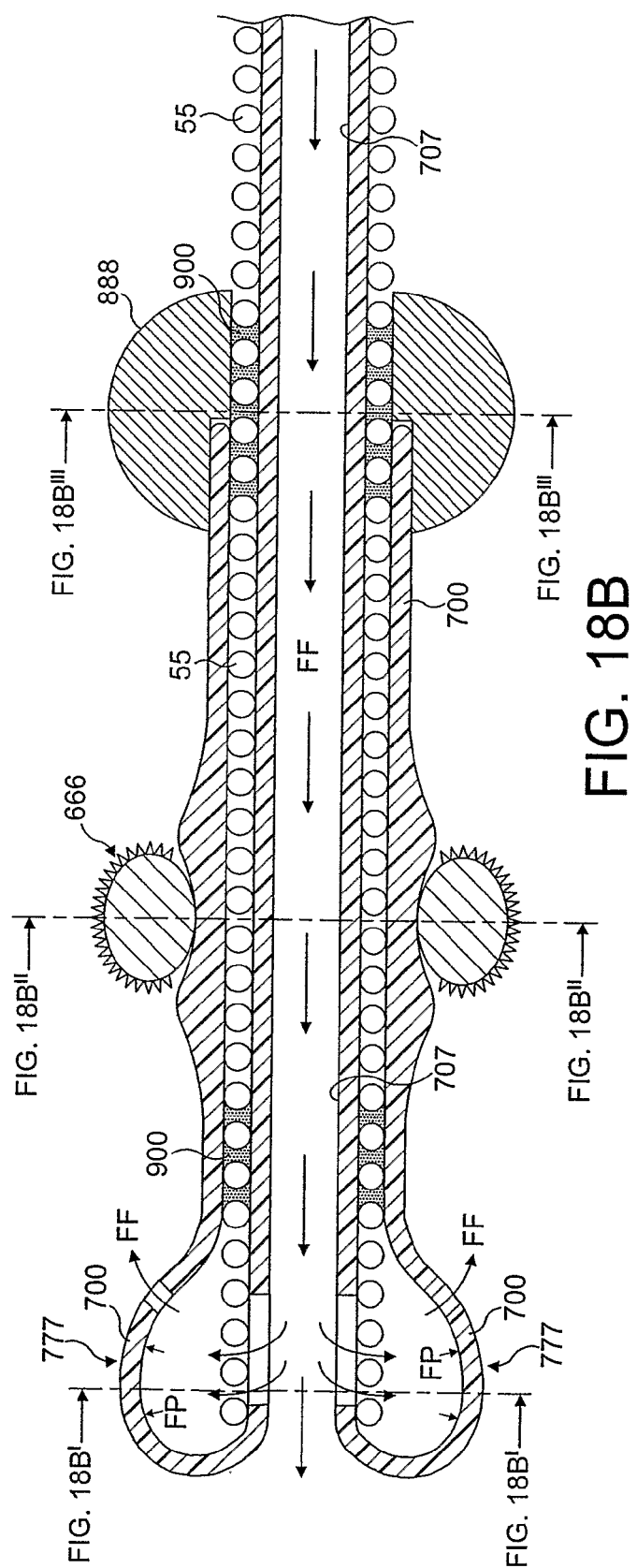
Figure 18D:
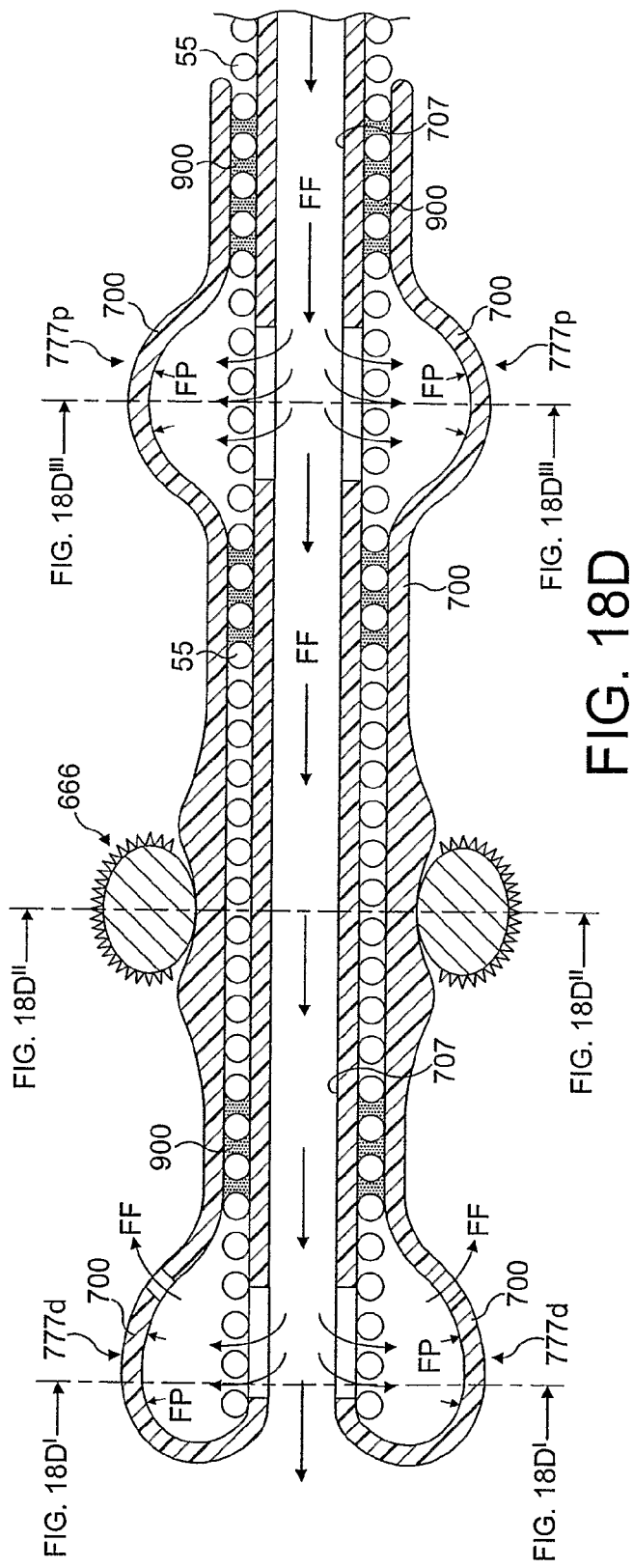
Figure 18E:
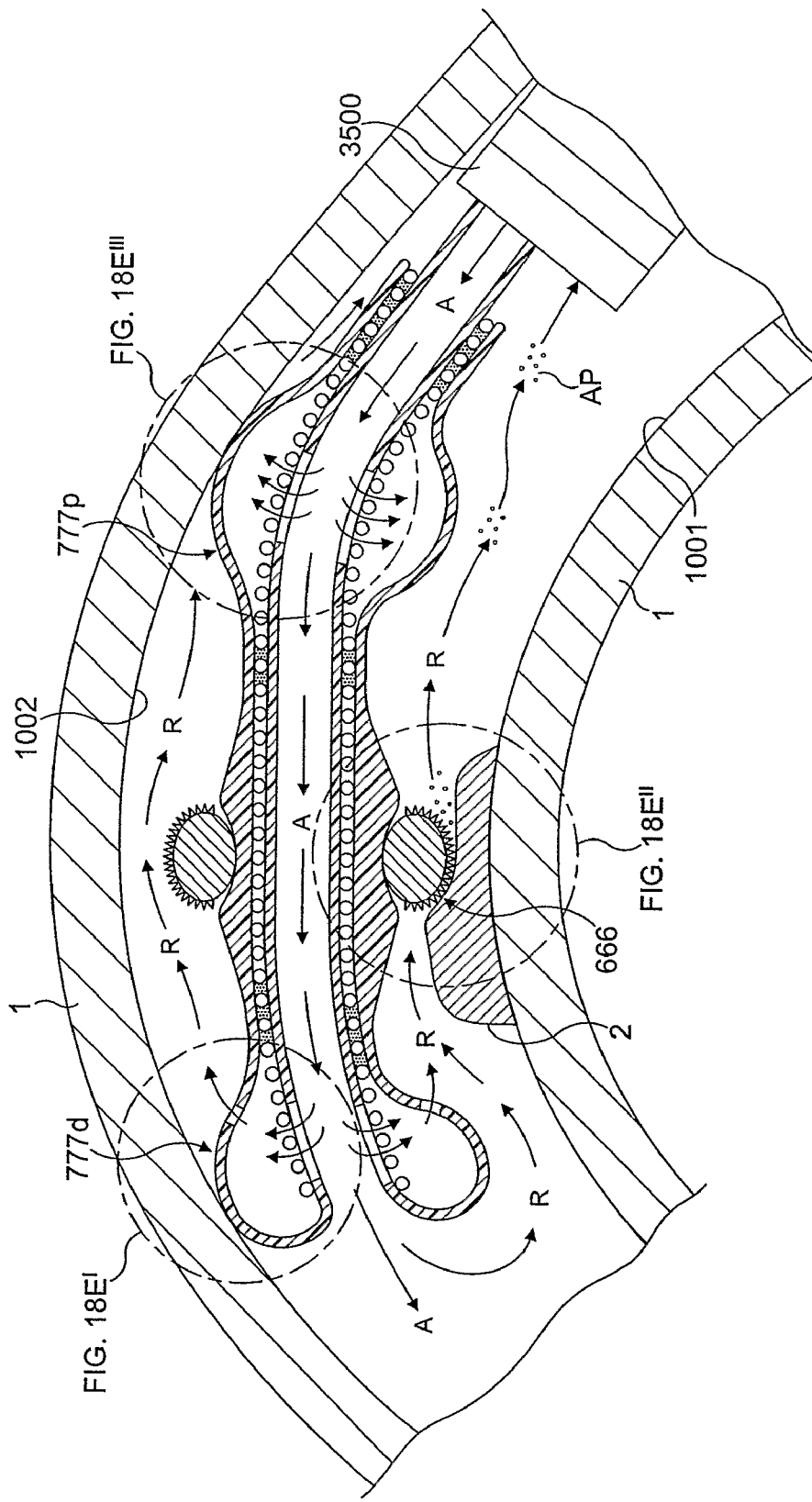
Figure 18F:
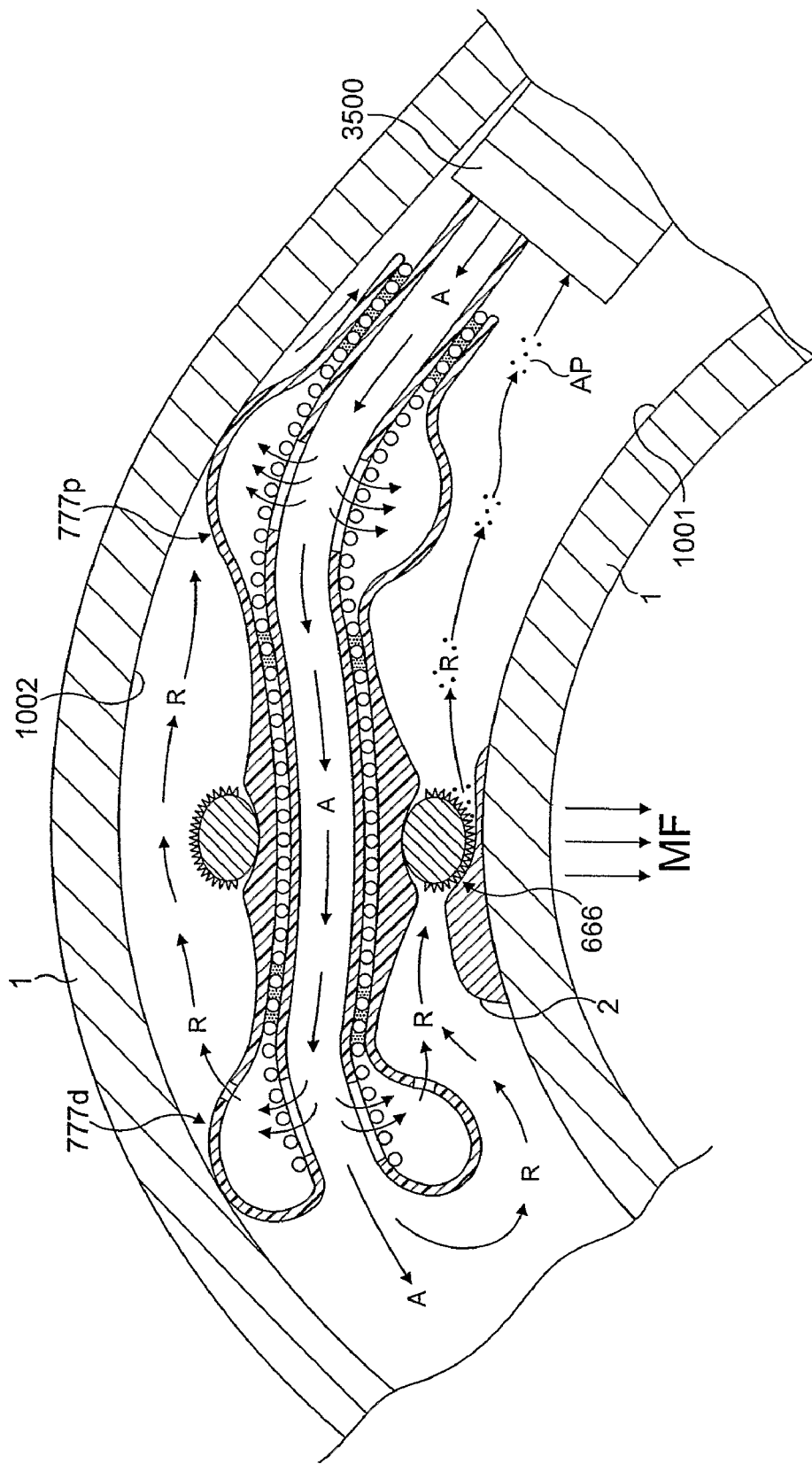
Figure 19C:
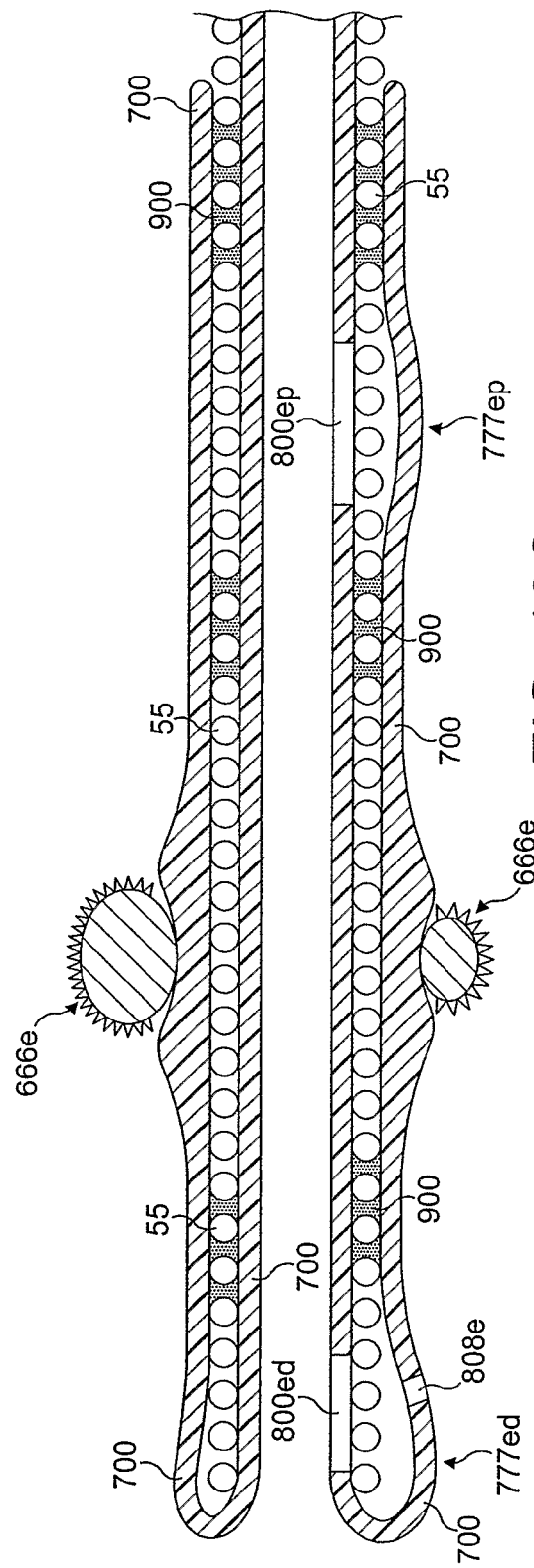
Figure 19E:
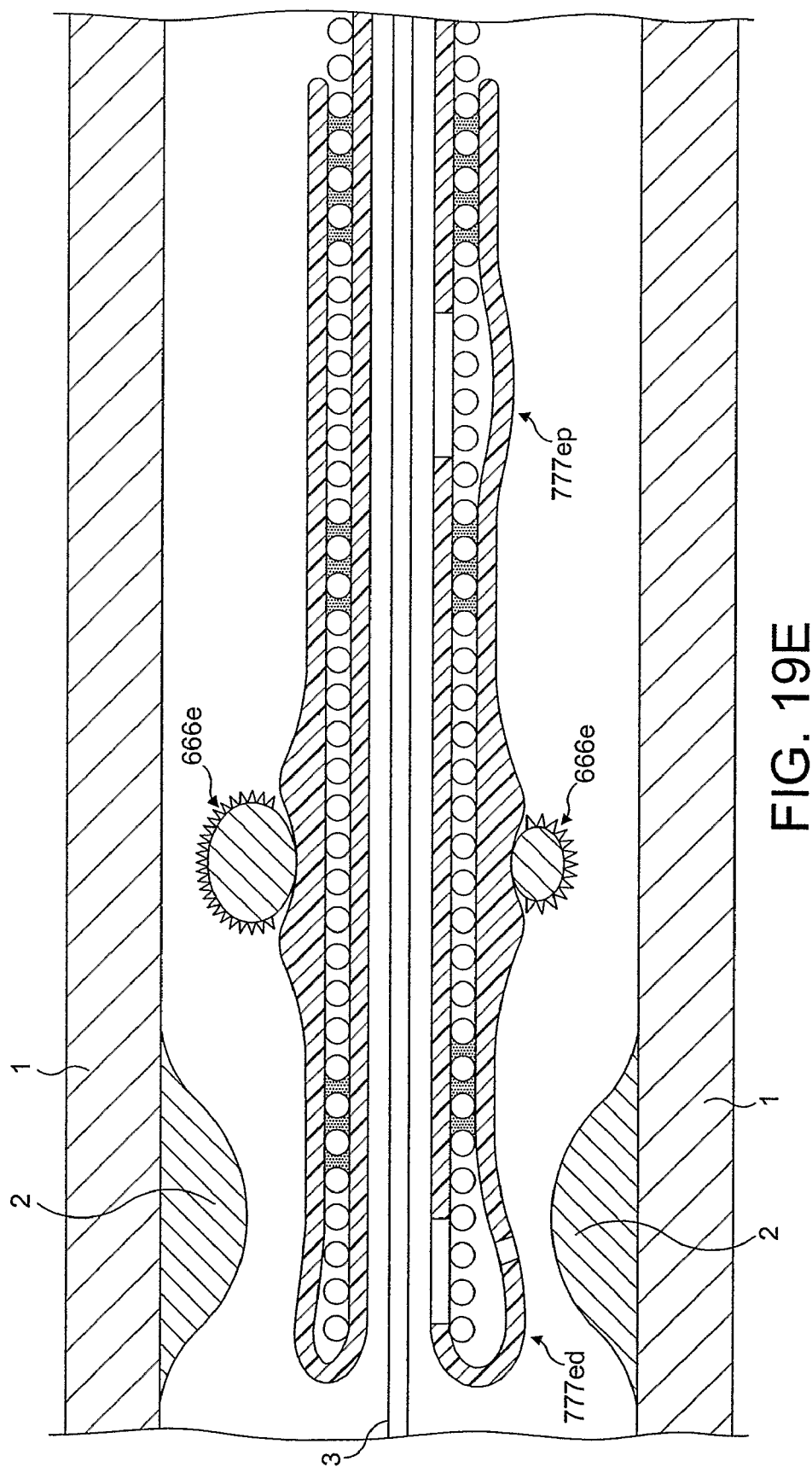
Figure 19F:
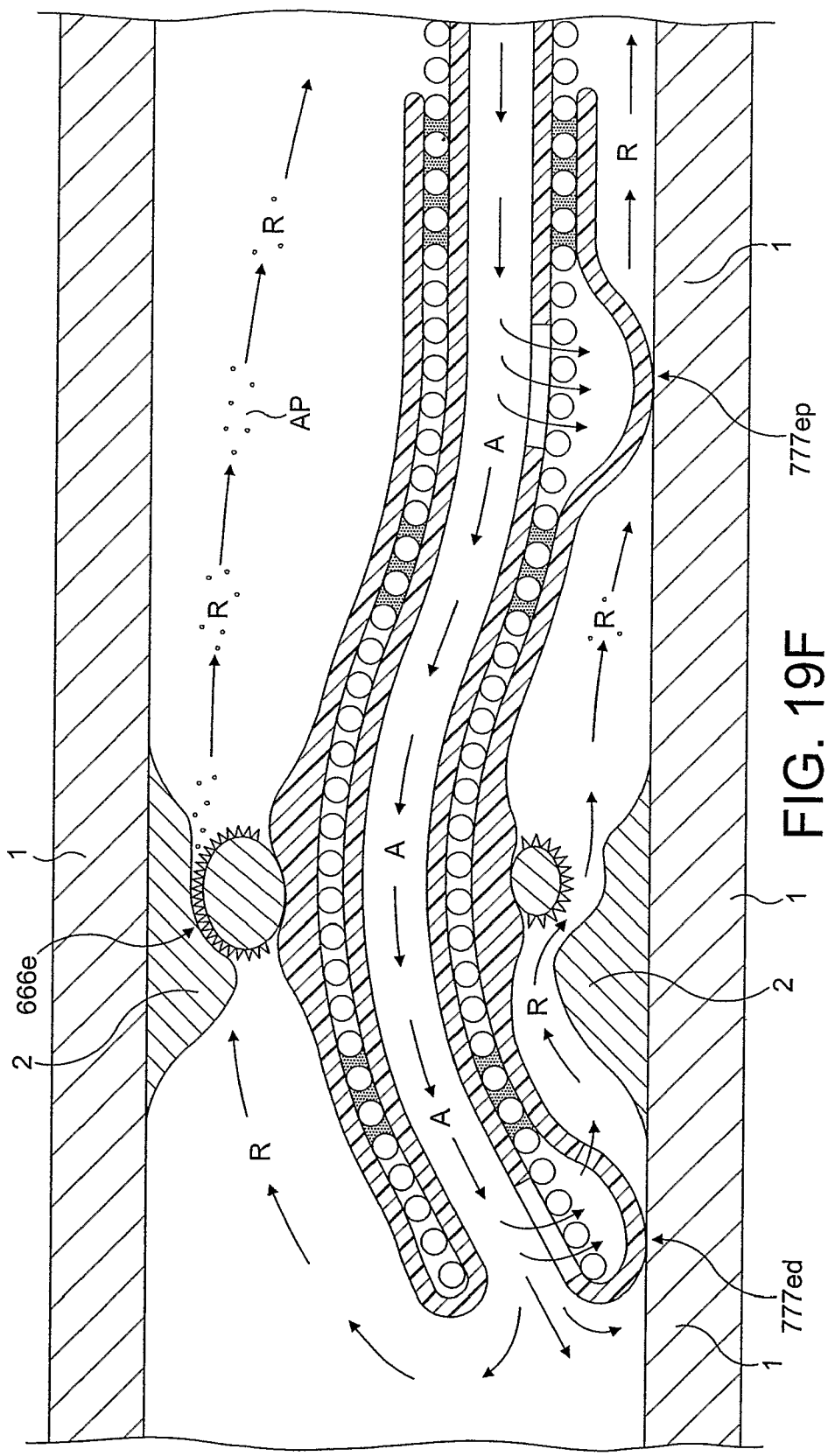
Figure 20A:
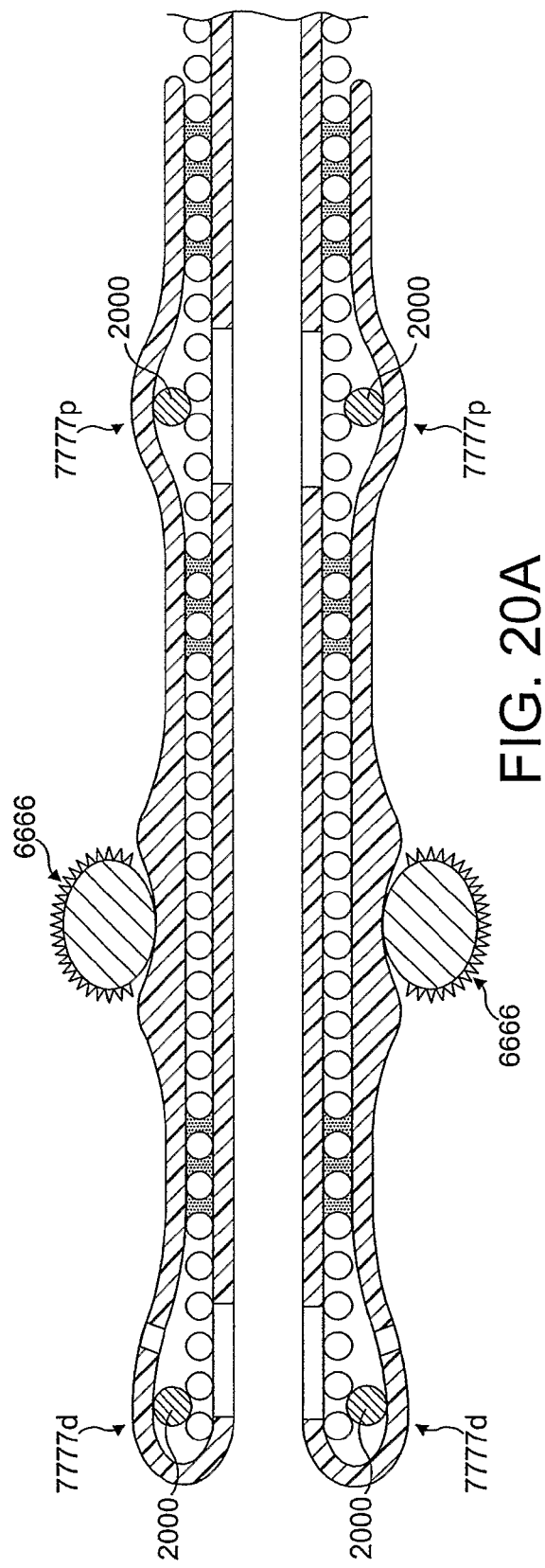
Figure 21A:
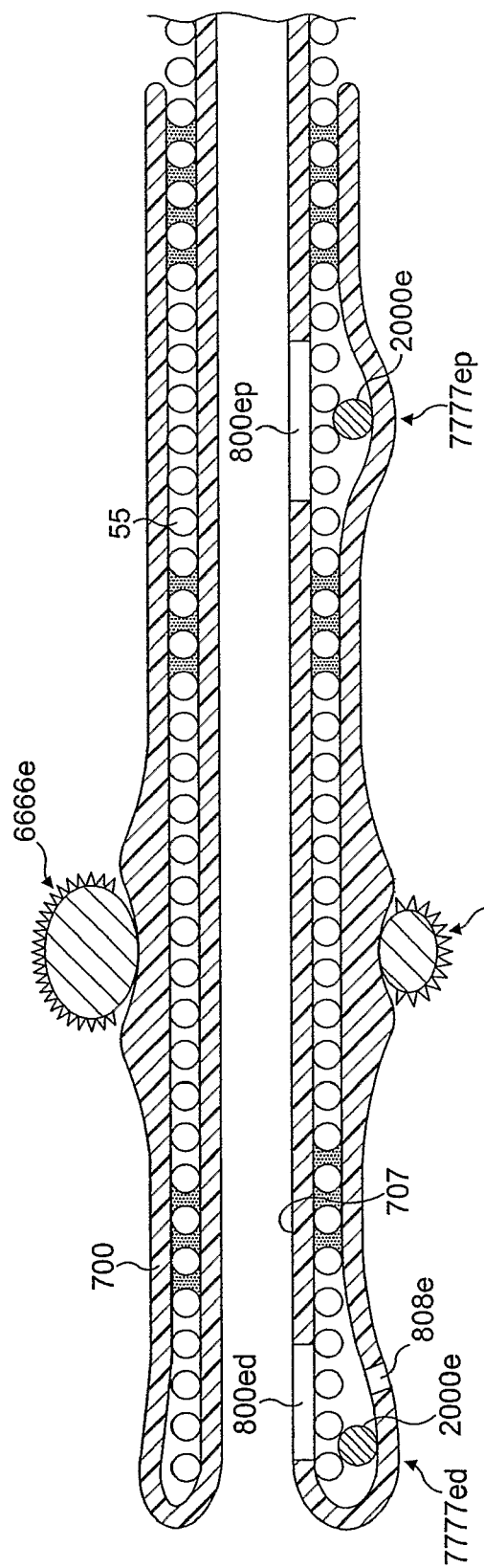
Figure 21B:
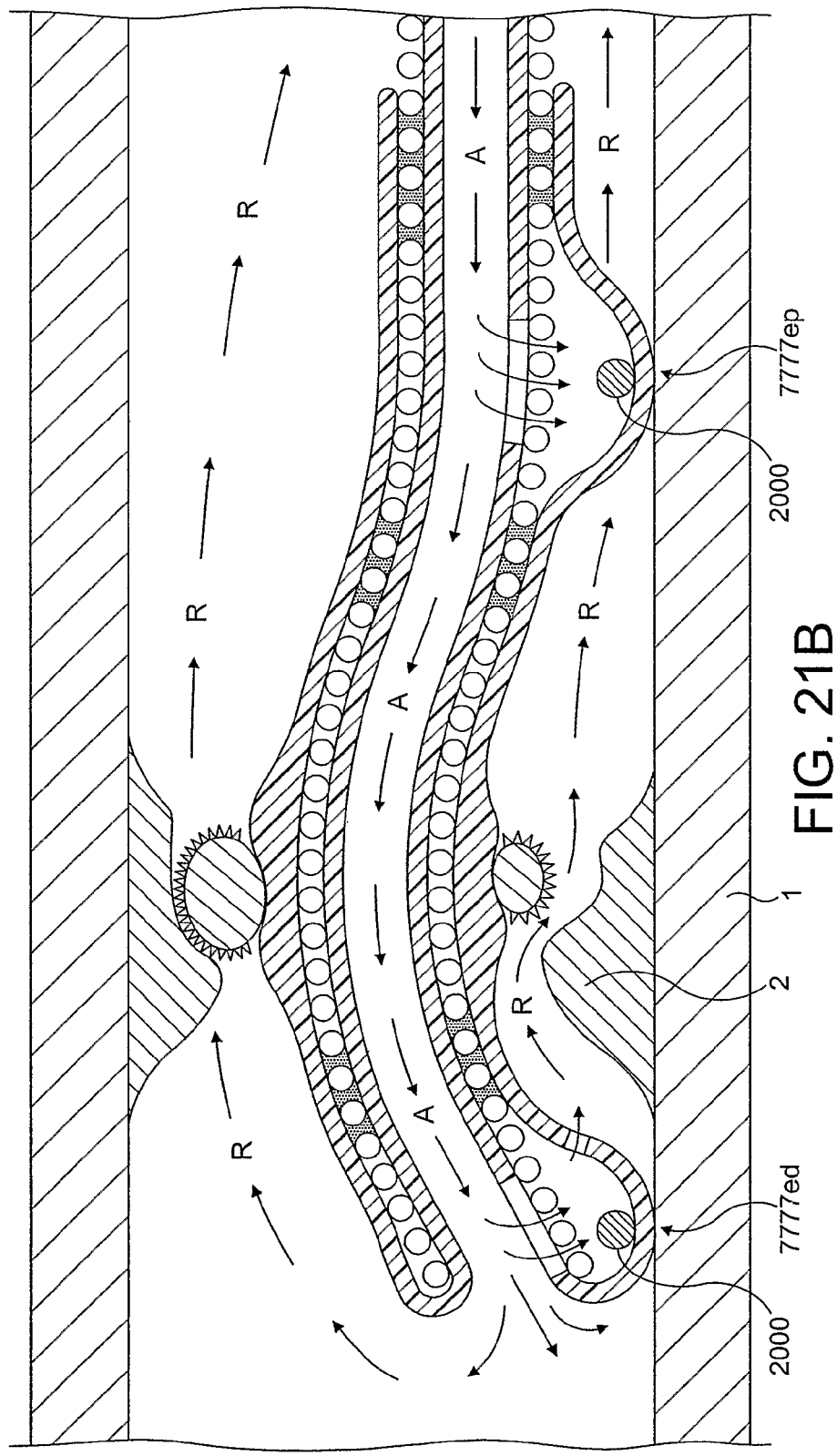
Figure 23:
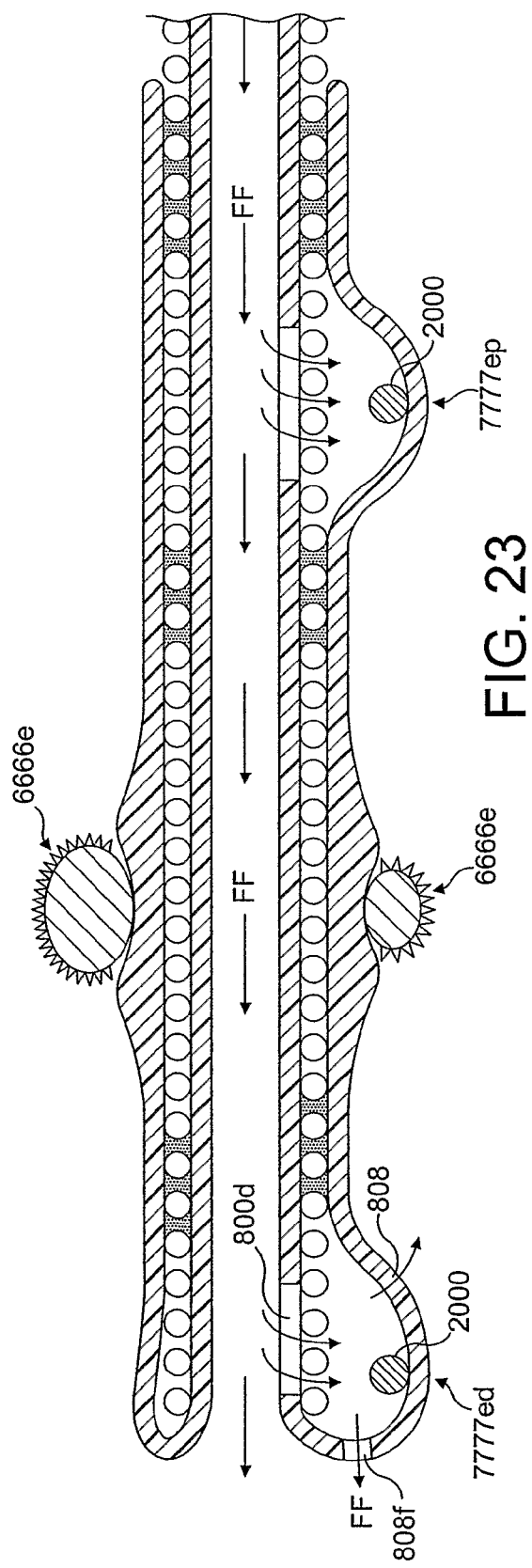
Figure 25A:
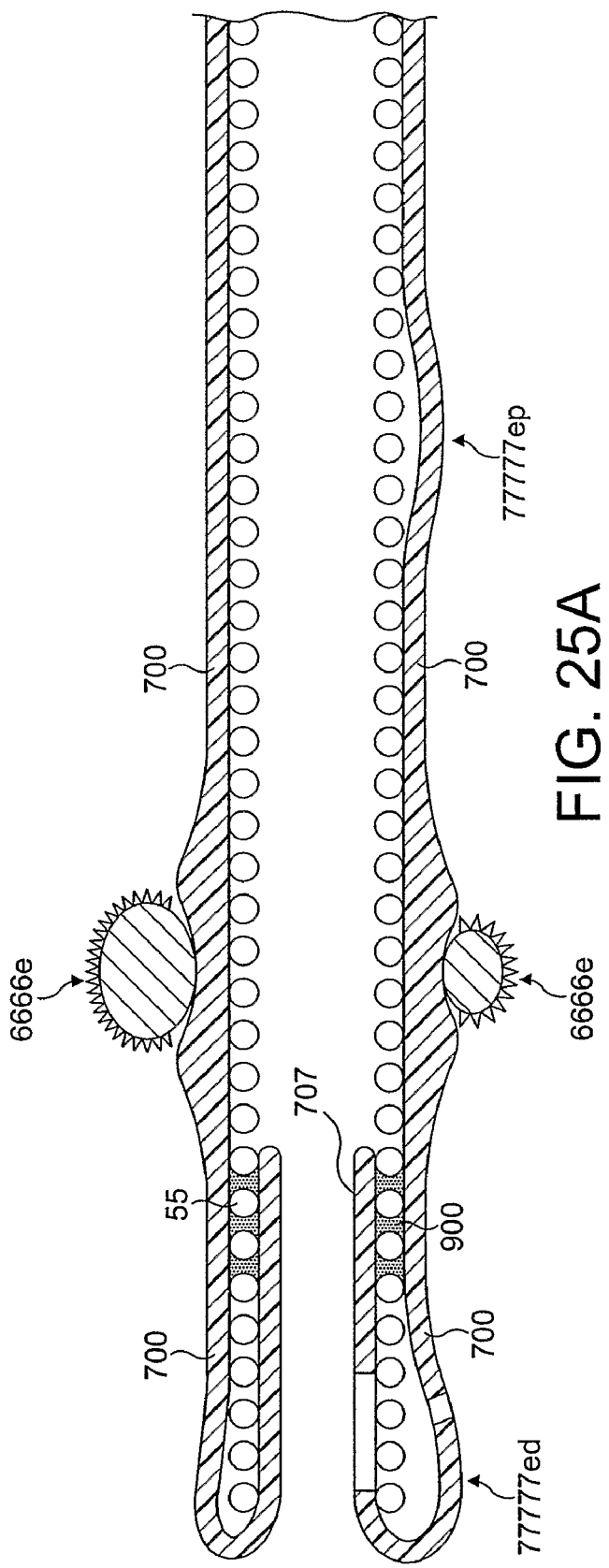
Figure 26A:
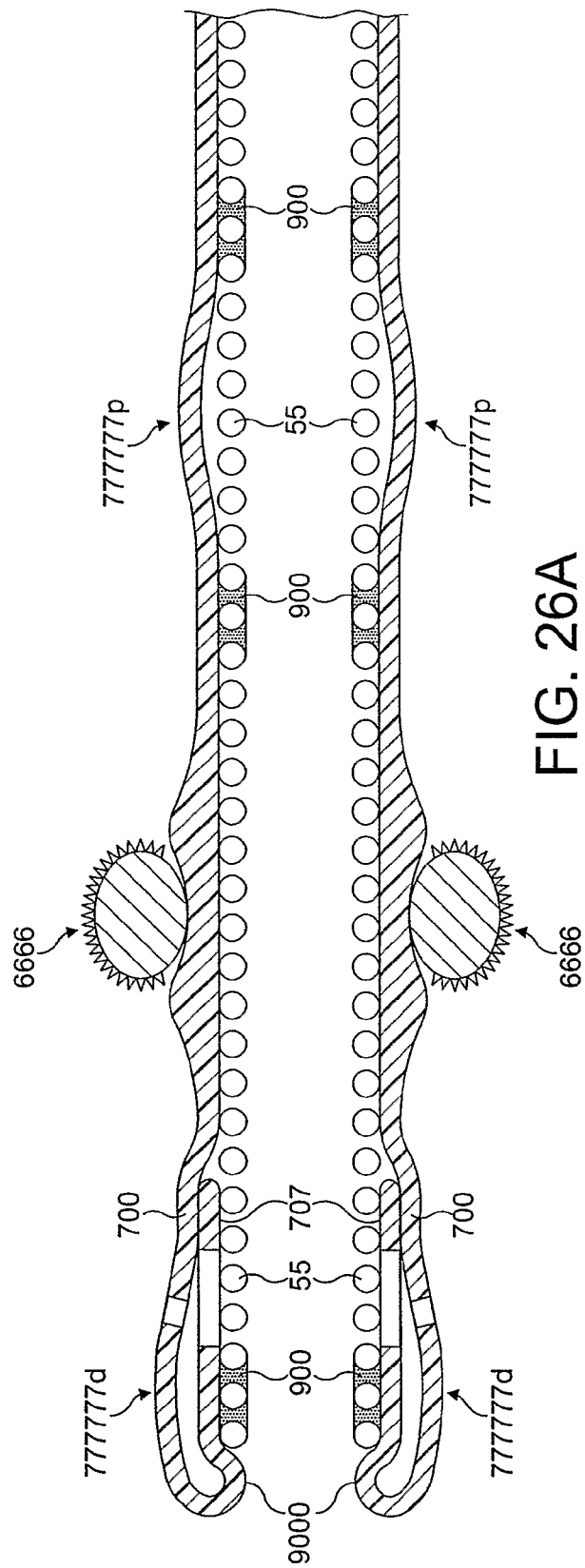
Figure 26B:
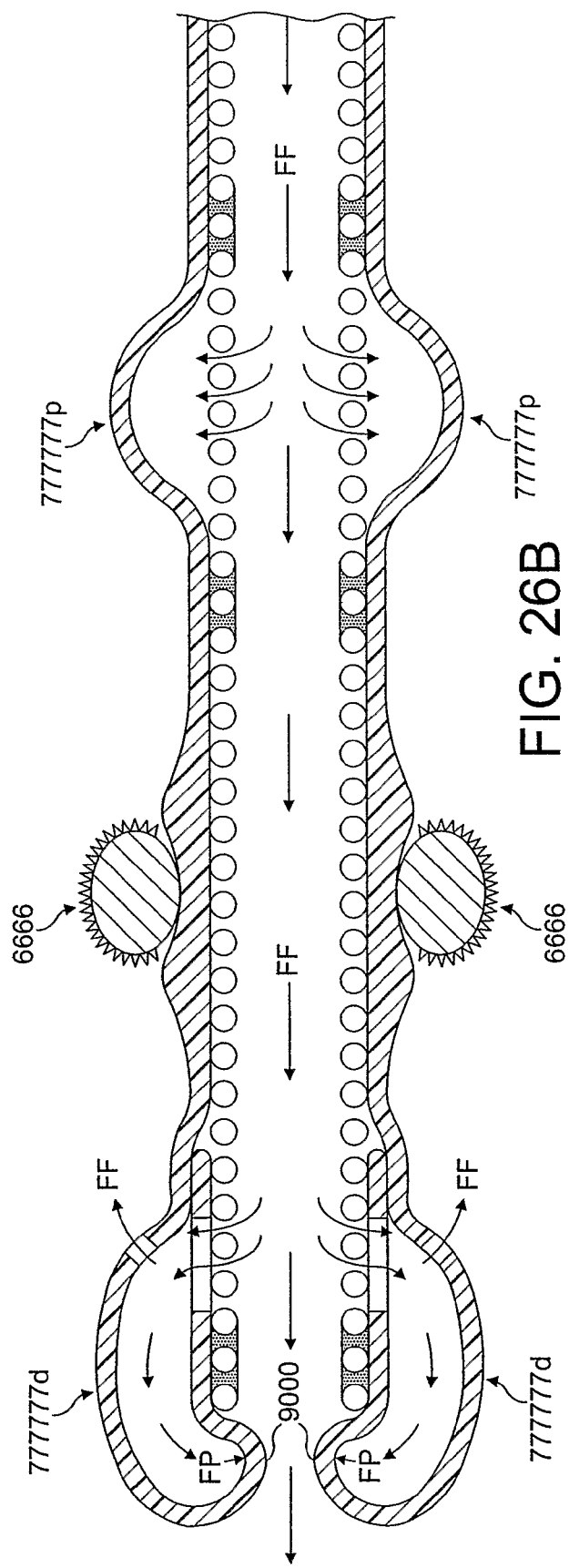
Figure 27:
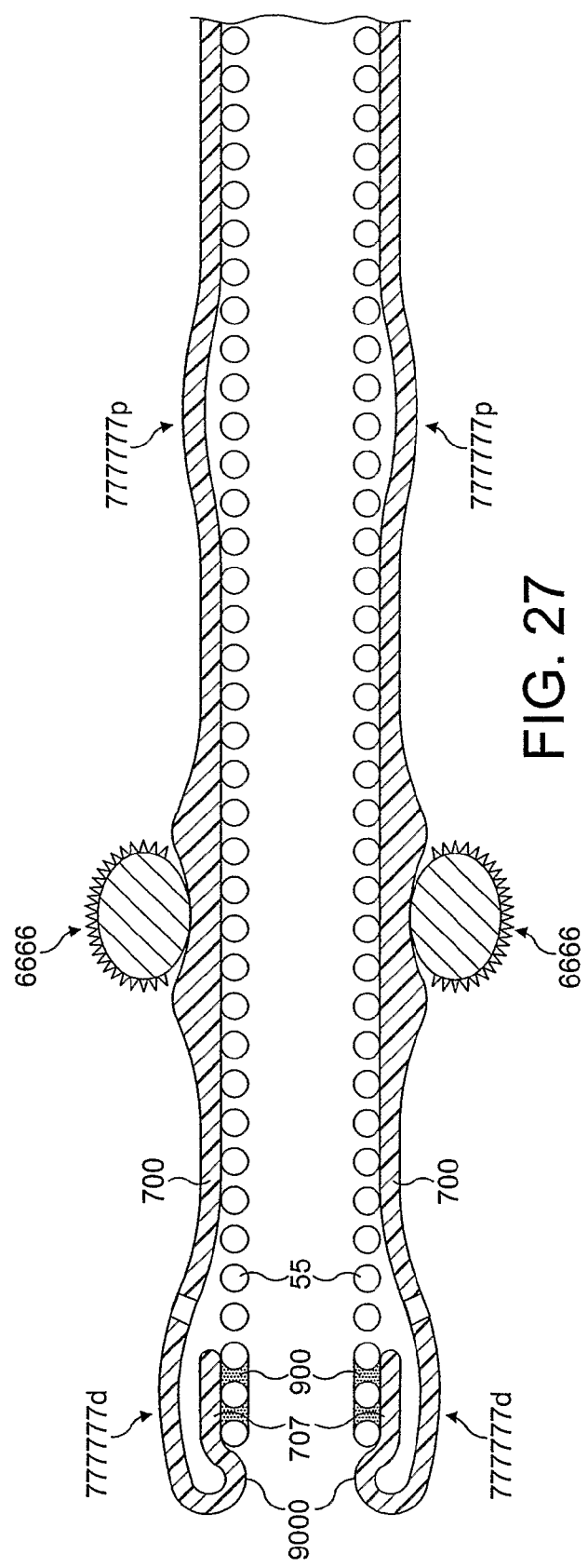

FIG. $2^I$ to FIG. $2^V$ show various enlarged cross-sectional views along the length of the drive shaft shown in FIG. 2 to primarily illustrate that the outer layer of the drive shaft is a monofibre or multifibre metal coil;

FIG. 3 is the same view of FIG. 2 showing withdrawal and removal of the guidewire from the vessel and the drive shaft before rotation thereof;

FIG. 4A is the same view as FIG. 2 and FIG. 3 but with the guidewire removed from the rotational atherectomy device and a straight stationary fluid supply tube advanced into the rigid, hollow, bearing supported shaft and the proximal end section of the flexible drive shaft, the flushing fluid is being pumped in an antegrade direction into the lumen of the fluid impermeable drive shaft and retrograde flow of at least a portion of the flushing fluid around the abrasive element has been established;

FIG. 4B is similar to FIG. 4A, except that it illustrates that a supply of compressed gas to the turbine has been initiated in order to initiate rotation of the drive shaft and the abrasive element;

FIG. 5A is similar to FIG. 4A, except that the fluid supply tube has been introduced only into the hollow, rigid, bearing supported shaft;

FIG. 5B is similar to FIG. 4B except that the fluid supply tube has been introduced only into the hollow, rigid, bearing supported shaft;

FIG. $5B^I$ to FIG. $5B^{III}$ is a series of drawings to show how the rotating abrasive element of the atherectomy device of the invention shown in FIG. 5 is repeatedly moved across the stenotic lesion in distal and proximal directions to remove a thin layer of stenotic lesion with each pass of the abrasive element across the stenotic lesion;

FIG. 6A is similar to FIG. 5A except that it illustrates the use of a multi-lumen drive shaft sheath;

FIG. 6B is similar to FIG. 5B, except that it illustrates the use of a multi-lumen drive shaft sheath;

FIG. 7 is substantially similar to FIG. 6B, except that it illustrates an inflatable element located at or near the distal end of the drive shaft sheath;

FIG. $7^I$ to FIG. $7^{III}$ is a series of drawings to show how the rotating abrasive element of the atherectomy device of the invention shown in FIG. 7 is repeatedly moved across the stenotic lesion in distal and proximal directions to remove a thin layer of stenotic lesion with each pass of the abrasive element across the stenotic lesion;

FIG. 8A illustrates, in a longitudinal cross-section, the attachment of the flushing fluid supply tube coupling member to the bearing support housing;

FIG. 8B is similar to FIG. 8A, except that it illustrates a different design of the flushing fluid supply tube coupling member and its attachment to the bearing support housing;

FIG. 9A is similar to FIG. 8A, except that it illustrates an optical rotational speed sensing mechanism for determining the rotational speed of the drive shaft;

FIG. 9B is similar to FIG. 8B, except that it illustrates an optical rotational speed sensing mechanism for determining the rotational speed of the drive shaft;

FIGS. 10 to 12 illustrate alternative means for connecting the flushing fluid supply tube to the rigid, hollow, bearing supported shaft, the flushing fluid supply tube in this embodiment being rotatable together with the rigid, hollow, bearing supported shaft by a prime mover which is remotely located with respect to the flushing fluid supply tube and the bearing support housing, the flushing fluid being pumped into the flushing fluid supply tube by a centrifugal pump(s) of one or more design;

FIG. 13A illustrates an enlarged side-sectional view of a portion of the distal end section of the fluid impermeable drive shaft showing the abrasive element mounted thereon, the fluid impermeable lining of the drive shaft extending distally proximal to the distal end of the drive shaft and distal to the abrasive element;

FIG. 13B is similar to FIG. 13A, except that the fluid impermeable lining of the drive shaft terminates distally in an area corresponding to the location of the abrasive element;

FIG. 14 is similar to FIG. 13B, except that it shows a modified abrasive element;

FIGS. 15 to 16C illustrate two types of abrasive elements together with two types of mounting of said abrasive elements around the distal end section of the fluid impermeable drive shaft;

FIG. 17A illustrates, in a longitudinal cross section, the distal end portion of the fluid impermeable drive shaft with two support elements mounted around the drive shaft on either side of the abrasive element, both elements being spaced away from the abrasive element;

FIG. 17B is similar to FIG. 17A except that it illustrates how the support elements allow the biasing of the abrasive element towards the inner curvature of a curved vessel to be treated;

FIG. 18A is similar to FIG. 17A except that it illustrates that the distal support element is formed by the fluid impermeable membrane whilst the proximal support element is solid;

FIG. $18A^I$ is a cross sectional view through the distal inflatable element shown in FIG. 18A prior to inflation, the distal inflatable element having a small crossing diameter by being made out of furled or folded non-stretchable membrane;

FIG. $18A^{II}$ is a cross sectional view through the abrasive element shown in FIG. 18A and illustrates its fixation on the drive shaft;

FIG. $18A^{III}$ is a cross sectional view through the proximal solid support element and illustrates its fixation on the drive shaft;

FIG. 18B is similar to FIG. 18A, except that the inflatable distal support element has been inflated and the direction of flow of flushing fluid is changed from antegrade to retrograde as it passes from the lumen of the drive shaft into the vessel through the distal inflatable support element;

FIG. $18B^I$ is a cross sectional view through the inflated inflatable element shown in FIG. 18B and illustrates how fluid pressure maintains inflatable element in a distended state;

FIG. $18B^{II}$ is a cross sectional view through the abrasive element shown in FIG. 18B and illustrates its fixation on the drive shaft;

FIG. $18B^{III}$ is a cross sectional view through the proximal solid support element shown in FIG. 18B and illustrates its fixation on the drive shaft;

FIG. 18C is similar to FIG. 17A, except that it illustrates inflatable support elements formed by the fluid impermeable membrane;

FIG. $18C^I$ is a cross sectional view through the distal inflatable element shown in FIG. 18C prior to inflation, the distal inflatable element having a small crossing diameter by being made out of furled or folded non-stretchable membrane;

FIG. $18C^{II}$ is a cross sectional view through the abrasive element shown in FIG. 18C and illustrates its fixation on the drive shaft;

FIG. $18C^{III}$ is a cross sectional view through is a cross sectional view through the proximal inflatable element shown in FIG. 18C prior to inflation, the proximal inflatable element having a small crossing diameter by being made out of furled or folded non-stretchable membrane;

FIG. 18D is similar to FIG. 18C, except that it illustrates that both distal and proximal inflatable support elements being inflated;

FIG. $18D^I$ is a cross sectional view through the distal inflated inflatable elements shown in FIG. 18D and illustrates how fluid pressure maintains the distal inflatable element in a distended state;

FIG. $18D^{II}$ is a cross sectional view through the abrasive element shown in FIG. 18D and illustrates its fixation on the drive shaft;

FIG. $18D^{III}$ is a cross sectional view through the proximal inflated inflatable element shown in FIG. 18D and illustrates how fluid pressure maintains the proximal inflatable element in a distended state;

FIG. 18E is similar to FIG. 18D, except that it illustrates the use of the fluid inflatable support elements and advantage of establishing retrograde flushing fluid flow through an opening(s) in a distal fluid inflatable support element;

FIG. $18E^I$ is an enlarged view of a portion of the inflatable element shown in FIG. 18E showing that the membrane of the distal inflatable element is in contact with the inner surface of the outer curvature of the vessel;

FIG. $18E^{II}$ is an enlarged view of a portion of the device shown in FIG. 18E to illustrates how rotating abrasive element is biased to and preferentially removes stenotic tissue along inner curvature of the treated vessel;

FIG. $18E^{III}$ is an enlarged view of a portion of the proximal inflatable element shown in FIG. 18E showing that the membrane of the proximal inflatable element is in contact with the inner surface of the outer curvature of the vessel;

FIG. 18F is similar to FIG. 18E, except that it illustrates a bias provided to the abrasive element by a magnetic force or forces, illustrated by arrows marked "MF";

FIG. 19A is similar to FIG. 18A, except that it illustrates eccentrically mounted abrasive element and a fluid inflatable distal counterweight while proximal counterweight is solid;

FIG. $19A^I$ is a cross sectional view through the distal inflatable counterweight shown in FIG. 19A prior to inflation, the distal inflatable counterweight having a small crossing diameter by being made out of furled or folded non-stretchable membrane;

FIG. $19A^{II}$ is a cross sectional view through the eccentric abrasive element shown in FIG. 19A and illustrates its fixation on the drive shaft;

FIG. $19A^{III}$ is a cross sectional view through the proximal solid counterweight and illustrates its fixation on the drive shaft;

FIG. 19B is similar to FIG. 19A, except that the inflatable distal support counterweight has been inflated and the direction of flow of flushing fluid is changed from antegrade to retrograde as it passes from the lumen of the drive shaft into the vessel through the distal inflatable counterweight;

FIG. $19B^I$ is a cross sectional view through the inflated inflatable counterweight shown in FIG. 19B and illustrates how fluid pressure maintains the distal inflatable counterweight in a distended state;

FIG. $19B^{II}$ is a cross sectional view through the eccentric abrasive element shown in FIG. 19B and illustrates its fixation on the drive shaft;

FIG. $19B^{III}$ is a cross sectional view through the proximal solid counterweight shown in FIG. 19B and illustrates its fixation on the drive shaft;

FIG. 19C shows a fluid impermeable drive shaft with eccentric abrasive element and fluid inflatable distal and proximal counterweights both of which are shown in a deflated state;

FIG. 19D is similar to FIG. 19C, except that the fluid inflatable counterweights are both shown in an inflated state. It also shows how the direction of fluid flow is changed from antegrade to retrograde as it passes from the drive shaft lumen into the vessel through the distal inflatable counterweight;

FIG. 19E shows advancement of the fluid impermeable drive shaft having inflatable counterweights across the stenotic lesion to be treated;

FIG. 19F illustrates the device shown in FIG. 19D being rotated and curved by centrifugal forces created by rotating eccentric abrasive element and rotating counterweights;

FIG. 20A shows rounded radiopaque markers disposed within the fluid inflatable support elements;

FIG. 20B is similar to FIG. 20A, except that it shows the fluid inflatable element being inflated and rounded radiopaque markers disposed within the fluid inflatable support elements being moved in a radially outward direction within the fluid inflatable support elements by centrifugal forces generated by the rotating drive shaft;

FIG. 21A shows radiopaque markers disposed within the fluid inflatable counterweights;

FIG. 21B, illustrates the use of the device similar to that shown in FIG. 19F but having rounded radiopaque markers disposed within the fluid inflatable counterweights;

FIG. 22 is similar to FIG. 20B, except that the distal fluid inflatable support element has one or more additional openings for providing antegrade flow of flushing fluid through said openings out of the fluid inflated distal support element;

FIG. 23 is similar to FIG. 22, except that it shows an eccentric abrasive element and eccentric counterweights, the distal fluid inflatable counterweight having one or more additional openings for providing antegrade flow of flushing fluid through said openings out of the fluid inflated distal counterweight;

FIG. 24A to FIG. 25B show how proximal fluid inflatable support elements or counterweights may be formed by a fluid impermeable membrane extending along said proximal support elements or counterweights only around the torque transmitting layer of the drive shaft; and FIG. 26A to FIG. 27 are generally similar to FIG. 24A to FIG. 25B and illustrate formation of circumferential inwardly distendable lip at the distal end of the distal inflatable support element or counterweight.

DETAILED DESCRIPTION OF EMBODIMENTS

Although the invention will be described primarily with reference to atherectomy procedures in coronary or peripheral arteries, it will be appreciated that the device and method according to the invention can also be used for the treatment of stenosis in coronary bypass grafts as well as for the treatment of restenosis. The device may also be useful for treatment of in stent restenosis as well as for restoring patency of arteriovenous shunts, particularly shunts formed from expanded polytetrafluoroethylene.

Reference is made to "distal" and "proximal" ends and to flow of fluid in an "antegrade" and "retrograde" direction. For the avoidance of doubt, and for the purpose of this specification, the distal end is considered to refer to the end of the device which is inserted into the vessel in the body of the patient and the proximal end is the end of the device which remains outside the body of the patient and is connected to a handle assembly for both rotating and longitudinally moving the drive shaft within the treated vessel. Antegrade flow refers to a direction of flow from the proximal towards the distal end of the device. Similarly, retrograde flow refers to a direction of flow in the opposite direction, i.e. from the distal to the proximal end of the device.

Figure 1:
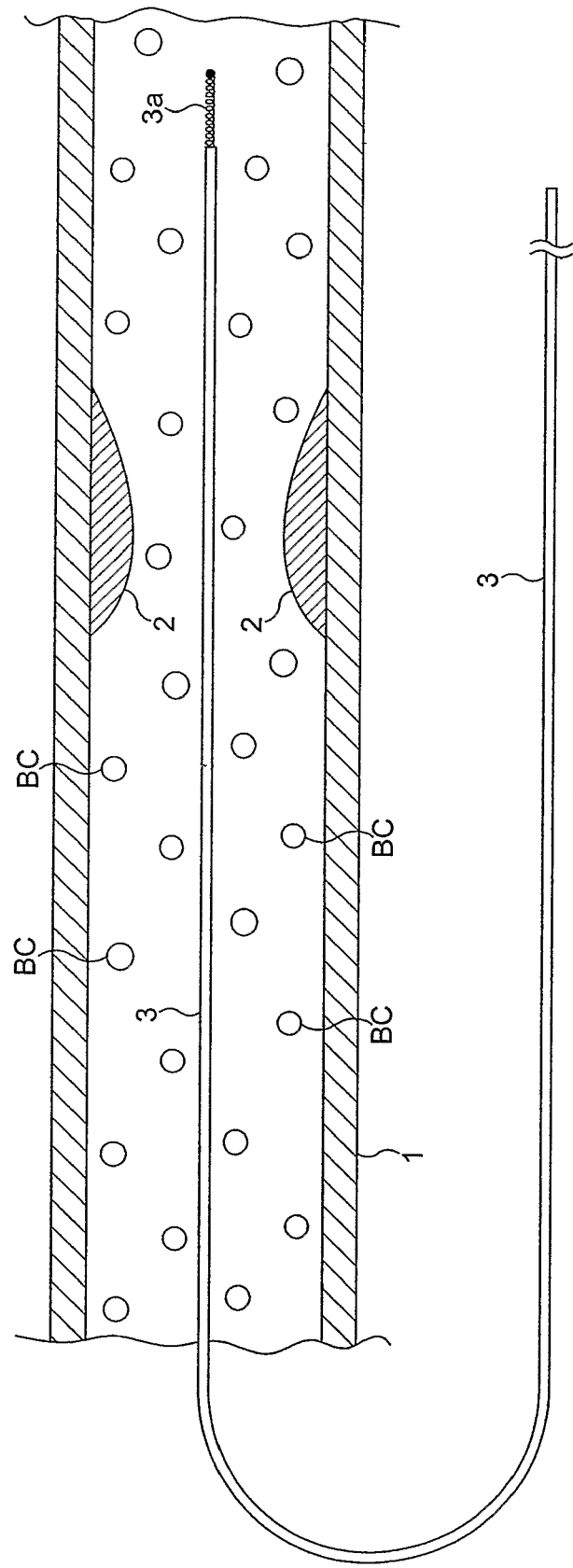
FIG. 1 is a sectional side elevation of a portion of a blood vessel containing a stenotic lesion and in which a guidewire is located.

FIG. 1 illustrates a side sectional view of a portion of a blood vessel 1 which has been partially occluded by the presence of a stenotic lesion 2. Blood flow along the treated vessel is illustrated by blood cells BC in FIGS. 1, 2 and 3. Such stenotic lesion 2 in the patient's vessel has to be treated and may be partially or wholly removed using the rotational atherectomy device according to any one of the embodiments of the invention. Once the location of the stenotic lesion has been ascertained and a decision to use the atherectomy device of the invention is made, then a conventional guidewire 3 is placed, using conventional angioplasty techniques, in the vessel 1 to be treated. As shown in FIG. 1, the guidewire 3 is placed across the stenotic lesion 2 and its distal end 3a is located in the vessel 1 distally to the stenotic lesion 2. The proximal end of the guidewire 3 extends proximally out of the patient's body.

Once the distal end 3a of the guidewire 3 has been located in the appropriate position distal to the stenotic lesion 2, the distal end 4 of a flexible hollow drive shaft 5 is advanced over the proximal end of the guidewire 3 protruding from the patient and is tracked over the guidewire 3 until an abrasive element 6, mounted on the drive shaft 5 a short distance proximal to the distal end 4 of the drive shaft 5, is situated close to the stenotic lesion 2 to be abraded. The drive shaft 5 is shown in this position in FIG. 2.

In the conventional rotational atheretomy (angioplasty) device produced by Boston Scientific Corporation of Massachusets, USA and, in the orbital atherectomy device produced by Cardiovascular Systems, Inc. of Minnesota, USA, the flexible hollow drive shaft is formed from at least one helically coiled wire, and is disposed within a lumen of a hollow tubular sheath (drive shaft sheath) which extends around the hollow drive shaft. In these devices, flushing fluid is pumped into an annular lumen formed between the drive shaft and the sheath surrounding it. The flushing fluid is then able to flow between adjacent turns of said helically coiled wires from the annular lumen of the drive shaft sheath into the lumen of the hollow drive shaft and vice-versa.

In a preferred embodiment of the invention, the flexible hollow drive shaft is formed from at least one helically coiled wire 55 and the fluid impervious membrane 7 which prevents flow of fluid out from a lumen of the drive shaft between adjacent turns of said helically coiled wire. In one such embodiment shown in FIG. 13A, the fluid impervious membrane 7 terminates distally proximal to the distal end of the drive shaft 5 but distal to the abrasive element 6 to allow the flow of fluid between adjacent turns of said helically coiled wire 55 from the drive shaft lumen 5a into a portion of the vessel which is located distal to the abrasive element. In this embodiment, the luminal openings in the drive shaft 5 are formed by the space or spaces between the turns of the coiled wire or wires 55 through which fluid may pass from the drive shaft lumen 5a into said portion of the vessel which is located distal to the abrasive element 6.

FIG. $2^I$ to FIG. $2^V$ show various enlarged cross-sectional views along the length of the drive shaft shown in FIG. 2 to primarily illustrate that the outer layer of the drive shaft 5 is a monofibre or multifibre metal coil 55.

FIGS. 13B and 14 show that the fluid impervious membrane 7 may terminate within the abrasive element 6. In this case, the entire portion of the drive shaft or that portion of the drive shaft 5 which is proximal to the abrasive element 6 has to be fluid impermeable, thereby preventing flushing fluid pumped along the fluid impermeable drive shaft lumen 5a from being transmitted through the wall of the drive shaft into a portion of the vessel which is located proximal to the abrasive element.

The fluid impervious membrane may line the inside of the hollow drive shaft or, as shown in FIG. 17B, the fluid impervious membrane 7 may cover the outside of the drive shaft 5.

FIGS. 2 through 7 and FIGS. 17A and 17B show that the whole of the drive shaft may be fluid impermeable, in which case the luminal opening is the opening at the distal end 4 of the fluid impermeable drive shaft 5.

In the most preferred embodiment of the invention, the torque transmitting layer of the drive shaft 5 is formed from multiple helically coiled wires 55 to give the drive shaft longitudinal flexibility and torsional rigidity which is required to enable it to be advanced through the patient's often tortuous arteries to reach the stenotic lesion 2 and to enable the drive shaft to be rotated at very high speeds without breaking.

Although the torque transmitting layer of the drive shaft 5 is preferably formed from at least one helically coiled wire, it is also envisaged that the drive shaft 5 could be formed without use of helically coiled wire(s) from a fluid impervious material or combination of materials or material layers which have sufficient longitudinal flexibility and torsional rigidity to cope with the forces that are applied to the drive shaft 5 during rotation.

As illustrated in FIG. 2, the abrasive element 6 takes the form of a rounded eccentric mass positioned a short distance proximal to the distal end 4 of the drive shaft 5. As illustrated in FIG. 13A onwards, the abrasive element 6 may be circular, oval or may have another shape in longitudinal cross-section and have an aperture 6a therein to enable it to be located around, the drive shaft 5. In many of the preferred embodiments, and regardless of the shape of the abrasive elements 6, its centre of mass is not coaxial with the longitudinal and/or rotational axis Y-Y of the drive shaft 5. The eccentricity of the mass of the abrasive element 6 causes it to orbit around the rotational axis Y-Y of the drive shaft 5 to create an opening in the stenotic lesion 2 which has a diameter much larger than the diameter of the abrasive element 6 itself. FIGS. 17A, 17B and many of the other Figures illustrate an abrasive element 6 mounted concentrically on the drive shaft 5. Certain advantages of concentrically mounting the abrasive elements 6 on the drive shaft 5 will be explained in more detail below.

If the centre of mass of the abrasive element 6 is offset from the longitudinal rotational axis of the drive shaft 5, then a pair of counterweights 8a,8b also having their centres of mass offset from the longitudinal or rotational axis of the drive shaft 5 may be mounted or otherwise formed on the drive shaft 5. Most preferably, such counterweights 8a,8b are spaced from and located on either side of the abrasive element 6, as shown in FIG. 2. The centre of mass of each counterweight 8a,8b is located in the same longitudinal plane as the centre of mass of the abrasive element 6 and diametrically opposite to the centre of mass of the abrasive element 6 with respect to the longitudinal axis of the drive shaft 5. In a preferred embodiment, the centre of mass of the, or each, counterweight 8a,8b is separated from the centre of mass of the abrasive element 6 by an angle of 180 degrees around the longitudinal axis of the drive shaft 5.

Although the counterweights 8a,8b shown in FIGS. 2 through 7 can be formed integrally with the drive shaft 5, it is preferable that, in these embodiments, they are formed separately to the drive shaft 5 and connected to it using adhesive or the like.

In at least one preferred embodiment, the abrasive element 6 is attached to a waisted portion 10 of the drive shaft 5, i.e. a part of the drive shaft 5 which has a smaller outer diameter than the remainder of the distal end portion of the drive shaft 5. Such an arrangement is illustrated in FIG. 13B and FIG. 14.

FIGS. 13B and 14 also show the lining 7 terminating at the waisted portion 10 of the drive shaft 5, i.e. at the point at which the abrasive element 6 is located on the drive shaft 5. Alternatively, the drive shaft 5 may exhibit at least one region 9 of increased diameter over a portion of its length close to its distal end. A circumferential groove, depression, seat or saddle 100 may be formed in the centre of the increased diameter region 9 and the abrasive element 6 may be located in this circumferential groove or seat 100 and so may be prevented from moving in a longitudinal or axial direction along the drive shaft 5. This arrangement is illustrated in FIGS. 15 and 16. Each end section 9a,9b of the increased diameter region 9 of the drive shaft 5 may exhibit a gradual change in diameter along such end sections 9a, 9b located distally and proximally to the distal and proximal ends of the seat 100. The gradual change in the outer diameter of the drive shaft 5 from a smaller diameter to an increased diameter along its increased diameter region 9 is preferable so that a sudden step change in the diameter of the drive shaft 5 can be avoided. A similar waisted portion 10 or seat 100 may be formed in the drive shaft 5 to mount at least one of the counterweights 8 to the drive shaft 5.

Figures 15A, 15B:
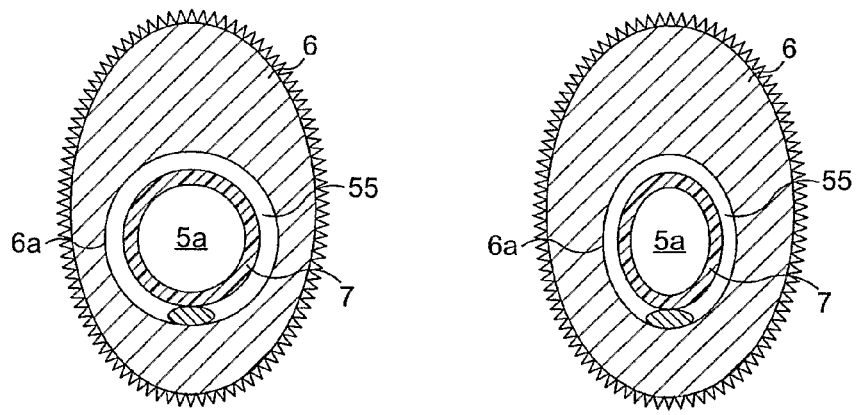

FIGS. 15A and 16A taken along lines X-X of FIGS. 15 and 16 show that a drive shaft 5 in the area of circumferential groove or seat 100 has a circular cross-section. Such circular cross-section of the drive shaft in the area of the circumferential groove or seat 100 may require special bonding of the abrasive element 6 to the drive shaft 5 in the area of the groove or seat 100 in order to prevent rotation of the abrasive element around the drive shaft 5.

To prevent rotation of the abrasive element 6 around the drive shaft 5, the drive shaft 5 may have a non-circular transverse cross-section (i.e. oval) along at least the length of the circumferential groove or seat 100 around which the abrasive element 6 is located. The aperture 6a in the abrasive element 6 may also have a matching non-circular transverse cross-section, as shown in the transverse cross-sectional representations of FIGS. 15B and 16B taken along lines X-X of FIGS. 15 and 16. Preferably, the drive shaft 5 has a non-circular, i.e. oval, transverse cross-section along a substantial length of the increased diameter region 9. The waisted portions 10 shown in FIGS. 13A. 13B and 14 may also be formed non-circular in transverse cross-section so as to prevent rotation of the abrasive element 6 or counterweights 8a,8b around the drive shaft 5.

In general any abrasive element 6, any counterweight 8a,8b or any support element(s) 508 may also have aperture(s) (opening(s)) with non-circular transverse cross-section(s) and may be mounted around the portion(s) of the drive shaft 5 which are formed with matching non-circular transverse cross-section(s) in order to prevent rotation of these elements around the drive shaft 5.

In the most preferred embodiment of the invention, the abrasive element 6 is spaced away from the distal end of the drive shaft 5 by a distance of not less than about 3 mm and not more than about 60 mm.

The drive shaft 5 is slideably received within a tubular sheath 12 that is advanced into the vessel 1 together with the drive shaft 5. Proximally, the drive shaft sheath 12 is connected to the sheath support housing 13. Distally, the drive shaft sheath 12 terminates proximal to the proximal counterweight 8b, as shown in FIGS. 2 through 7.

FIG. 17B shows sheath 12 terminating distally proximal to the proximal support element 508b. The sheath 12 may also terminate proximal to the abrasive element itself if the drive shaft does not have a counterweight or support element located proximal to the support element. FIG. 17B shows that a radiopaque ring or marker 512 may be placed near the distal end of the drive shaft sheath 12.

Proximal end portion of the sheath 12 has at least one wall opening 16a, which is used to communicate the lumen 23 in the sheath with conduit 14a and thereby enable fluid to be pumped into or drained from the lumen 23 of the sheath 12.

FIGS. 2 through 7 show that the lumen 23 of the sheath 12 is in communication with the conduit 14a via the wall opening 16a in the sheath and fluid port 15a, which is formed in the drive shaft sheath support housing 13. It is also envisaged that the wall opening(s) 16a in the sheath for communicating the lumen 23 with conduit 14a may be located more distally along the sheath 12 and distally to the drive shaft sheath support housing 13, thereby reducing the amount of fluid that may be spilt into the housing 13 from the proximal end 12b of the sheath 12. The fluid opening or port 15b is formed in the wall of the housing 13 to drain such spilt fluid from the housing 13 through the conduit 14b. The lumen 23 in the sheath is an annular lumen defined by the space between the inner diameter of the sheath 12 and the outer diameter of the drive shaft 5. The conduit 14a may be connected to a pump or suction device or to a peristaltic pump which can function as a pump or a suction device depending on the direction of rotation of its rollers. The conduit 14b may be connected to a suction device and a peristaltic pump may be used for such purpose. Neither pump(s) nor suction device(s) which may move fluids along the conduits 14a and 14b are shown. Potential advantages of using such pump(s) or suction device(s) will be explained below.

FIG. 14 shows, in longitudinal cross-section, the eccentric abrasive element 6 with convex outer surface 6b and inner surface 6c, the convex inner surface 6c being located within the waisted portion 10 of the drive shaft. Transition from convex outer surface 6b to convex inner surface 6c in any of the abrasive elements 6 is preferably rounded both distally and proximally. Examples of such rounded transitional zones between outer and inner surfaces of the abrasive elements 6 are illustrated by the oval or ovoid longitudinal cross-sections of the abrasive elements 6 shown in FIGS. 14, 16 and 16C.

FIG. 15 illustrates that at least one of two longitudinal cross-sections of the eccentric abrasive element 6 is circular, when such cross-section(s) are taken along any longitudinal plane which includes the longitudinal (rotational) axis Y-Y of the drive shaft 5.

The non-circular longitudinal cross-sections of the abrasive element 6 shown in FIGS. 16 and 16C illustrate that in the preferred embodiment of the invention, both the outer surface 6b and the inner surface 6c of the abrasive element 6 are convex. The convex inner surface 6c of the abrasive element 6 is located within the circumferential concave groove or seat 100 of the outer surface of the drive shaft 5.

The proximal end of the flexible fluid impermeable drive shaft 5 extends proximally beyond the proximal end 12b of the sheath 12 and through the rigid hollow bearing supported shaft 18 located within the bearing support housing 16 which is slideably received within drive shaft sheath support housing 13. The prime mover may be comprised by at least one turbine 17 mounted on a rigid hollow bearing supported shaft 18 which is connected to the flexible drive shaft 5 for rotation together with the flexible drive shaft 5. The rigid hollow shaft 18 is supported by bearings 19 mounted to the bearing support housing 16. The turbine 17 is located within the housing 16 so that its axis of rotation is substantially at a right angle to a gas supply port 20 extending radially from the wall of the housing 16 and to which a gas supply conduit 21 may be connected so that, when air or other gas is supplied under pressure through the gas supply conduit 21 and through the gas supply port 20 into the housing 16, it impinges on the turbine 17 causing the turbine 17, and the flexible drive shaft 5 to which it is operatively connected, to rotate relative to the housing 16 and to the sheath 12 mounted to the drive shaft sheath support housing 13.

It is envisages that an electric motor can also be used as a prime mover. In this case, the rigid hollow shaft 18 may serve as a shaft of the electric motor. It is also possible to mount a gear on the rigid hollow beating supported shaft 18 and through such gear connect shaft 18 to a gear or gearbox of the electric motor.

The bearing support housing 16 is slideably received within the sheath support housing 13 to enable longitudinal movements of housing 16 relative to the sheath support housing 13 in the directions of arrow "C" in FIG. 2, so that the drive shaft 5 may be moved in a longitudinal or axial direction further into or out of the sheath 12 to cause the abrasive element 6 to come into contact with and abrade the stenotic lesion 2 during treatment A flexible fluid supply hose 31 is connected to the proximal end portion of the fluid supply tube 22 for supplying flushing fluid from a remotely located source of pressurised flushing fluid (not shown) through the fluid supply tube 22 and into the drive shaft 5. It is possible to use commercially available or modified angiographic contrast injection system(s) as a source of pressurised fluid.

Furthermore, it is envisages that more than one source of pressurised fluid may be utilised for supplying pressurised flushing fluid into fluid supply tube 22 and fluid impermeable drive shaft 5. It is possible to use the syringe of almost any angiographic contrast injection system for supplying pressurised flushing fluid such as saline solution or liquid contrast material at very high pressure just before, during and immediately after rotation of the drive shaft 5 and use another source of pressurised flushing fluid (i.e. peristaltic pump) to ensure relatively slow flow of flushing fluid through the fluid supply tube 22 and, along the fluid impermeable drive shaft at a relatively low fluid pressure during time intervals when retrograde flow of flushing fluid around the abrasive element 6 is not provided by pumping fluid at very high pressure using the syringe of the angiographic contrast system.

Some angiographic contrast injection systems already incorporate two sources of fluid pressure as described above. At least one such contrast fluid injection system is commercially available from Assist Medical Systems Inc. of Eden Prarie, Minn., USA. It is also envisaged to connect in parallel two or more commercially available angiographic contrast injection systems in order to ensure that total syringe volume of the contrast injection systems is sufficient for safe operation of the rotational atherectomy device of the invention.

FIGS. 5a through 7 show a modified embodiment of the coupling of the flexible, hollow, fluid impermeable drive shaft 5 to the rigid, hollow, bearing supported shaft 18. In this embodiment, the drive shaft 5 does not extend proximally throughout the entire length of the bearing supported shaft 18, and only the proximal end portion of the flexible, hollow, fluid impermeable drive shaft 5 is coupled to a distal end portion of the rigid, hollow, bearing supported shaft 18 so that the drive shaft 5 rotates when the rigid, hollow, bearing supported shaft 18 is rotated. In this embodiment, the rigid hollow bearing supported shaft 18 slideable receives, through its distal end, the flushing fluid supply tube 22 therein to enable flushing fluid to be supplied from a source of pressurised flushing fluid through the fluid supply tube 22 and the rigid hollow, bearing supported shaft 18 into the flexible fluid impermeable drive shaft 5.

The rigid, hollow, bearing supported shaft 18 can freely rotate around a straight stationary fluid supply tube 22 coaxially received within it through its proximal end, thereby forming a rotatable fluid supply coupling between these two elements to facilitate the straight forward flow of flushing fluid from the distal end of the stationary fluid supply tube 22 into the rotatable hollow bearing supported shaft 18 and into the proximal end of the fluid impermeable drive shaft lumen 5a. Therefore, the present invention also provides a rotational atherectomy device that comprises a prime mover for rotating a hollow flexible drive shaft and, a fluid supply line for providing an antegrade flow of fluid along a lumen of said hollow flexible drive shaft. The fluid supply line may comprise a straight, stationary fluid supply tube at its distal end and a flexible fluid supply tube at its proximal end with at least the distal end portion of the straight, stationary fluid supply tube being located inside a hollow shaft of the prime mover. The hollow prime mover shaft and the straight, stationary hollow supply tube are coaxial relative to each other to permit rotation of the hollow prime mover shaft around said straight stationary fluid supply tube.

In another embodiment, illustrated in FIG. 8A, the rigid, hollow, bearing supported shaft 118 extends directly through the bearings 119 within the housing 116 and is mounted for rotation with respect to the housing 116. At least one gas turbine 117 is mounted on the rigid hollow bearing supported shaft 118 to facilitate rotation of the rigid hollow shaft 118 relative to the housing 116, as explained above. The proximal end 118a of the rigid hollow bearing supported shaft 118 terminates shortly after emerging from the proximal bearing 119 and widens out to form a funnel shaped mouth 130. A fluid supply tube 122 is removably inserted into the proximal end portion of the hollow bearing supported shaft 118, facilitated by the funnel shaped mouth 130. The fluid supply tube 122 remains stationary with respect to the hollow bearing supported shaft 118 and the flexible fluid impermeable drive shaft 5 (not shown in FIG. 8A), which is operatively connected to the distal end portion of the hollow bearing supported shaft 118 and rotates together with it. In this embodiment, the rigid hollow bearing supported shaft 118 rotates around the stationary fluid supply tube 122 thereby forming a rotatable flushing fluid supply coupling comprising these two elements and facilitating the flow of flushing fluid in a straight forward direction from the distal end of the stationary fluid supply tube 122 directly into the rotatable hollow bearing supported shaft 118 and into the proximal end of the fluid impermeable drive shaft lumen 5a (not shown in FIG. 8A). The flow of flushing fluid in a straight forward direction from the distal end of the stationary fluid supply tube 122 into the hollow bearings supported shaft 118 and/or fluid impermeable drive shaft 5 is indicated by arrows "A" in FIGS. 4A through 9 and many of the other Figures. A flexible fluid supply hose 131 is connected to the proximal end portion 133 of the fluid supply tube 122 for supplying flushing fluid from a remotely located source of pressurised flushing fluid (not shown).

FIG. 8A also shows a fluid supply tube coupling member 135 which is mounted on the fluid supply tube 122. The fluid supply tube 122 extends through its coupling member 135. The coupling member 135 becomes releasably attached to the bearing support housing 116 after the fluid supply tube 122 has been received into the rigid hollow bearing supported shaft 118. It will be appreciated that the coupling member 135 cannot be properly connected to the bearing support housing 116 unless the fluid supply tube 122 has been properly inserted into the hollow bearing supported shaft 118. This ensures that the fluid supply tube 122 is correctly inserted into the hollow bearing supported shaft 118.

It will be appreciated that the outer diameter of the fluid supply tube 122 is smaller than the inner diameter of the hollow bearing supported shaft 118 and the hollow bearing supported shaft 118 has a larger inner diameter than the outer diameter of the flexible drive shaft 5. In one embodiment, the inner diameter of the rigid hollow bearing supported shaft 118 may be substantially larger than the outer diameter of the flexible drive shaft 5 and a special interconnecting element (not shown) may be needed to operatively connect the distal end portion of the hollow bearing supported shaft 118 to the proximal end portion of the flexible drive shaft 5. The smaller the clearance between the outer diameter of the fluid supply tube 122 and the inner diameter of the rigid hollow bearing supported shaft 118, the better the ratio between the amount of fluid that flows in a straight forward direction into the fluid impermeable lumen 5a of the flexible drive shaft 5 and the amount of fluid that flows in a retrograde direction through the annular space between the fluid supply tube 122 and the hollow bearing supported shaft 118. The retrograde flow of fluid along the annular space between the stationary fluid supply tube 122 and the rotatable hollow prime mover shaft 118 substantially reduces potential friction between them and allows the hollow, bearing supported shaft 118 to rotate freely around the fluid supply tube 122. Any flushing fluid that has flowed in a retrograde direction through the annular space between the fluid supply tube and the hollow bearing supported shaft is indicated by arrow "D" and may be drained out from the bearing support housing 116 and/or coupling member 135 via drainage openings in the housing 116 and/or coupling member 135. The flushing fluid which has flowed in a retrograde direction around the fluid supply tube 122 and which has been drained from the bearing support housing 116 (216 in FIG. 8B) and/or coupling member 135 (235 in FIG. 8B) may be re-circulated back into a flushing fluid container (not shown) via drainage port 260 and conduit 261, shown in FIG. 8B. The re-circulated flushing fluid may be used again for re-filling the syringe of the injection system or any other pump which is used to pump pressurised flushing fluid into the atherectomy device of the invention. A peristaltic pump (not shown) may be used to assist flow of drained flushing fluid along the conduit 261.

The fluid supply tube 122 may be made from a lubricious material such as, for example, PTFE. Also, it may be made from metal but coated on its outer surface with a lubricious material so that friction between the rotatable hollow bearing supported shaft 118 and the stationary fluid supply tube 122 is minimised. Alternatively, the hollow bearing supported shaft 118 may be made from a lubricious material or its inner surface coated or lined with a lubricious material.

The fluid supply tube coupling member 135 comprises at least one resiliently deformable arm 136 (two being shown in the embodiment of FIG. 8A, each having an enlarged head portion 137. The head portions 137 are slideably received within openings or windows 139 in the housing 116 once the arms 136 have been deflected by the application of pressure in a radially inward direction to enable the enlarged head 137 of each arm 136 to be moved into the bearing support housing 116 through its proximal opening 138 to locate each enlarged head 137 within the windows 139 located near the proximal end of the housing 116. The heads 137 and/or arms 136 may be deflected manually by the person connecting the coupling member 135 to the housing 116. However, the end face 140 of the housing 116 and the head 137 of each arm may be provided with appropriate angle or curvature so that, when the coupling member 135 is pushed distally against the housing 116 the heads 137 cooperate with the end face 140 of the housing 116 causing the heads 137 and the arms 136 to deflect in a radially inward direction. The housing 116 and/or the coupling member 135 may also be provided with one or more longitudinal grooves and recesses (not shown) which cooperate with each other so that the coupling member 135 may be attached to the housing 116 in only one orientation with respect to the circumference or perimeter of the housing 116.

The bearing support housing 116 is provided with windows 139 into which the head portion 137 of each arm 136 springs out when the coupling member 135 has been properly inserted into the housing 116. Removal of the coupling member 135 from the housing 116 is achieved by applying pressure simultaneously to each head portion 137 through the windows 139 to deflect the arms 136 radially inwardly so that each head portion 137 will clear the windows 139 to allow the coupling member 135 and its arms 136 to be pulled back and slide out of the housing 116.

Although a single turbine 17 is illustrated in the embodiments of FIGS. 2 through 9, it is envisaged that multiple gas turbines 17 may be mounted on the hollow bearing supported shaft 18.

A modified arrangement of the embodiment described with reference to FIG. 8A is illustrated in FIG. 8B. The device according to the embodiment shown in FIG. 8B has a substantially similar construction to the device of FIG. 8A. It is notable that the coupling member 235 of the embodiment shown in FIG. 8B extends over the outside of the bearing support housing 216 rather than being received within an opening in the bearing support housing 216. As with the embodiment of FIG. 8A, the hollow bearing support shaft 18 extends directly through the bearings 19 within the housing 216 and is mounted for rotation with respect to the housing 216. A gas turbine 17 is mounted on the hollow bearing supported shaft 18 to facilitate rotation of the hollow bearing supported shaft 18 relative to the housing 216, as previously explained with reference to FIG. 8A. The proximal end 18a of the hollow bearing supported shaft 18 terminates shortly after emerging from the proximal bearing 19 and widens out to form a funnel shaped mouth 130. A fluid supply tube 122 is removably received into the hollow bearing supported shaft 18. Its insertion into the shaft 18 is facilitated by the funnel shaped mouth 130 at the proximal end of the bearing supported shaft 18. The fluid supply tube 122 remains stationary with respect to the hollow bearing supported shaft 18 and the flexible drive shaft 5 (not shown in FIG. 8B), which is coupled to the distal end portion of the hollow bearing supported shaft 18 and rotates together with it. The hollow bearing supported shaft 18 and the fluid supply tube 122 together form a rotatable flushing fluid supply coupling which operates exactly as has already been described with reference to FIGS. 2 through 8. As shown in FIG. 9, a flexible fluid supply hose 131 is connected to the proximal end section 133 of the fluid supply tube 122 for supplying flushing fluid from a remote source of pressurised flushing fluid (not shown) directly into the fluid supply tube 122.

The fluid supply tube coupling member 235 is mounted on the fluid supply tube 122 and the fluid supply tube 122 extends through its coupling member 235. The coupling member 235 becomes releasably attached to the bearing support housing 216 after the fluid supply tube 122 has been propery advanced into the hollow bearing supported shaft 18.

The coupling member 235 comprises at least one resiliently deformable arm 236 (two being shown in the embodiment of FIG. 8B), each having a recessed region 240 formed in its inner surface. The arms 236 are slideably received over a proximal end portion of the bearing support housing 216. The proximal end portion 216a of the housing 216 is provided with at least one raised sections 241 corresponding in size and shape to the recessed regions 240 formed on the arms 236. The distal and proximal edges of the raised section(s) 241 are ramped or sloped, as are the corresponding edges of the recessed region(s) 240. The distal end of each arm 236 is also provided with an angled face 237.

When the coupling member 235 is moved distally around the proximal end portion of the housing 216, the angled faces 237 cooperate with the proximal ramped edge of the raised section 241. Further distal movement of the coupling member 235 around the housing 216 causes the arms 236 to resiliently deform by bending in a radially outward direction as the angled faces 237 travel up the proximal ramped edge of the raised section 241. The raised section 241 then locates in the recessed regions 240, thereby allowing the arms 236 to spring back into their non-deformed state. Removal of the coupling member 235 is thereby prevented by engagement of the raised section 241 on the housing 216 with the recessed region(s) 240 in the arm(s) 236. As with the previous embodiment, the housing 216 and/or the coupling member 235 may also be provided with one or more longitudinal grooves and recesses (not shown) which cooperate so that the coupling member 235 may be attached to the housing 216 in only one orientation with respect to the circumference or perimeter of the housing 216.

The non-circular cross sectional shape of an outer surface of the proximal end portion of the housing 216 and matching non-circular inner surface of the coupling member 135 may be also very effective in achieving proper circumferential orientation of housing 216 and coupling member 235 with respect to each other.

The above described connection between the fluid supply tube 122 and its coupling member 235 together with cooperating elements of the coupling member 235 and the housing 216 assure that the coupling member 235 cannot be connected to the housing 216 unless the fluid supply tube 122 has been properly advanced into the hollow bearing supported shaft 18. This ensures that the fluid supply tube 122 is correctly inserted into the hollow bearing supported shaft 18.

It will be appreciated that a specific circumferential orientation of the coupling member 235 with respect to the housing 216 becomes unnecessary if only flushing fluid supply tube 122 extends through the coupling member 235, as shown in FIGS. 8A and 8B.

To prevent inadvertent release of the coupling member 235 from the housing 216, the coupling member 235 includes a locking ring or collar 242 slideably mounted thereon. Once the coupling member 235 has been placed around the proximal end portion of the housing 216 with the raised section 241 of the housing 216 located in the corresponding recessed regions 240 of the coupling member 235, the collar 242 is moved distally around the coupling member 235 so that it overlies the distal ends of the arms 236. It will be appreciated that, in this position, the collar 242 prevents radially outward deflection of the arms 236 which is necessary to allow the coupling member 235 to be de-coupled from the housing 216 and so prevents inadvertent release of the coupling member 235 from the housing 216.

Prior to rotating the drive shaft 5 and abrading a stenotic lesion, the guidewire 3 is removed from the lumen in the fluid impermeable drive shaft 5 by withdrawing the guidewire from the proximal end of the drive shaft 5 in the direction indicated by the arrow "A" in FIG. 3. Similarly, in the embodiments shown in FIG. 8A and FIG. 8B, the guidewire is removed from the drive shaft 5 by pulling it from the proximal end of the hollow bearing supported shaft 18 before the coupling members 135 or 235 may be attached to their corresponding bearing support housings.

It will be appreciated that the guidewire 3 is only required to position the flexible drive shaft 5 in the correct location within the vessel to be treated with the abrasive element 6 adjacent to the stenotic lesion 2. Once the drive shaft has been located in the desired position using the guidewire, the guidewire 3 has fulfilled its function. In fact, the presence of the guidewire 3 can actually be a hindrance or cause problems during treatment as it causes drag during rotation of the drive shaft 5. Furthermore, if rotational force is repeatedly transferred from the drive shaft 5 to the guidewire 3, the guidewire 3 may break causing major procedural complications. As a consequence of this, the guidewire 3 employed with a rotational atherectomy device in which the guidewire 3 remains in situ during treatment must exhibit high torsional rigidity and strength to prevent breakage during rotation of the drive shaft 5. The eccentric abrasive elements and particularly eccentric abrasive elements provided with counterweights cause the guidewire to flex or deflect longitudinally during each turn of the drive shaft significantly increasing danger of breakage of the guidewire caused by metal fatigue which develops in the guidewire after one or several periods of continued rotation of the drive shaft 5 around the guidewire 3.

As the guidewire 3 is removed from the drive shaft 5 prior to treatment, according to the present invention, a conventional guidewire 3 can be used in the rotational device of the present invention because it is not required to have sufficient torsional and longitudinal strength to cope with the stresses (metal fatigue) placed on it by rotating drive shaft 5 around the guidewire 3. It is also desirable to remove the guidewire 3 from the drive shaft 5 so that the entire cross section of the lumen of the fluid impermeable drive shaft 5 is accessible for the flow of fluid therethrough, as shown in FIGS. 4A, 4B, 5A, 5B and many others.

The embodiments of FIGS. 9A and 9B also incorporate an optional but advantageous modification to the atherectomy device of the invention. In these embodiments, the device is equipped with an optical rotational speed sensing device. The rotational speed sensing mechanism shown in FIGS. 9A and 9B comprises a light emitting optical fibre, light receiving optical fibre and an actuating member which extends into a space between the light emitting and light receiving ends of these two fibres.

In the embodiment shown in FIG. 9A, light emitting optical fibre 155 extends from an inlet 149 in the wall of the housing 116 and makes a 90 degree turn within housing 116 so that its proximal light emitting end is facing the light receiving end of the light receiving optical fibre 157. The light receiving optical fibre 157 is mounted to the coupling member 135 and extends proximally therefrom.

FIG. 9B shows a slightly different fixation of the optical fibre 157. However, coaxial positioning of the end sections of light emitting and light receiving fibres is maintained. It will be appreciated that either of these two fibres may be selected as the light emitting or the light receiving fibre.

In the preferred embodiment, the light emitting fibre 155 is releasably coupled to a long optical extension fibre 158 using optical coupling 146 which is releasably connectable to the inlet 149 of the housing 116. Alternatively the light emitting fibre 155 may extend through the inlet 149 and have sufficient length for connection to a source of light (not shown) without use of the extension fibre 158. The light emitting and light receiving end portions of optical fibres 155 and 157 are longitudinally aligned but spaced away from each other. The actuating member 147, mounted on the drive shaft for rotation therewith, extends into the space between said light emitting and light receiving optical fibres 155,157. The actuating member 147 is preferably made in the form of a wheel or disc and is formed from a light opaque material with one or more hole(s) or opening(s) 148 therein so that, as the actuating member 147 rotates, a beam of light may pass through the openings 148 from the light emitting optical fibre 155 to the light receiving optical fibre 157 at a frequency which depends on the speed of rotation of the drive shaft 5 and actuating member 147. The frequency of the pulses of light generated by the rotating actuating member 147 is used to determine the speed of rotation of the drive shaft 5. Although, as mentioned above, the actuating member 147 is provided with one or more openings 148 therein through which light may pass from the light emitting optical fibre 155 to the light receiving optical fibres 157 it will be appreciated that the same effect will be achieved by providing the actuator 147 with a light transparent or translucent area(s) instead of hole(s) or opening(s) 148.

It will also be appreciated that, as the light receiving fibres 157 is attached to the coupling members 135 or 235, there will be no rotational speed measurement recorded if the coupling members 135 or 235 are not properly attached to their respective housings 116,216. This implies that the fluid supply tube 122 is not properly received within the rigid hollow bearing supported shaft 118 and provides a safety feature because if the physician attempts to initiate rotation of the drive shaft 5 before properly inserting the fluid supply tube 122 into the bearing supported shaft 118, he will immediately realise that there is a problem because no speed measurement signals will be generated. He will therefore be prompted to immediately deactivate the prime mover (turbine 117 in FIGS. 9A and 9B) to stop further rotation of the drive shaft 5 and to properly connect the coupling member 135,235 to their respective housings 116,216 before continuing the procedure. It is essential for the physician to be certain that the fluid supply tube 122 is properly coupled to the fluid impermeable drive shaft and that all fibres of the optical rotational speed sensing mechanism are properly connected or optically coupled with each other.

In the preferred embodiment of the invention, if the fluid supply tube 122 has not been properly received within the hollow bearing supported shaft 118 because the coupling members 135,235 have not been properly attached to their respective housings 116,216 prior to activation of the prime mover, then deactivation of the prime mover within not more than several revolutions of the prime mover will take place automatically by a microprocessor based controller.

It is envisaged that the optical extension fibre 158 is packaged and sterilised separately from the entire bearing support housing 116 or the entire handle assembly and may be easily coupled to optical fibres located within rotational devices having a different design of the drive shaft or the drive shaft having a different size or shape of abrasive element.

It is also envisaged that the designs of the optical rotational speed sensing mechanisms may be different but still be compatible with optical extension fibre or fibres 158.

Operation of the rotational atherectomy device to remove a stenotic lesion 2 from a blood vessel 1 of a patient will at first be described with reference to FIGS. 4A and 4B. Once the guidewire 3 has been removed from the drive shaft 5 by withdrawing it through the proximal end of the drive shaft 5, a flushing fluid supply tube 22 is inserted into the proximal end portion of the fluid impermeable drive shaft 5 through its proximal end 5b, thereby operatively coupling flushing fluid supply tube 22 to the flexible fluid impermeable drive shaft 5 and establishing fluid communication between the fluid impermeable drive shaft 5 and the source of pressurised flushing fluid (not shown) via relatively rigid flushing fluid supply tube 22 and the flexible fluid supply hose 31, which connects the proximal end of the tube 22 to a remotely located source of pressurised flushing fluid. As the flexible drive shaft 5 is formed from a fluid impervious material or is covered or lined with such a material forming fluid impervious membrane 7, the fluid pumped into the drive shaft 5 cannot pass through the wall of the drive shaft 5 into the drive shaft sheath 12 or into the vessel 1 itself and therefore it flows in an antegrade direction (in the direction indicated by arrow "A" in FIG. 4A and FIG. 4B) along the fluid impermeable lumen 5a of the drive shaft 5 and emerges into the vessel 1 from an opening located distal to the abrasive element 6. Although the drive shaft 6 may not be fluid impervious along a portion which extends distally beyond the abrasive element 6, in the embodiment shown in FIGS. 4A and 4B, the drive shaft 5 is fluid impervious along its entire length so that fluid is completely contained within it and can only pass into the vessel 1 from the distal end 4 of the drive shaft 5 and distally to the abrasive element 6 located thereon. The important consideration is that substantially all of the pressurised flowing flushing fluid is retained within the lumen 5a of the fluid impermeable drive shaft 5 and only enters the vessel 1 at a point distal to the abrasive element 6.

The supply of fluid through the drive shaft 5 is continued so that the fluid pressure in the vessel 1 distal to the point of entry of the fluid from the drive shaft 5 into the vessel 1 increases to a pressure at which a fluid pressure gradient is generated within the vessel 1 between a high pressure region distal to the point of entry of the fluid into the vessel 1 from the drive shaft 5 and, a low pressure region proximal to the point of entry of the fluid into the vessel 1 from the drive shaft 5. This fluid pressure gradient is maintained so that at least some of the fluid flowing in an antegrade direction through the drive shaft 5 and entering the vessel 1 from the drive shaft 5 is re-directed, due to the fluid pressure gradient, around the outside of the drive shaft 5 and flows in a retrograde direction (in the direction indicated by arrow "R", in FIGS. 4A and 4B) within the vessel 1 and around the abrasive element 6. Fluid which has flowed over the abrasive element 6 is then drawn into the sheath 12 where it flows in a retrograde direction along the annular channel 23 defined by the space between the drive shaft 5 inner surface of the wall of the sheath 12 and via the ports in the drive shaft sheath support housing 13 into the fluid conduits 14a, 14b and out of the patient. Although it is envisaged that retrograde flow can be generated without the provision of additional suction through the sheath 12, it will be appreciated that the sheath 12 can be in communication, via the fluid ports 15a, 15b and conduits 14a, 14b, with a suction device (not shown) to actively suck and draw the fluid which has flowed in a retrograde direction over the abrasive element 6, into the sheath 12 from the vessel 1.

Once a flow of pressurised flushing fluid has been established in an antegrade direction (indicated by arrow "A") through the fluid impermeable drive shaft 5 and back through the sheath 12 in the retrograde direction, rotation of the drive shaft 5 can be initiated by activating a supply of pressurised gas indicated by arrow "G" (i.e air or compressed nitrogen gas) to the turbine 17 though the gas supply conduit 21 and gas supply port 20 in the bearing support housing 16. Once the drive shaft 5 is rotating at the required speed, the bearing support housing 16 is slid relative to the sheath support housing 13 to move the abrasive element distally along the stenotic lesion 2 to abrade it. Alternatively, a relatively small eccentric abrasive element may be advanced beyond the stenotic lesion and rotated only when it is withdrawn across the stenosis. Due to the retrograde flow of fluid around the abrasive element 6, all the abraded particles (AP as shown in Figures) or debris are entrained in the retrograde flowing fluid and pass into the sheath 12 together with such fluid. The particles then either flow out of the device via the fluid condui 14a, which is in communication with the annular channel of the sheath 12 together with the flushing fluid or become trapped within the sheath 12 and are removed from the patient together with the device when the treatment has been completed. Debris and fluid which may spill into the sheath support housing 13 from the proximal end 12b of the sheath 12 maybe drained via drainage opening (port) 15b and conduit 14b.

It will be appreciated that an adequate flow of pressurised flushing fluid must be established and that the flushing fluid flow pressures must be monitored and controlled throughout the procedure to ensure that a retrograde flow of fluid is maintained around rotating abrasive element 6. Preferably only heparinised saline solution, liquid X-ray contrast or other flushing fluid may be pumped through the drive shaft 5. It will be appreciated that it is desirable to prevent the retrograde flow of blood around the abrasive element 6 as this can result in thrombosis or blockage of the annular channel 23 in the sheath 12 due to the damage to blood platelets and other elements of blood by the rotating abrasive element 6

Operation of the rotational atherectomy device shown in FIGS. 5A and 5B is similar to the operation of the device shown in FIGS. 4A and 4B. The design difference between these two device is associated with how the fluid impermeable drive shaft 5 is connected to the rigid hollow bearing supported shaft 18. In FIGS. 4A and 4B, the drive shaft 5 extends proximally throughout the entire length of the bearing supported shaft 18 while in FIGS. 5A and 5B the drive shaft 5 is connected only to the distal end or distal end portion of the bearing supported shaft 18. The fluid supply tube 22 in FIGS. 5A and 5B is inserted directly into the bearing supported shaft 18 and allows flushing fluid to be pumped in a straight forward direction from the distal end of the fluid supply tube 22 into the proximal end of the fluid impermeable lumen 5a of the drive shaft 5.

It should be noted that in all the above described embodiments, conduit 14a may be connected to both fluid pumping and fluid suction devices or a device such as a peristaltic pump which can perform both functions depending on the direction of rotation of its rollers. In such a case, it may be advantageous to initially pump pressurised flushing fluid in an antegrade direction along both the fluid impermeable drive shaft 5 and through the annular lumen 23 of the sheath 12, thereby rapidly flooding treated vessel 1 with flushing fluid and increasing fluid pressure in a region of the vessel located distal to the distal end of the sheath 12. The antegrade flow of flushing fluid along the annular lumen 23 of the sheath 12 is illustrated by arrows "F" in FIG. 5A. Just before initiating rotation of the drive shaft 5, the direction of fluid flow along the annular lumen 23 is reversed from antegrade to retrograde by deactivating the pump associated with fluid conduit 14a or disconnecting conduit 14a from fluid pumping device (not shown). It may be advantageous to not only disconnect the conduit 14a from the fluid pumping device but also to connect the conduit 14a to a suction device or change the direction of rotation of the peristaltic pump if such type of pump was used as the pumping device. The retrograde flow of flushing fluid around the abrasive element 6 and along the annular lumen 23 of the sheath 12 is illustrated by arrows "R" in FIG. 5B.

It should be noted that, starting to pump flushing fluid through along the fluid impermeable drive shaft 5 at very high fluid pressure just before initiating rotation of the drive shaft is not absolutely necessary and it may be more than sufficient to start injecting flushing fluid into the fluid impermeable drive shaft 5 at very high fluid pressure simultaneously with, or immediately after, rotation of the drive shaft has been initiated. It is also acceptable to stop injecting flushing fluid into the drive shaft 5 at very high fluid pressure simultaneously with, or just before, drive shaft has stopped rotating.

Operation of an alternative embodiment of the invention will now be described with reference to FIGS. 6A and 6B. The embodiment illustrated in these Figures is identical to that of the previous embodiments except in the construction of the drive shaft sheath 112 and the directions of fluid flow therethrough. In FIGS. 6A and 6B, the sheath 112 is formed with at least one discrete lumen 26 extending through the sheath 112 which is separate to the annular channel 23 defined between the drive shaft 5 and the wall of the sheath 112. Proximally, the or each discrete lumen(s) 26 is connected via a fluid port 27 to a fluid conduit 28 which is connected to a fluid pumping or fluid suction device (not shown) operable to pump flushing fluid in an antegrade direction into the discrete lumen(s) 26 or to draw flushing fluid into distal openings of the lumen(s) 26 to assist in the retrograde flow of the fluid along the discrete lumen(s) 26.

Although, in the embodiment shown in FIGS. 6A and 6B, the sheath 112 has a more complicated construction, it potentially has the advantage that debris is drawn into the discrete lumen 26 which is separate from the annular channel 23 and so potential blockage of the channel 23 with debris is avoided. This may be assured by pumping fluid in an antegrade direction not only through the lumen 5*a* of the drive shaft 5 but also through the annular channel 23 between the drive shaft 5 and the sheath 112 to lubricate the outer surface of the drive shaft 5 and reduce potential friction between the outer surface of the drive shaft 5 and the inner surface of the sheath 112.

FIG. 6A illustrates that it may again be advantageous initially to pump pressurised flushing fluid in an antegrade direction along the fluid impermeable lumen 5*a* of the drive shaft 5 and through all available lumens in the drive shaft sheath including the or each lumen(s) 26 separate from the annular lumen 23 of the sheath 12. This again allows the treated vessel to be rapidly flooded with flushing fluid and rapidly increase fluid pressure in that portion of the vessel, which is distal to the distal end of the sheath 12.

In FIG. 6A, the antegrade flow of flushing fluid along the annular lumen 23 is again illustrated by arrows "F" and similarly directed flow along the or each discrete lumen(s) 26 is illustrated by arrows "P". Just before initiating rotation of the drive shaft 5, the direction of fluid flow along the or each lumen(s) 26 separate from the annular lumen 23 is reversed from antegrade to retrograde using the same or similar technique(s) described above with respect to changing direction of fluid flow through annular lumen 23 of the sheath 12 in the embodiment shown in FIGS. 5A and 5B. Just immediately prior to or simultaneously with initiating rotation of the drive shaft 5, the antegrade fluid flow rate through the annular channel 23 around the drive shaft 5 is significantly reduced so that any flushing fluid entering the treated vessel 1 from the distal end of the annular lumen 23 has such low fluid pressure that it is immediately sucked into the lumen(s) 26 since it cannot flow against the fluid pressure gradient which by that time, has already been generated between an area distal to the abrasive element 6 and the distal end of the sheath 12 by the flushing fluid entering the treated vessel 1 from the fluid impermeable drive shaft 5. The same fluid pressure gradient is forcing at least a portion of the flushing fluid which entered the treated vessel from the fluid impermeable drive shaft 5 to flow in a retrograde direction around the abrasive element and into the or each discrete lumen(s) 26 in the sheath 12. Any debris removed by the rotating abrasive element 6 or otherwise released from the stenotic lesion 2 becomes entrained by that portion of the flushing fluid that has flowed in a retrograde direction around the drive shaft 5 and its abrasive element 6. The retrograde flow of fluid around the abrasive element 6 is indicated by arrows "R" in FIG. 6B. The redirection of the flushing fluid from the distal end of the annular lumen 23 into the or each discrete lumen(s) 26 is also indicated In FIG. 6B by arrows "F".

One more embodiment of the invention, and its operation, will now be described with reference to FIG. 7. This embodiment is identical to the embodiment described with reference to FIGS. 6A and 6B except that the outer surface of the sheath 212 is provided with an inflatable element 29 such as a cuff or balloon situated close to its distal end. In order to reduce or prevent antegrade flow of blood or retrograde flow of flushing fluid and debris between the inflatable element 29 and the wall of the vessel 1 during periods of treatment when the drive shaft 5 is rotated. An inflation lumen 30 extends along the length of the sheath 212 and is connected via an inflation conduit 31 to an inflation device (not shown) for supplying into the inflatable element 29 an inflation medium such as helium or other gas, which is soluble in blood and will not cause embolism in case of leakage or rupture of inflatable element 29. Fluid contrast material or saline may also be utilised as the inflation medium. The use of a gaseous inflation medium which is soluble in blood is preferable because a capilliary effect is avoided and short inflation and deflation times are enabled. The inflation device includes a pump (not shown) for pumping the inflation medium into the inflatable element in the direction of arrow "G" in FIG. 7. In one embodiment a conventional or modified syringe could be used as a pump for pumping the inflation medium into the inflatable element 29.

A modification of the embodiment of the invention shown in FIG. 7. In such an embodiment, an inflatable membrane which surrounds the sheath 212 is envisaged. One end of such inflatable membrane is connected to the sheath 212 close to its distal end and the other end of the inflatable membrane is connected to an inflation source so that the potential space between the sheath and the inflatable membrane becomes inflated when inflation medium is supplied into the potential space defined between the inflatable membrane and the sheath 212 in order to reduce or prevent the antegrade flow of blood or retrograde flow of flushing fluid and debris between the inflatable membrane and the wall of the vessel 1 during periods of treatment when the drive shaft 5 is rotated.

FIG. 5B$^I$ to FIG. 5B$^{III}$ is a series of drawings to show how the eccentric rotating abrasive element 6 of the atherectomy device of the invention shown in FIG. 5 is repeatedly moved across the stenotic lesion 2 in distal and proximal directions to remove a thin layer of the stenotic lesion with each pass of the abrasive element across the stenotic lesion. It should be noted how, as shown in FIGS. 5B$^I$ to 5B$^{III}$, that drive shaft 5 is bowed, the bowing of the drive shaft 5 being caused by the centrifugal forces applied to the drive shaft 5 by rotation of eccentric abrasive element 6 and its counterweights 8*a* and 8*b*. It should also be noted, and shown in FIGS. 5B$^I$ to 5B$^{III}$, as well as in many other Figures, that atherosclerotic particles AP are being entrained in retrograde flowing flushing fluid (illustrated by arrows "R") and are being removed from the treated vessel 1 and, even further, from the body of the patient.

FIG. 7$^I$ to FIG. 7$^{III}$ is a series of drawings to show how the eccentric rotating abrasive element 6 of the atherectomy device of the invention shown in FIG. 7 is repeatedly moved across the stenotic lesion 2 in distal and proximal directions to remove a thin layer of stenotic lesion with each pass of the abrasive element across the stenotic lesion.

FIG. 8A illustrates, in a longitudinal cross-section, the attachment of the flushing fluid supply tube coupling member to the bearing support housing. It should be noted that the flushing fluid supply line is comprised distally of a straight stationary fluid supply tube 122 and proximally of a flexible fluid supply tube or hose 131. The straight stationary fluid supply tube 122 at the distal end of the flushing fluid supply line is at least partially received within the hollow prime mover shaft 18. The straight stationary fluid supply tube 122 is also coaxial with the hollow prime mover shaft 18, thereby allowing rotation of the hollow prime mover shaft 18 around the straight stationary fluid supply tube 122.

FIG. 18A is similar to FIG. 17A except that it illustrates that the distal support element 777 is formed by the fluid impermeable membrane whilst the proximal support element 888 is solid.

The fluid impermeable membrane is comprised of two sections: a long fluid impermeable section 707 which lines the inner surface of the drive shaft 5 formed by coiled wire or wires 55; and, preferably, a shorter fluid impermeable section 700 which covers coiled wire or wires 55 on the outer surface of the drive shaft 5.

It should be understood that distal inflatable support element 777 may be formed at the distal end of the drive shaft 5 by first placing a preferably short section 700 of the fluid impermeable membrane around the outer surface of the drive shaft, and then inverting or invaginating the long section 707 of the fluid impermeable membrane inside the drive shaft 5 and pulling it throughout the entire length of the flexible drive shaft 5, thereby making the drive shaft 5 fluid impermeable.

It should be also be understood that the distal inflatable support element 777 may alternatively be formed at the distal end of the drive shaft 5 by first pulling the fluid impermeable section of the membrane 707 inside the drive shaft 5 along its entire length and then turning the remaining section of the fluid impermeable membrane radially outwardly and then backwards around the outer surface of the drive shaft 5, thereby forming both a fluid inflatable element 777 at the distal end of the drive shaft 5 and a shorter section 700 of fluid impermeable membrane which covers coiled wire or wires 55 on the outer surface of the drive shaft 5.

FIG. 18C is similar to FIG. 17A, except that it illustrates both distal inflatable support element 777d and proximal inflatable support element 777p formed by the fluid impermeable membrane. Fluid impermeable membrane may be made from stretchable or non-stretchable material. In the case where the fluid impermeable membrane is made from a non-stretchable material, the fluid inflatable support elements (i.e. 777d and/or 777p), may be formed by having the fluid impermeable membrane of an enlarged circumference along the length of the fluid inflatable support elements and then folding said sections of the membrane which form the inflatable elements, around the circumference of the drive shaft 5 in order to achieve a relatively small cross-sectional diameter of the drive shaft 5 in the area of the inflatable elements.

In the case wherein the fluid impermeable membrane is made from a stretchable material (e.g. silicon resin), the fluid impermeable membrane will be allowed to stretch in the areas where the membrane defines the outer walls of the fluid inflatable support elements (i.e. 777d and/or 777p), thereby eliminating the need for folding or furling the fluid impermeable membrane around the drive shaft 5.

FIG. 18D illustrates both distal inflatable support element 777d and proximal inflatable support element 777p being inflated by flushing fluid FF flowing first in the antegrade direction along a lumen of a fluid impermeable drive shaft 5. Said fluid inflatable support elements (i.e. 777d and/or 777p) become inflated by pressurised antegrade flowing flushing fluid FF entering said inflatable elements via openings (e.g. 800d and/or 800p) which are formed in that section 707 of the fluid impermeable membrane which lines the inner surface of the fluid impermeable drive shaft 5. These openings (e.g. 800d and/or 800p) are best illustrated in FIG. 18C, but are also shown in many other Figures.

FIGS. 18C and 18D also illustrate certain differences in design and function of distal and proximal fluid inflatable support elements. In contrast to the proximal fluid inflatable support element 777p, the distal fluid inflatable support element 777d allows fluid flow through said support element. The distal fluid inflatable support element 777d allows to change antegrade flow of flushing fluid FF along the drive shaft lumen to retrograde flow of a portion of said flushing fluid around the drive shaft 5 and its abrasive element. It should be noted that distal fluid inflatable support element 777d has at least one opening 808 located in the fluid impermeable membrane proximal to an area where the distal fluid inflatable support element 777d has its maximum diameter. Most preferably, such an opening or openings 808 are positioned in the fluid impermeable membrane such that flushing fluid exiting from said openings 808 is directed to flow in a retrograde direction around the fluid impermeable drive shaft 5 and its abrasive element (e.g. 666). This is achieved by positioning the opening or openings 808 in that portion of the fluid impermeable membrane of the distal fluid inflatable support element 777d which tapers inwards or faces rearwardly towards the abrasive element (e.g. 666) when the distal fluid inflatable support element 777d is inflated.

Glue or other bonding material 900 may be used along the portions of the drive shaft 5 to bond outer and inner layers of fluid impermeable membrane as well as isolate fluid inflatable elements.

FIG. 18B illustrates the inflatable distal support element 777 being inflated and the direction of flow of flushing fluid being changed from antegrade to retrograde as it passes from the lumen of the drive shaft 5 into the vessel through the inflated distal inflatable support element 777.

FIG. 18B$^I$ is a cross sectional view through the inflated inflatable element shown in FIG. 18B and illustrates how fluid pressure (arrows FP) of the flushing fluid FF maintains inflatable element in a distended state.

FIG. 18B$^{II}$ is a cross sectional view through the abrasive element 666 shown in FIG. 18B and illustrates its fixation on the drive shaft 5.

FIG. 18B$^{III}$ is a cross sectional view through the proximal solid support element 888 shown in FIG. 18B and illustrates its fixation on the drive shaft 5.

FIG. 18C$^I$ is a cross sectional view through the distal inflatable element 777d shown in FIG. 18C prior to inflation, the distal inflatable element 777d having a small crossing diameter by being made out of furled or folded non-stretchable membrane 700.

FIG. 18C$^{II}$ is a cross sectional view through the abrasive element 666 shown in FIG. 18C and illustrates its fixation on the drive shaft 5.

FIG. 18C$^{III}$ is a cross sectional view through is a cross sectional view through the proximal inflatable element 777p shown in FIG. 18C prior to inflation, the proximal inflatable element 777p having a small crossing diameter by being made out of furled or folded non-stretchable membrane 700.

FIG. 18E is similar to FIG. 18D, except that it illustrates the use of the fluid inflatable support elements 777d and 777p, and advantage of establishing retrograde flushing fluid flow through an opening(s) in a distal fluid inflatable support element 777d. Antegrade flushing fluid flow is illustrated by arrows A, and retrograde flushing fluid flow is illustrated by arrows R. As stenotic lesion 2 is being abraded by abrasive element 666, abraded particles AP are entrained by the retrograde fluid flow R and removed from the treated vessel 1 via drive shaft sheath 3500.

FIG. 18E$^I$ is an enlarged view of a portion of the distal inflatable support element 777d shown in FIG. 18E showing that the membrane 700 of the distal inflatable support element 777d is in contact with the inner surface of the outer curvature 1002 of the vessel 1.

FIG. 18E$^{II}$ is an enlarged view of a portion of the device shown in FIG. 18E to illustrates how rotating abrasive element 666 is biased to and preferentially removes stenotic tissue 2 along inner curvature 1001 of the treated vessel 1.

FIG. 18E$^{III}$ is an enlarged view of a portion of the proximal inflatable support element 777p shown in FIG. 18E showing that the membrane 700 of the proximal inflatable element 777p is in contact with the inner surface of the outer curvature 1002 of the vessel 1.

FIG. 18F is similar to FIG. 18E, except that it illustrates a bias provided to the abrasive element 666 by a magnetic force or forces, illustrated by arrows marked FIG. 19A is similar to FIG. 18A, except that it illustrates a drive shaft with an eccentric abrasive element 666e and a fluid inflatable distal counterweight 777ed while proximal counterweight 888ep is solid.

It should be understood that the fluid inflatable distal counterweight 777ed shown in FIG. 19A may be formed using substantially the same manufacturing method as with the fluid inflatable support elements described above. Fluid inflatable counterweights may be formed from fluid inflatable support elements by making such fluid inflatable support elements eccentric with a centre of mass of the fluid inflated element being located in the same plane as the centre of mass of the eccentric abrasive element, but diametrically opposite with respect to the longitudinal or longitudinal axis of the drive shaft. FIG. 19A$^I$ is a cross sectional view through the distal inflatable counterweight shown in FIG. 19A prior to inflation, the distal inflatable counterweight having a small crossing diameter by being made out of furled or folded non-stretchable membrane, which illustrates eccentric or asymmetric cross-sectional appearance of the inflatable counterweight, even when its membrane is furled or folded.

FIG. 19B$^I$ is a cross sectional view through the inflated inflatable counterweight shown in FIG. 19B and illustrates how fluid pressure (arrows FP) of the flushing fluid FF maintains the distal inflatable counterweight 777ed in a distended state. FIG. 19B$^I$ better illustrates eccentric or asymmetric shape of the distal inflatable counterweight 777ed. Centre of mass of such fluid filled distal inflatable counterweight 777ed is diametrically opposite to the centre of mass of eccentric abrasive element 666e shown next to it in transverse cross-section in FIG. 19B$^{II}$.

FIG. 19C shows a fluid impermeable drive shaft with an eccentric abrasive element 666e and fluid inflatable distal and proximal counterweights both of which are shown in a deflated state.

FIG. 19D is similar to FIG. 19C, except that the fluid inflatable counterweights 777ed and 777ep are both shown in an inflated state. It also shows how the direction of flushing fluid FF flow is changed from antegrade to retrograde as it passes from the drive shaft lumen into the vessel through the distal inflatable counterweight 777ed.

As shown in FIG. 19D, the distal separation distance between the distal inflatable counterweight 777ed and the abrasive element 666e is greater than a maximum longitudinal dimension of the abrasive element 666e. Also as shown in FIG. 19D, the proximal separation distance between the proximal inflatable counterweight 777ep and the abrasive element 666e is greater than the maximum longitudinal dimension of the abrasive element 666e.

FIG. 19E shows advancement of the fluid impermeable drive shaft 5 with furled or non-inflated inflatable counterweights 777ed and 777ep across the stenotic lesion 2 to be treated. Small crossing diameter of furled, non-inflated distal counterweight 777ed will allow to cross very tight stenotic lesions 2 which may not be crossed by a drive shaft 5 having solid distal counterweight.

FIG. 19F illustrates the device shown in FIG. 19D being rotated and curved by centrifugal forces created by rotating eccentric abrasive element 666e and rotating fluid inflated counterweights 777ed and 777ep.

FIG. 20A shows rounded radiopaque markers 2000 disposed within the fluid inflatable support elements 7777d and 7777p.

FIG. 20B is similar to FIG. 20A, except that it shows the fluid inflatable element 7777d and 7777p being inflated and rounded radiopaque markers 2000 disposed within the fluid inflatable support elements being moved in a radially outward direction within the fluid inflatable support elements by centrifugal forces generated by the rotating drive shaft.

FIG. 21A shows radiopaque markers 2000 disposed within the fluid inflatable counterweights 7777ed and 7777ep.

FIG. 21B, illustrates the use of the device similar to that shown in FIG. 19F but having rounded radiopaque markers 2000 disposed within the fluid inflatable counterweights 7777ed and 7777ep.

FIG. 22 is similar to FIG. 20B, except that the distal fluid inflatable support element has one or more additional openings 808f for providing antegrade flow of flushing fluid FF through said openings 808f out of the fluid inflated distal support element 7777d. Such opening 808f may be useful to provide antegrade flow of flushing fluid in cases when the centrifugal forces of the rapidly rotating drive shaft force all of the flushing fluid at the distal end of the drive shaft into the distal fluid inflatable support element 7777d via openings 800d.

FIG. 23 is similar to FIG. 22, except that it shows an eccentrically mounted abrasive element 6666e and eccentric counterweights 7777ed and 7777ep, the distal fluid inflatable counterweight 7777ed having one or more additional openings 808f for providing antegrade flow of flushing fluid FF through said openings 808f out of the fluid inflated distal counterweight 7777ed.

As shown in FIG. 23, the distal separation distance between the distal inflatable counterweight 7777ed and the abrasive element 6666e is greater than the maximum longitudinal dimension of the abrasive element 6666e. Also as shown in FIG. 23, the proximal separation distance between the proximal inflatable counterweight 7777ep and the abrasive element 6666e is greater than the maximum longitudinal dimension of the abrasive element 6666e.

FIG. 24A to FIG. 25B show how proximal fluid inflatable support elements 77777p or counterweights 77777ep may be formed only by a section 700 of the fluid impermeable membrane covering the drive shaft along the length of the proximal support elements 77777p or counterweights 77777ep.

FIG. 26A to FIG. 27 are generally similar to FIG. 24A to FIG. 25B and illustrate formation of circumferential inwardly distendable lip 9000 at the distal end of the distal inflatable support element 777777d or counterweight 777777ed.

It will be appreciated that the flexible drive shaft 5 and sheaths 12,112 and 212 as shown in the drawings are much shorter than is actually the case, for ease of illustration. Similarly, the sheath support housing, bearing support housing and the entire handle assembly are shown shorter than their actual length so that the potential longitudinal movement of the bearing support housing with respect to the sheath support housing is longer than is apparent from the accompanying drawings.

Many modifications and variations of the invention falling within the terms of the following claims will be apparent to those skilled in the art and the foregoing description should be regarded as a description of the preferred embodiments only.

The invention claimed is:

1. A rotational atherectomy device for removing a stenotic lesion from within a vessel of a patient, the device comprising:
   a rotatable, flexible, hollow fluid impermeable drive shaft having a longitudinal axis of rotation;
   an eccentric abrasive element having a solid body that defines a fixed size and being rigidly mounted to the drive shaft on a region of the drive shaft proximal to and spaced away from its distal end; and
   two fluid inflatable counterweights fixed to the drive shaft so as to rotate together with the abrasive element, each of the two fluid inflatable counterweights having a maximum outer diameter that is smaller than a maximum outer diameter of the abrasive element, the inflatable counterweights comprising:
      a distal fluid inflatable counterweight located at a distal end of the drive shaft and spaced away from the abrasive element by a distal separation distance, and
      a proximal fluid inflatable counterweight located on the drive shaft proximal to and spaced away from the abrasive element by a proximal separation distance,
      each of the distal separation distance and the proximal separate distance being greater than a maximum longitudinal dimension of the abrasive element.

2. A rotational atherectomy device according to claim 1 wherein the distal fluid inflatable counterweight includes at least one inflow opening communicating a lumen of the fluid impermeable drive shaft with an interior space of the distal fluid inflatable counterweight, said space at least partially defined by a fluid impermeable membrane.

3. A rotational atherectomy device according to claim 2 wherein the distal fluid inflatable counterweight includes at least one outflow opening communicating the interior space of the distal fluid inflatable counterweight with a vascular space within the vessel of the patient.

4. A rotational atherectomy device according to claim 3 wherein the at least one outflow opening is located in a portion of the fluid impermeable membrane which tapers inwards and faces rearwards towards the abrasive element when the distal fluid inflatable counterweight is inflated.

5. A rotational atherectomy device according to claim 3 wherein the distal fluid inflatable counterweight is configured to convert a flow of fluid in an antegrade direction along the fluid impermeable drive shaft to a retrograde flow of fluid around the fluid impermeable drive shaft and its abrasive element.

6. A rotational atherectomy device according to claim 1 wherein the proximal fluid inflatable counterweight includes at least one inflow opening communicating a lumen of the fluid impermeable drive shaft with an interior space of the proximal inflatable counterweight, said space at least partially defined by a fluid impermeable membrane.

7. A rotational atherectomy device according to claim 1 wherein a center of mass of each of the inflated distal and proximal fluid inflatable counterweighs is located in the same plane as a center of mass of the eccentric abrasive element, but diametrically opposite with respect to the rotational axis of the fluid impermeable drive shaft.

8. A rotational atherectomy device according to claim 1 wherein the fluid impermeable drive shaft is insertable into the vessel to be treated to enable flushing fluid to be pumped into the fluid impermeable drive shaft through its proximal end portion in an antegrade direction, wherein the flushing fluid passing through the fluid impermeable drive shaft exits through at least one port in the fluid impermeable drive shaft located distally to the abrasive element.

9. A rotational atherectomy device according to claim 8 wherein, in response to the flushing fluid exiting through said at least one port in the fluid impermeable drive shaft, the flushing fluid develops distal to the abrasive element such fluid pressure in the vessel which is sufficient to generate a retrograde flow of at least a portion of the flushing fluid around the abrasive element and the fluid impermeable drive shaft for removal from the treated vessel debris abraded by the rotating abrasive element during rotation of the drive shaft and entrained in the retrograde flowing flushing fluid.

10. A rotational atherectomy device according to claim 1 further comprising a guidewire that is slidably receivable in a lumen of the drive shaft.

11. A rotational atherectomy device according to claim 10 wherein the center of mass of each of the abrasive element and the two fluid inflatable counterweights is offset from the longitudinal axis of rotation such that a distal end section of the drive shaft located between the two fluid inflatable counterweights flexes to a curved shape in response to rotation of the drive shaft after the guidewire is withdrawn.

* * * * *